(12) United States Patent
Kaznessis et al.

(10) Patent No.: US 11,533,915 B2
(45) Date of Patent: Dec. 27, 2022

(54) METHODS FOR MAKING AND USING ANTIMICROBIAL PEPTIDES

(71) Applicant: REGENTS OF THE UNIVERSITY OF MINNESOTA, Minneapolis, MN (US)

(72) Inventors: Yiannis J. Kaznessis, New Brighton, MN (US); Katherine G. Volzing, Princeton, NJ (US); Juan Borrero Del Pino, Cork (IE); Gary Dunny, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 0 days.

(21) Appl. No.: 17/067,121

(22) Filed: Oct. 9, 2020

(65) Prior Publication Data
US 2021/0030817 A1    Feb. 4, 2021

Related U.S. Application Data

(62) Division of application No. 15/894,408, filed on Feb. 12, 2018, now Pat. No. 10,813,956, which is a division of application No. 14/431,044, filed as application No. PCT/US2013/061659 on Sep. 25, 2013, now Pat. No. 9,925,223.

(60) Provisional application No. 61/705,489, filed on Sep. 25, 2012.

(51) Int. Cl.
| | |
|---|---|
| *A01N 63/50* | (2020.01) |
| *C12N 15/74* | (2006.01) |
| *A61K 35/744* | (2015.01) |
| *A61K 38/10* | (2006.01) |
| *A61K 38/16* | (2006.01) |
| *C07K 7/08* | (2006.01) |
| *C07K 14/00* | (2006.01) |
| *A61K 35/00* | (2006.01) |

(52) U.S. Cl.
CPC ............ *A01N 63/50* (2020.01); *A61K 35/744* (2013.01); *A61K 38/10* (2013.01); *A61K 38/16* (2013.01); *C07K 7/08* (2013.01); *C07K 14/001* (2013.01); *C12N 15/746* (2013.01); *A61K 2035/11* (2013.01)

(58) Field of Classification Search
CPC ...... A01N 63/50; A61K 35/744; A61K 38/10; A61K 2035/11; C07K 7/08; C07K 14/001; C12N 15/746
See application file for complete search history.

(56) References Cited

U.S. PATENT DOCUMENTS

| | | | |
|---|---|---|---|
| 5,968,569 A | 10/1999 | Cavadini et al. | |
| 5,994,306 A | 11/1999 | Chang et al. | |
| 7,915,026 B2 | 3/2011 | Keasling et al. | |
| 7,927,584 B2 | 4/2011 | Allende | |
| 7,935,334 B2 | 5/2011 | Lin | |
| 7,935,501 B2 | 5/2011 | Jensen et al. | |
| 7,988,960 B2 | 8/2011 | Isolauri et al. | |
| 9,925,223 B2 | 3/2018 | Kaznessis et al. | |
| 2003/0027286 A1 | 2/2003 | Haselbeck et al. | |
| 2005/0084483 A1 | 4/2005 | Leedle et al. | |
| 2005/0260715 A1 | 11/2005 | Burian et al. | |
| 2010/0316643 A1 | 12/2010 | Eckert et al. | |
| 2018/0236013 A1 | 8/2018 | Kaznessis et al. | |

FOREIGN PATENT DOCUMENTS

| | | |
|---|---|---|
| EP | 0862448 A4 | 3/1999 |
| WO | WO 97/18826 A1 | 5/1997 |

OTHER PUBLICATIONS

International Search Report and Written Opinion for PCT/US2013/061659 from the U.S. Patent Office as the International Search Authority; dated Jan. 29, 2014: 19 pgs.
International Preliminary Report on Patentability for PCT/US2013/061659 from the International Bureau of WIPO, dated Apr. 9, 2015; 15 pgs.
Acuna et al., "Development of wide-spectrum hybrid bacteriocins for food biopreservation," *Food Bioprocess Tech.*, Aug. 2011;4(6):1029-1049.
Ahmed et al., "Impact of consumption of different levels of *Bifidobacterium lactis* HN019 on the intestinal microflora of elderly human subjects," *J Nutr Health Aging*, 2007;11(1):26-31.
Amalaradjou et al., "Chapter 5—Modern approaches in probiotics research to control foodborne pathogens," *Adv Food Nutr. Res.*, 2012;67:185-239.
"ATCC No. 4356," American Type Culture Collection, organism: *Lactobacillus acidophilus*; designation: Scav [IFO 13951, M Rogosa 210X, NCIB 8690, P.A. Hansen L 917] [online]; Manassas, VA [retrieved on Dec. 9, 2015] from the Internet; 2 pgs.
"ATCC No. 11842," American Type Culture Collection, organism: *Lactobacillus delbrueckii subsp. bulgaricus*; designation: Lb14 [IAM 12472, IFO 13953] [online]; Manassas, VA [retrieved on Dec. 9, 2015] from the Internet; 2 pgs.

(Continued)

*Primary Examiner* — Iqbal H Chowdhury
(74) *Attorney, Agent, or Firm* — Mueting Raasch Group

(57) ABSTRACT

Provided herein are genetically modified microbes. In one embodiment, a genetically modified microbe includes an exogenous polynucleotide that includes a pheromone-responsive region. In one embodiment, the pheromone-responsive region is derived from a conjugative plasmid from a member of the genus *Enterococcus* spp. The pheromone-responsive region includes a pheromone-responsive promoter and an operably linked coding region encoding an antimicrobial peptide. In one embodiment, a genetically modified microbe includes an exogenous polynucleotide that includes a promoter and an operably linked coding sequence encoding an antimicrobial peptide, where expression of the coding region is controlled by a modulator polypeptide and is altered by a modulating agent, and where the coding region encodes an antimicrobial peptide.

5 Claims, 26 Drawing Sheets

Specification includes a Sequence Listing.

(56) References Cited

OTHER PUBLICATIONS

"ATCC No. 14028," American Type Culture Collection, organism: *Salmonella enterica subsp. Enterica serovar Typhimurium*; designation: CDC 6516-60 [online]; Manassas, VA [retrieved on Dec. 9, 2015] from the Internet; 2 pgs.

"ATCC No. 23272," American Type Culture Collection, organism: *Lactobacillus reuteri*; designation: F275 [DSM 20016] [online]; Manassas, VA [retrieved on Dec. 9, 2015] from the Internet; 2 pgs.

"ATCC No. 47077," American Type Culture Collection, organism: *Enterococcus faecalis*; designation: OG1RF [online]; Manassas, VA [retrieved on Dec. 9, 2015] from the Internet; 1 pg.

"ATCC No. 55730," American Type Culture Collection, organism: *Lactobacillus reuteri*, SD2112; designation: Lactobacillus reuteri, SD2112 [online]; Manassas, VA [retrieved on Dec. 9, 2015] from the Internet; 1 pg.

"ATCC No. 700802," American Type Culture Collection, organism: *Enterococcus faecalis*; designation: V583 [online]; Manassas, VA [retrieved on Dec. 9, 2015] from the Internet; 2 pgs.

Aymerich et al., "Biochemiocal and Genetic Characterization of Enterocin A from *Enterococcus Faecium*, a New Antilisterial Bacteriocin in the Pediocin Family of Bacteriocins," *Appln Environ Microbiol.*, May 1996;62(5):1676-1682.

Aziz et al., "The RAST Server: rapid annotations using subsystems technology," *BMC Genomics*, Feb. 8, 2008;9:75:15 pgs.

Bassetti et al., "New treatment options against gram-negative organisms," *Crit Care*, 2011;15:215: 9pgs.

Bennett et al., "Analogous telesensing pathways regulate mating and virulence in two opportunistic human pathogens," *MBio*, Sep. 7, 2010;1(4):e00181-10.

Berman et al., "Daily ingestion of a nutritional probiotic supplement enhances innate immune function in healthy adults," *Nutr Res*, Sep. 2006(9);26:454-459.

Bermúdez-Humarán et al., "Lactococci and lactobacilli as mucosal delivery vectors for therapeutic proteins and DNA vaccines," *Microb. Cell Fact.*, 2011;10:S4.

Binladen et al., "The use of coded PCR primers enables high-throughput sequencing of multiple homolog amplification products by 454 parallel sequencing," *PLoS One*, 2007; 2, e197: 9 pgs.

Bolintineau et al., "Antimicrobial mechanism of pore-forming protegrin peptides: 100 pores to kill *E. coli*," *Peptides*, Jan. 2010;31(1):1-8.

Borrero et al., "Use of the *usp*45 lactococcal secretion signal sequence to drive the secretion and functional expression of enterococcal bacteriocins in *Lactococcus lactis*," *Appln Microbiol Biotechnol.*, Jan. 2011;89(1):131-143.

Borrero et al., Protein expression vector and secretion signal peptide optimization to drive the production, secretion, and functional expression of the bacteriocin enterocin A in lactic acid bacteria, *Journal of Biotechnology*, Oct. 20, 2011;156(1):76-86.

Braat et al., "A phase I trial with transgenic bacteria expressing interleukin-10 in Crohn's disease," *Clin Gastroenterol. Hepatol*, Jun. 2006;4(6):754-759.

Brockmeier et al., "Systematic screening of all signal peptides from Bacillus subtilis: A powerful strategy in optimizing heterologous protein secretion in Gram-positive bacteria," *J Mol. Biol.*, Sep. 22, 2006;362(3):393-402.

Brogden et al., "Antimicrobial peptides: pore formers or metabolic inhibitors in bacteria?" *Natl Rev Microb*, Mar. 2005;3(3):238-250.

Bryan et al., "Improved Vectors for Nisin-Controlled Expression in Gram-Positive Bacteria," *Plasmid*, 2000;44: 183-190.

Buttaro et al., "Cell-Associated Pheromone Peptide (cCF10) Production and Pheromone Inhibition in *Enterococcus faecalis*," *J Bacteriol*, Sep. 2000;182(17):4926-4933.

Cameron et al., "Directed osteogenic differentiation of human mesenchymal stem/precursor cells on silicate substituted calcium phosphate," *Journal of Biomedical Materials Research. Part A*, Jun. 26, 2012;101A(1):13-22.

Caserta et al., "In vivo and in vitro analyses of regulation of the pheromone-responsive prgQ promoter by the PrgX pheromone receptor protein," *J Bacteriol*, Jul. 2012; 194(13):3386-3394.

Cassone et al., "Scope and limitations of the designer proline-rich antibacterial peptide dimer, A3-APO, alone or in synergy with conventional antibiotics," *Peptides*, Nov. 2008;29(11):1878-1886.

Cattoir and Leclercq et al., "Twenty-Five years of shared life with vancomycin-resistant enterococci: is it time to divorce?" *J Antimicrob Chemother*, Apr. 2013;68(4):731-742.

Chatterjee et al., "Convergent transcription confers a bistable switch in *Enterococcus faecalis* conjugation," *PNAS USA*, Jun. 7, 2011;108(23):9721-9726.

Chatterjee et al., "Antagonistic self-sensing and mate-sensing signaling controls antibiotic-resistance transfer," *PNAS USA*, Apr. 23, 2013;110(17):7086-7090.

Chikindas et al., "Pediocin PA-1, a bacteriocin from Pediococcus acidilactici PAC1.0, forms hydrophilic pores in the cytoplasmic membrane of target cells," *Appl Environ Microbiol.*, Nov. 1993;59(11): 3577-84.

Chopin et al., "Two plasmid-determined restriction and modification systems in *Streptococcus lactis*," *Plasmid*, 1984; 11:260-263.

Chou et al., "Vancomycin-resistant enterococcal bacteremia: comparison of clinical features and outcome between *Enterococcus faecium* and *Enterococcus faecalis*," *J Microbiol Immunol Infect*, Apr. 2008;41(2):124-129.

Chung et al., "Transcriptional Analysis of a Region of the *Enterococcus faecalis* Plasmid pCF10 Involved in Positive Regulation of Conjugative Transfer Functions," *J of Bacteriology*, Apr. 1995;177(8):2118-2124.

Cintas et al., "Biochemical and Genetic Characterization of Enterocin P, a Novel sec-Dependent Bacteriocin from Enterococcus faecium P13 with a Broad Antimicrobial Spectrum," *Appl Environ Microbiol*, Nov. 1997;63(11):4321-4330.

Clewell and Dunny, "Conjugation and Genetic exchange in Enterococci," *The Enterococci:Pathogenesis, Molecular Biology, and Antibiotic Resistance*, Eds. Gilmore et al., ASM Press, 2002; Chapter 7:265-300.

Cole et al., "The Ribosomal Database Project: improved alignments and new tools for rRNA analysis," *Nucleic Acids Research*, 2009; 37, D141-D145.

Conlon et al., "Analogues of the frog skin peptide alyteserin-2a with enhanced antimicrobial activities against Gram-negative bacteria," *J. Peptide Sci.*, Mar. 5, 2012;18: 270-275.

Conlon et al., "The alyteserins: two families of antimicrobial peptides from the skin secretions of the midwife toad *Alytes obstetricans* (Alytidae)," *Peptides*, Jun. 2009;30(6): 1069-1073.

Cotter et al., "Bacteriocins: developing innate immunity for food," *Nat Rev Microbiol*, Oct. 2005;3(10):777-788.

Cotter et al., "Bacteriocins—a viable alternative to antibiotics?," *Nat Rev Microbiol*, Feb. 2013;11:95-105.

Davies et al., "Investigation of the distribution and control of *Salmonella enterica* serovar Enteritidis PT6 in layer breeding and egg production," *Avian Pathology*, Jun. 2003; 32(3): 227-237.

De Boever et al., "*Enterococcus faecalis* conjugative plasmid pAM373: complete nucleotide sequence and genetic analysis of sex pheromone response," *Molecular Microbiology*, 2000;37(6):1327-1341.

Degering et al., "Optimization of protease secretion in Bacillus subtilis and Bacillus licheniformis by screening of homologous and heterologous signal peptides," *Appl Environ Microbiol.*, Oct. 2010;76(19):6370-6376.

De Greef et al., "Probiotics and IBD," *Acta Gastroenterol. Belg.*, Mar. 2013;76(1):15-9.

DeRuyter et al., "Functional analysis of promoters in the Nisin gene cluster of *Lactococcus lactis*," *J Bacteriol.*, Jun. 1996;178(12):3434-3439.

DeSantis et al., "Greengenes, a chimera-checked 16S rRNA gene database and workbench compatible with ARB," *Appl Environ Microbiol.*, Jul. 2006; 72(7):5069-5072.

Deshpande et al., "Antimicrobial resistance and molecular epidemiology of vancomycin-resistant enterococci from North America and Europe: a report from the SENTRY antimicrobial surveillance program," *Diagn Microbiol Infect Dis.*, Jun. 2007;58(2):163-170.

Dethlefsen et al., "The pervasive effects of an antibiotic on the human gut microbiota, as revealed by deep 16S rRNA sequencing," *PLoS Biology*, Nov. 2008;6(11):e280: 18 pgs.

(56) References Cited

OTHER PUBLICATIONS

De Vos, W. M. "Gene expression systems for lactic acid bacteria," *Curr. Opin. Microbiol.*, Jun. 1999;2(3):289-295.

Diep et al., "Evidence for dual functionality of the operon plnABCD in the regulation of bacteriocin production in Lactobacillus plantarum" Mol Microbiol, Aug. 2001; 41(3):633-44.

Diep et al., "Ribosomally synthesized antibacterial peptides in gram positive bacteria," *Curr Drug Targets*, Apr. 2002; 3(2):107-122.

Diep et al., "Use of lactobacilli and their pheromone-based regulatory mechanism in gene expression and drug delivery," *Curr Pharm Biotech*, Jan. 2009;10(1):62-73.

Drouault et al., "The peptidyl-prolyl isomerase motif is lacking in PmpA, the PrsA-like protein involved in the secretion machinery of Lactococcus lactis," *Appl Environ Microbiol.*, Aug. 2002;68(8):3932-3242.

Dunny, "The peptide pheromone-inducible conjugative system of Enterococcus faecalis plasmid pCF10: cell-cell signaling, gene transfer, complexity and evolution," *Philos Trans R Soc Lond B Biol Sci*, Jul. 29, 2007;362(1483):1185-1193.

DuPont, "The growing threat of foodborne bacterial enteropathogens of animal origin," *Clin.Infect.Dis.*, Nov. 15, 2007;45(10):1353-1361.

Dylaq et al., "Probiotics in the mechanism of protection against gut inflammation and therapy of gastrointestinal disorders," *Curr Pharma Design.*, 2014;20:1149-1155.

Epand et al., "Bacterial membrane lipids in the action of antimicrobial agents," *J. Pept. Sci.*, 2011; 17: 298-305.

Fahrner et al., "Solution structure of protegrin-1, a broad-spectrum antimicrobial peptide from porcine leukocytes," *Chemistry & Biology*, Jul. 1996;3:543-550.

Joint FAO/WHO Expert Consultation, "Health and Nutritional Properties of Probiotics in Food Including Powder Milk with Live Lactic Acid Bacteria" Cordoba, Argentina Oct. 1-4, 2001; 56 pgs.

"Joint FAO/WHO/OIE expert meeting on critically important antimicrobials," Rome Italy: Nov. 26-30, 2007; 67 pgs.

Fenton et al., "Recombinant bacteriophage lysins as antibacterials," *Bioeng Bugs*, Jan.-Feb. 2010;1(1):9-16.

Fischetti et al., "Bacteriophage lysins as effective antibacterials," *Curr Opin Microbiol*, Oct. 2008;11:393-400.

Fox et al., "Campylobacter jejuni infection in the ferret: An animal model of human campylobacteriosis," *Am J Vet Res.*, Jan. 1987;48(1):85-90.

Frank, D. "XplorSeq: a software environment for integrated management and phylogenetic analysis of metagenomic sequence data," *BMC bioinformatics*, 2008; 9, 420; 16 pgs.

Frelet-Barrand et al., "Chapter 5—Membrane protein expression in Lactococcus lactis," *Methods Mol. Biol.*, 2010;601:67-85.

Ganz et al., "Antibiotic peptides from higher eukaryotes: biology and applications," *Mol Med Today*, 1999;5:292-297.

Gerasimov et al., "Probiotic supplement reduces atopic dermatitis in preschool children: a randomized, double-blind, placebo-controlled, clinical trial," *Am J. Clin Dermatol*, 2010;11(5):351-361.

Gibson et al., "An evaluation of probiotic effects in the human gut: microbial aspects," final Technical report for FSA project ref G01022, 2005: 22 pgs.

Giles et al., "A phase III, randomized, double-blind, placebo-controlled, study of iseganan for the reduction of stomatitis in patients receiving stomatotoxic chemotherapy," *Leukemia Research*, Jun. 2004;28(6):559-565.

Gillor et al., "Colicins and microcins: the next generation antimicrobials," *Advances in Applied Microbiology*, 2004;54: 129-146.

Gräslund et al., "Protein production and purification," *Natl Methods*, Feb. 2008;5(2):135-146.

Gruenheid and Moual, "Resistance to antimicrobial peptides in Gram-negative bacteria," *FEMS Microbiol. Lett.*, 2012;330:81-89.

Hancock, "Cationic peptides: effectors in innate immunity and novel antimicrobials," *The Lancet Infectious Diseases*, Oct. 2001; 1(3):156-164.

Hancock and Lehrer, "Cationic peptides: a new source of antibiotics," *Trends in Biotechnology*, 1998;16:82-88.

Helle et al., "Vectors for improved Tet repressor-dependent gradual gene induction or silencing in Staphylococcus aureus," *Microbiology*, Dec. 2011;157(12):3314 3323.

Hirt et al., "Characterization of the Pheromone Response of the Enterococcus faecalis Conjugative Plasmid pCF10: Compete Sequence and Comparative Analysis of the Transcriptional and Phenotypic Resposnes of pCF10-Containing Cells to Pheromone Induction," *J Bacteriology*, Feb. 2005;187(3):1044-1054.

Hoffmann et al., "Range of activity and metabolic stability of synthetic antibacterial glycopeptides from insects," *Biochim Biophys Acta*, 1999;1426:459-467.

Holo and Nes, "Chapter 19: Transformation of Lactococcus by electroporation," *Methods Mol Biol.*, 1995;47:195-199.

Humphrey et al., "Experimental Infection of Hamsters with Campylobacter jejuni," *J Infect Dis.*, Mar. 1985;151(3):485-493.

Hunter et al., "InterPro in 2011: new developments in the family and domain prediction database," *Nucleic Acids Research*, 2012; 40(10): D306-D312.

Huse et al., "Exploring microbial diversity and taxonomy using SSU rRNA hypervariable tag sequencing," *PLoS genetics*, Nov. 2008; 4(11): e1000255: 10 pgs.

Huycke et al., "Multiple-Drug Resistant Enterococci: The Nature of The pRoblem and An Agenda for the Future," *Emerg Infect Dis*, Apr.-Jun. 1998;4(2):239-249.

Ishii et al., "Presence and Growth of Naturalized Escherichia Coli in Temperate Soils from Lake Superior Watersheds," *Appl. Environ. Microbiol.*, Jan. 2006;72(1):612-621.

Jack et al., "Bacteriocins of Gram-positive bacteria," *Microbiol Molec Bio Rev*, Jun. 1995; 59(2):171-200.

Khandelia et al., "Driving engineering of novel antimicrobial peptides from simulations of peptide-micelle interactions," *Biochimica et Biophysica Acta (BBA)—Biomembranes*, Sep. 2006;1758(9):1224-1234.

Khandelia and Kaznessis, "Molecular dynamics investigation of the influence of anionic and zwitterionic interfaces on antimicrobial peptides' structure: implications for peptide toxicity and activity," *Peptides*, Jun. 2006;27(6):1192-1200.

Kim et al., "A xylose-inducible Bacillus subtilis integration vector and its application," *Gene*, 1996; 181(1/2): 71-76.

Kjos et al., "An extracellular loop of the mannose phosphotransferase system component IIC is responsible for specific targeting by class IIa bacteriocins," *J Bacteriol.*, Nov. 2010; 192(22): 5906-5913.

Kokryakov et al., "Protegrins: leukocyte antimicrobial peptides that combine features of corticostatic defensins and tachyplesins," *FEBS letters*, Jul. 26, 1993;327(2):231-236.

Kristich et al., "Development of a host-genotype-independent conterselectable marker and a high-frequency conjugative delivery system and their use in genetic analysis of Enterococcus faecalis", *Plasmid*, Mar. 2007;57(2):131-144.

Kuipers et al., "Quorum sensing-controlled gene expression in lactic acid bacteria," *Journal of Biotechnology*, Sep. 17, 1998;64(1):15-21.

Langham et al., "On the nature of antimicrobial activity: a model for protegrin-1 pores," *Journal of the American Chemical Society*, Apr. 2, 2008;130: 4338-4346.

Langham and Kaznessis, "Effects of mutations on the C-terminus of protegrin-1: a molecular dynamics simulation study," *Molecular Simulation*, Mar.-Apr. 2006;32(3-4):193-201.

Langham et al., "Correlation between simulated physicochemical properties and hemolycity of protegrin-like antimicrobial peptides: predicting experimental toxicity," *Peptides*, Jul. 2008;29(7):1085-1093.

Lazarevic et al., "Metagenomic study of the oral microbiota by Illumina high-throughput sequencing," *Journal of Microbiol Methods*, 2009;79: 266-271.

Le Loir et al., "Signal peptide and propeptide optimization for heterologous protein secretion in Lactococcus lactis," *Appl Environ, Microbiol*, Sep. 2001;67(9):4119-4127.

Li, Y. "Recombinant production of antimicrobial peptides in Escherichia coli: a review," *Protein Expression and Purification*, Dec. 2011;80(2):260-267.

Ljungh et al., "Lactic acid bacteria as probiotics" *Curr Issues Intest Microbiol*, Sep. 2006; 7(2):73-89.

(56) References Cited

OTHER PUBLICATIONS

Lodemann et al., "Effects of Enterococcus faecium NCIMB 10415 as probiotic supplement on intestinal transport and barrier function of piglets," *Arch. Anim. Nutr.*, Feb. 2006;60(1):35-48.

Lohans and Verderas, "Development of Class IIa Bacteriocins as Therapeutic Agents," *Intl J Microbiol*, Oct. 8, 2011;2012(386410): 13 pgs.

Ludwig et al., "ARB: a software environment for sequence data," *Nucleic Acids Research*, 2004; 32(4): 1363-1371.

Lu et al., "Isolation, identification, and characterization of small bioactive peptides from Lactobacillus GG conditional media that exert both anti-Gram-negative and Gram-positive bactericidal activity," *J. Pediatr. Gastroenterol. Nutr.*, Jul. 2009;49(1):23-30.

Lyra et al., "Effect of a multispecies probiotic supplement on quantity of irritable bowel syndrome-related intestinal microbial phylotypes," *BMC Gastroenterol.*, 2010;10:110: 10 pgs.

Makarova, "Comparative genomics of the lactic acid bacteria," *PNAS U.S.A.*, Oct. 17, 2006;103(42): 15611-1561,.

Markowitz et al., "IMG: the integrated microbial genomes database and comparative analysis system," *Nucleic Acids Research*, Jan. 2012; 40(D1): D115-D122.

Marr et al., "Antibacterial peptides for therapeutic use: obstacles and realistic outlook," *Curr Opin. Pharm.*, Oct. 2006;6(5):468-472.

McBride et al., "Genetic Diversity among *Enterococcus faecalis*," *PLoS One*, Jul. 2007;7:e582:22 pgs.

McCormick et al., "Colicin V can be produced by lactic acid bacteria," *Lett Appl. Microbiol.*, Jul. 1999;29(1):37-41.

McNulty et al., "The impact of a consortium of fermented milk strains on the gut microbiome of gnotobiotic mice and monozygotic twins," *Science Translational Medicine*, Oct. 26, 2011;3(106):106ra106-106ra106.

Mellon et al., "*Hogging it: estimates of antimicrobial abuse in Livestock*," Union of Concerned Scientists, Cambridge MA, Jan. 2001: 14 pgs.

Mierau et al., "10 years of the nisin-controlled gene expression system (NICE) in Lactococcus lactis" Appl Microbiol Biotechnol, Oct. 2005; 68(6):705-17. Epub Oct. 13, 2005.

Mills et al., "New developments and applications of bacteriocins and peptides in foods," *Annual Review of Food Science and Technology*, 2011;2:299-329.

Miyoshi et al., "Controlled production of stable heterologous proteins in Lactococcus lactis," *Appl. Environ. Microbiol.*, Jun. 2002; 68(6): 3141-3146.

Mkrtchyan et al., "Purification, characterisation and identification of acidocin LCHV, an antimicrobial peptide produced by Lactobacillus acidophilus nv Er 317/402 strain Narine," *International Journal of Antimicrobial Agents*, 2010; 35, 255-260.

Munoz et al., "Native and heterologous production of bacteriocins from Gram-positive microorganisms," *Recent Pat. Biotechnol.*, 2011;5:199-211.

Nakayama et al., "The prgQ Gene of the *Enterococcus faecalis* Tetracycline Resistance Plasmid pCF10 Encodes a Peptide Inhibitor, iCF10," *J Bacteriol.*, Dec. 1994;176(23):7405-7408.

National Center for Biotechnology Information, National Library of Medicine, National Institutes of Health, GenBank Locus AB374546, Accession No. AB374546.1, "Enterococcus faecalis plasmid pMG2200 DNA, complete sequence" [online]. Bethesda, MD [retrieved on Mar. 10, 2016]. Retrieved from the Internet: <URL:http://www.ncbi.nlm.nih.gov/nuccore/AB374546>; 46pgs.

National Center for Biotechnology Information, National Library of Medicine, National Institutes of Health, GenBank Locus AB563188. 1, Accession No. AB563188.1, "Enterococcus faecalis plasmid pTW9 DNA, complete sequence" [online]. Bethesda, MD [retrieved on Mar. 10, 2016]. Retrieved from the Internet: <URL:http://www.ncbi.nlm.nih.gov/nuccore/AB563188.1>; 38 pgs.

National Center for Biotechnology Information, National Library of Medicine, National Institutes of Health, GenBank Locus AE002565, Accession No. AE002565.1, "Enterococcus faecalis plasmid pAM373, complete sequence," [online]. Bethesda, MD [retrieved on Mar. 10, 2016]. Retrieved from the Internet: <URL:http://www.ncbi.nlm.nih.gov/nuccore/AE002565>; 21 pgs.

National Center for Biotechnology Information, National Library of Medicine, National Institutes of Health, GenBank Locus AF005726. 1, Accession No. AF005726, "Enterococcus faecium enterocin P precursor (entP) and putative bacteriocin immunity protein genes, complete cds," [online]. Bethesda, MD [retrieved on Mar. 10, 2016]. Retrieved from the Internet: <URL: http://www.ncbi.nlm.nih.gov/nuccore/AF005726.1>;2 pgs.

National Center for Biotechnology Information, National Library of Medicine, National Institutes of Health, GenBank Locus AF240561. 1, Accession No. AF240561, "Enterococcus faecium class IIa bacteriocin EntA (entA) and putative immunity protein EntI (entI) genes, complete cds," [online]. Bethesda, MD [retrieved on Mar. 10, 2016]. Retrieved from the Internet: <URL: http://www.ncbi.nlm.nih.gov/nuccore/AF240561>; 2 pgs.

National Center for Biotechnology Information, National Library of Medicine, National Institutes of Health, GenBank Locus D28859, Accession No. D28859.1, "Enterococcus faecalis Plasmid pPd1 DNA for iPD1, TraB, TraA, ORF1 and TraC, complete cds," [online]. Bethesda, MD [retrieved on Mar. 10, 2016]. Retrieved from the Internet: <URL:http://www.ncbi.nlm.nih.gov/nuccore/D28859>; 4 pgs.

National Center for Biotechnology Information, National Library of Medicine, National Institutes of Health, GenBank Locus DQ664500. 1, Accession No. DQ664500, "Enterococcus hirae hiracin JM79 operon, complete sequence; putative mobilization protein and relaxase/mobilization nuclease domain protein genes, complete cds; and hypothetical protein gene, partial cds." [online]. Bethesda, MD [retrieved on Mar. 10, 2016]. Retrieved from the Internet: <URL: http://www.ncbi.nlm.nih.gov/nuccore/DQ664500.1>; 3 pgs.

Ng et al., "Engineering signal peptides for enhanced protein secretion from Lactococcus lactis," *Appln Environ Microbiol*, Jan. 2013;79(1):347-356.

Ng et al., "Nisin-inducible secretion of a biologically active single-chain insulin analog by Lactococcus lactis NZ9000," *Biotechnol. Bioeng.*, Aug. 2011;108(8):1987-1996.

Nilsson et al., "Chemical synthesis of proteins," *Annu. Rev. Biophys. Biomol. Struct.*, 2005;34:91-118.

O'Brien et al., "Colicin 24, a new plasmid-borne colicin from a uropathogenic strain of *Escherichia coli*," *Plasmid*, May 1994; 31(3): 288-296.

Oelschlaeger et al., "Mechanisms of probiotic actions—A review," *Intl. J. Med. Microbiol.*, 2010;300:57-62.

Ostberg and Kaznessis, "Protegrin structure—activity relationships: using homology models of synthetic sequences to determine structural characteristics important for activity," *Peptides*, Feb. 2005;26(2):197-206.

O'Sullivan et al., "Potential of bacteriocin-producing lactic acid bacteria for improvements in food safety and quality," *Biochimie*, May/Jun. 2002;84: 593-604.

Papagianni et al., "Pediocins: The bacteriocins of Pediococci. Sources, production, properties and applications," *Microb Cell Fact.*, 2009;8:3: 16 pgs.

Percival et al., "Choosing a probiotic supplement," *Clin. Nutr. Insights*, 1997;6(1):1-4.

Proença et al., "Phage Endolysins with Broad Antimicrobial Activity against Enterococcus faecalis Clinical Strains," *Microb Drug Resist*, 2012;18(3):322-332.

Pruesse et al., "SILVA: a comprehensive online resource for quality checked and aligned ribosomal RNA sequence data compatible with ARB," *Nucleic Acids Research*, Dec. 2007; 35(21): 7188-7196.

Puigbò, et al., "OPTIMIZER: a web server for optimizing the codon usage of DNA sequences," *Nucleic Acids Research*, 2007; 35(Suppl 2): W126-W131.

Qu et al., "Protegrin structure and activity against Neisseria gonorrhoeae," *Infect Immun*, Feb. 1997;65(2):636-639.

Robertson et al., "Diversity and stratification of archaea in a hypersaline microbial mat," *Appl Environ Microbiol*, Apr. 2009; 75(7): 1801-1810.

Rodriguez-Rubio et al., "Lytic activity of LysH5 endolysin secreted by Lactococcus lactis using the secretion signal sequence of bacteriocin Lcn972," *Appl. Environ. Microbiol.*, May 2012;78(9):3469-3472.

(56) References Cited

OTHER PUBLICATIONS

Rud et al., "A synthetic promoter library for constitutive gene expression in Lactobacillus plantarum," *Microbiology*, 2006;152, 1011-1019.
Ruhfel et al., "Cloning and characterization of a region of the Enterococcus faecalis conjugative plasmid, pCF10 encoding a sex pheromone-binding function," *J Bacteriol*, Aug. 1993;175(16):5253-5259.
Ruiz-Palacios, "Experimental *Campylobacter* Diarrhea in Chickens," *Infect Immun.*, Oct. 1981;34(1):250-255.
Sambrook et al., "Molecular Cloning: a Laboratory Manual," 2nd Ed. Cold Spring Harbor Laboratory Press, Cold Spring Harbor, NY, 1989, Copyright page, Table of Contents Only.
Sanchez et al., "Amino acid and nucleotide sequence, adjacent genes, and heterologous expression of hiracin JM79, a sec-dependent bacteriocin produced by *Enterococcus hirae* DCH5, isolated from Mallard ducks (*Anas platyrhynchos*)," *FEMS Microbiol Lett*, May 2007;270(2):227-236.
Seo et al., Elimination of early *Salmonella enteritidis* infection after treatment with competitive-exclusion culture and enrofloxacin in experimentally infected chicks, *Poultry Science*, Oct. 2000; 79(10): 1408-1413.
Sogin et al., "Microbial diversity in the deep sea and the underexplored rare biosphere," *PNAS*, Aug. 8, 2006;103(32): 12115-12120.
Son et al., "Complete genome sequence of a newly isolated lytic bacteriophage, EFAP-1 of *Enterococcus faecalis*, and antibacterial activity of its endolysin EFAL-1," *J Appl Microbiol.*, May 2010;108(5):1769-1779.
Sorvig, "Construction of vectors for inducible gene expression in Lactobacillus sakei and L. plantarum" 2003 *FEMS Microbiology Letters*, 229: 119-126.
Stammen et al., "High-yield intra-and extracellular protein production using Bacillus megaterium," *Appl Environ Microbiol.*, Jun. 2010;76(12):4037-4046.
Stanfield et al., "*Campylobacter* diarrhea in an adult mouse model," *Microb Pathog.*, Sep. 1987;3(3):155-165.
Subramanian et al., "Gene set enrichment analysis: a knowledge-based approach for interpreting genome-wide expression profiles," *PNAS USA*, Oct. 25, 2005;102(43): 15545-15550.
Szabo et al., The designer proline-rich antibacterial peptide A3-APO is effective against systemic *Escherichia coli* infections in different mouse models, *International Journal of Antimicrobial Agents*, Apr. 2010;35(4):357-361.
Tamamura et al., "Synthesis of protegrin-related peptides and their antibacterial and anti-human immunodeficiency virus activity," *Chemical & Pharmaceutical Bulletin*, May 1995;43(5):853.
Tanabe et al., "Using the KEGG Database Resource," *Current Protocols in Bioinformatics*, Jun. 2012; 38:1.12.1-1.12.43.
Tatusov et al., "The COG database: a tool for genome-scale analysis of protein functions and evolution," *Nucleic Acids Research*, Jan. 2000;28(1), 33-36.
Todorov et al., "Probiotic properties of Lactococcus lactis ssp. lactis HV219, isolated from human vaginal secretions," *J. Appl. Microbiol.*, Sep. 2007; 103(3): 629-639.

Uchiyama et al., "Characterization of Lytic Enzyme Open Reading Fraom 9 (ORF9) Derived from Enterococcus faecalis Bacteriophage EF24C," *Appl Enviorn Microbiol.*, Jan. 2011;77(2):580-585.
Van Asseldonk et al., "Cloning of usp45, a gene encoding a secreted protein from Lactococcus lactis subsp. lactis MG1363," *Gene*, 1990;95:155-160.
Van de Guchte et al., "Construction of a lactococcal expression vector: expression of hen egg white lysozyme in Lactococcus lactis subsp. lactis.," *Appl. Environ. Microbiol.*, Jan. 1989;55(1):224-228.
Van der Vossen et al., "Isolation and Characterization of *Streptococcus cremoris* Wg2-Specific Promoters," *Appl Environ Microbiol.*, Oct. 1987;53(10):2452-2457.
Volzing et al., "Antimicrobial Peptides Targeting Gram-negative Pathogens, Produced and Delivered by Lactic Acid Bacteria," *ACS ChemBiol*, 2011;6:1107-1116.
Volzing et al., "ProTeOn and ProTeOff, new protein devices that inducibly activate bacterial gene expression," *ACS Chem Biol*, Oct. 21, 2011;6(10):1107-1116.
Wardal et al., "Complex Nature of Enterococcal Pheromone-Responsive Plasmids," *Polish Journal of Microbiology*, 2010;59(2):79-87.
Whitley et al., "Use of a commercial probiotic supplement in meat goats," *J Anim Sci*, Feb. 2009;87(2):723-728.
Wirth et al., "The sex pheromone system of *Enterococcus faecalis* More than just a plasmid-collection mechanism?" *Euro J Biochem*, 1994;222:235-246.
Witte, "Medical consequences of antibiotic use in agriculture," *Science*, Feb. 13, 1998;279:996-997.
Wood et al., "Host specificity of DNA produced by *Escherichia coli*: bacterial mutations affecting the restriction and modification of Dna," *J Mol. Biol.*, Mar. 1966;16(1):118-33.
Xiao, "Identification and Functional Characterization of Three Chicken Cathelicidins with Potent Antimicrobial Activity," *Journal of Biological Chemistry*, Feb. 3, 2006;281(5): 2858-2867.
Yan and Gilbert, "Antimicrobial drug delivery in food animals and microbial food safety concerns: an overview of in vitro and in vivo factors potentially affecting the animal gut microflora," *Adv Drug Deliv. Rev*, Jun. 23, 2004;56(10):1497-1521.
Yanisch-Perron et al., "Improved M13 phage cloning vectors and host strains: nucleotide sequences of the M13mp18 and pUC19 vectors," *Gene*, 1985;33(1):103-119.
Yansura and Henner, "Use of the *Escherichia coli* lac repressor and operator to control gene expression in Bacillus subtilis," *PNAS*, Jan. 15, 1984;81(2): 439-443.
Yoong et al., "Identification of a Broadly Active Phage Lytic Enzyme with Lethal Activity against Antibiotic-Resistant *Enterococcus faecalis* and *Enterococcus faecium*," *J Bacteriol*, Jul. 2004;186(14):4808-4812.
Zheng, "Isolation of VanB-Type Enterococcus faecalis Strains from Nosocomial Infections: First Report of the Isolation and Identification of the Pheromone-Responsive Plasmids pMG2200, Encoding VanB-Type Vancomycin Resistance and a Bac41-Type Bacteriocin, and pMG2201" Feb. 2009 *Antimicrob. Agent & ChemoTherap.*, 53:735-74.

FIG. 2
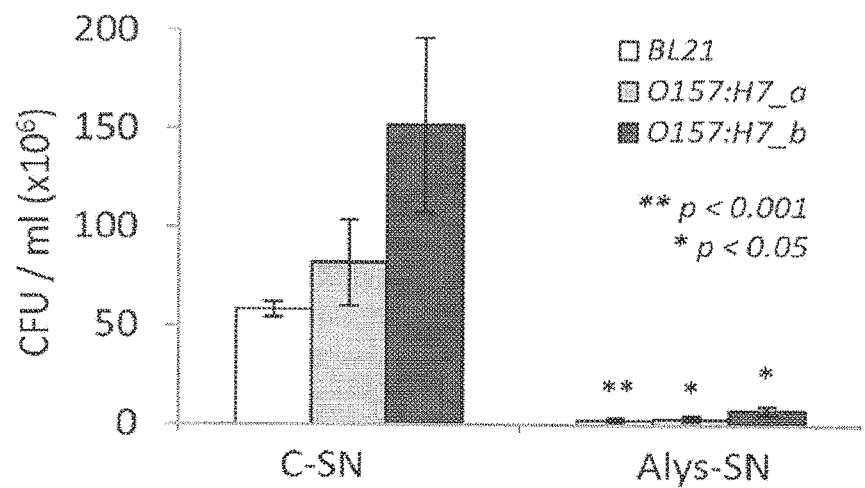
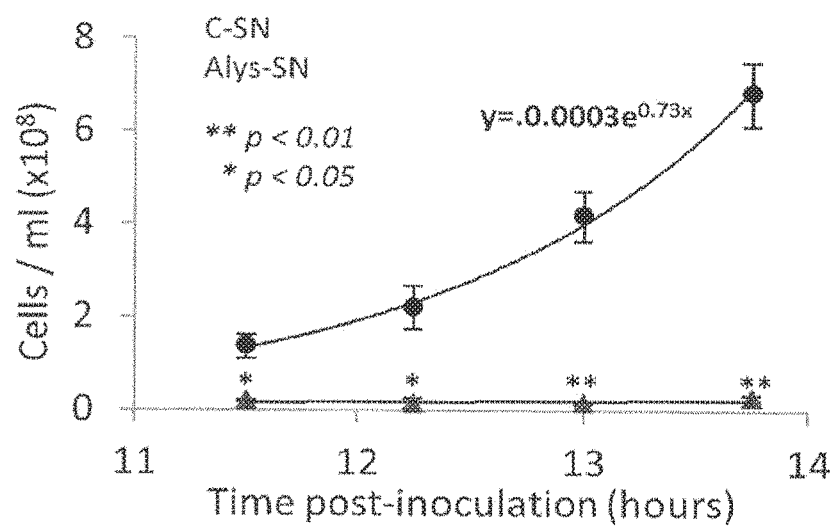

FIG. 3
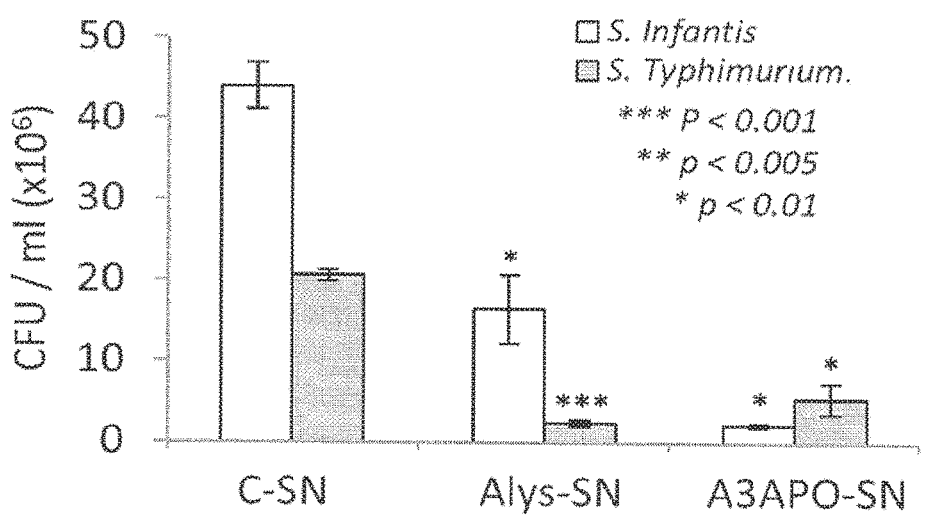
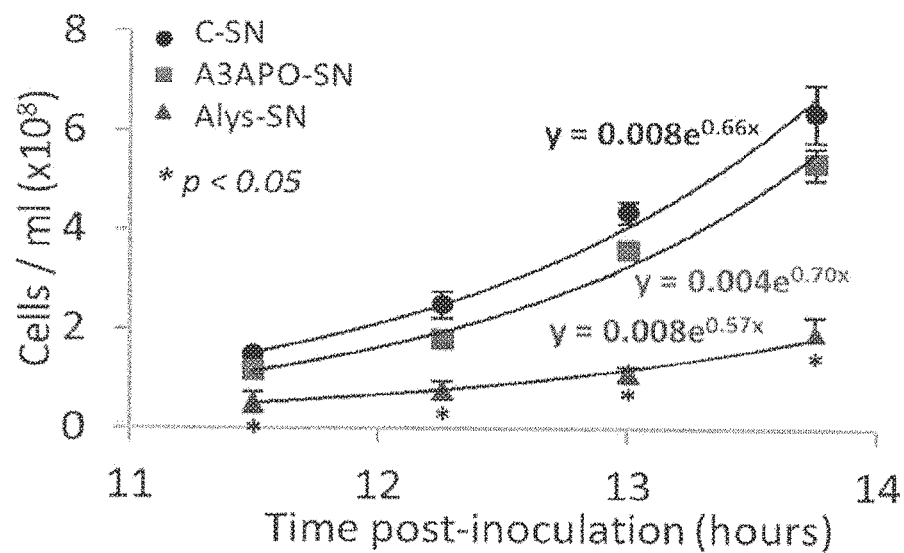

Fig. 5B-1

```
1     attttgttgg tggcttggaa atgtttaggc accttatata ataaaaaata aaagagcagt
61    catgaaaata ttttcatgac tgctctttta tttcaggaat aggattattt tctattgcaa
                             |<- - - - - - - - - - - - - - - - - - - -
121   cgtaattttc ataatacatg gttacttctt taggggcgt aaattttct tttgcagata
      <- - - - - - - - - - - - - - - - - - - - - - - - - - - - - - - -
181   tttttgtaag ttcctcaact aaagatctgt gaatatcttc ttttccaatg attttaaaga
      <- - - - - - - - - - - - - - - - - - - - - - - - - - - - - - - -
241   tgttgataat atttaccgca tttaaataag aatcaatatt tttgtcagtt aaaaattgat
      <- - - - - - - - - - - - - - - - - - - - - - - - - - - - - - - -
301   atatttgttt taaatagttt atttctaagt cgtaatatcc atttatgcta atatttttaa
      <- - - - - - - - - - - - - - - - - - - - - - - - - - - - - - - -
361   ttgtttttaa gtgttcaaat tgattaatat aatactgcgc ttcttttaga tttctattca
      <- - - - - - - - - - - - - - - - - - - - - - - - - - - - - - - -
421   taattgatat tgttaaagca tttttagaa cagtctgaat agttaaatcg taatctttac
      <- - - - - - - - - - - - - - - - - - - - - - - - - - - - - - - -
481   caaggaatc cacgattgga tacataggct taatgatact tgaaacttct tcatacggta
      <- - - - - - - - - - - - - - - - - - - - - - - - - - - - - - - -
541   agacatttaa aagatttgaa acaatttcat aatcaattcc aaaaaatgtt gttcttttat
      <- - - - - - - - - - - - - - - - - - - - - - - - - - - - - - - -
601   catataaatg ttttaaatct gaagtaattg ttttattaaa agtaggaact tcaatgttat
      <- - - - - - - - - - - - - - - - - - - - - - - - - - - - - - - -
661   aatgatgtgc aatagaaata tatccaagat aaatactaaa gtactgaaga ctagttaagc
      <- - - - - - - - - - - - - - - - - - - - - - - - - - - - - - - -
721   gctttggctc aatcctttga aaattttgt caaataagtc agggtttgta aatattttg
      <- - - - - - - - - - - - - - - - - - - - - - - - - - - - - - - -
781   aaataagaag ttttctttt cctgttcat ttacgctttt tgtattcatg ccagctctat
      <- - - - - - - - - - - - - - - - - - - - - - - - - - - - - - - -
841   ttaaaattc aaaaaattt acacctaaac gttctgagaa cttgcttaac tcttctacag
      <- - - - - - - - - - - - - - - - - - - - - - - - - - - - - - - -
901   aaatcggtcg agagtcagct tcaactttta tgtaaacaga tttggacatt attccagaat
      <- - - - - - - - - - - - - - - - - - - - - - - - - - - - - - - -
961   ataaatcaat ctgatggtaa tttaactctt gccttatttg tttcaggaca gaacctatct
      <- - - - - - - - - - - - - - - - - - - - - - - - - - - - - - - -
1021  taaacatttt cttcctccta atatctcgag tatcaaaaag tagacctaaa attcgataaa
      <- - - -| prgX
1081  ctacaaaaat ttgttaatat tttaatttta ggtattgaat acgacactcg aagatgtgtt
1141  tattaagcta tatccctttt ttttaaaaaa aaatacatat tttagttgaa aatataatac
1201  ttagatgtta agatgttttt ataggagggg tgtaaatgaa aaccactcta aaaaactat
                                              prgQ |- - - - - - - - - - - - ->
1261  caagatatat agctgttgta attgcaataa ccttaatatt tatctgatag aaaaaatcat
      - - - - - - - - - - - - - - - - - - - - - - - - - - - - - ->|
1321  agtaacaatt aaacaaatta agaaccgact gccataggac ggcaatccta ggggcagtt
1381  aaacaattca tggtatgaca tgaactctac tcggttctcg tttgttgcaa cattagttac
1441  aacgtatagt ataacaattt tttatgtaaa attctagact ttttaaact cctttatttg
1501  tctaggaaaa gtttttacag tgaattgttt ttattagttg tataaatgtt ggagcagcgg
```

Fig. 5B-2

```
1561  ggaatgtata cagttcatgt atatgttccc cgcttttttt gttgtctgtt gggggatcca
                                                                  BamHI
1621  aaaggaggag aaaactacta tggaagttac tgacgtaaga ttacgggtcg accgggaaaa
                             lacZ
1681  ccctggcgtt acccaactta atcgccttgc agcacatccc cctttcgcca gctggcgtaa
1741  tagcgaagag gcccgcaccg atcgcccttc ccaacagttg cgcagcctga atggcgaatg
1801  gcgctttgcc tggtttccgg caccagaagc ggtgccggaa agctggctgg agtgcgatct
1861  tcctgaggcc gatactgtcg tcgtccctc aaactggcag atgcacggtt acgatgcgcc
1921  catctacacc aacgtaacct atcccattac ggtcaatccg ccgtttgttc ccacggagaa
1981  tccgacgggt tgttactcgc tcacatttaa tgttgatgaa agctggctac aggaaggcca
2041  gacgcgaatt attttttgatg gcgttaactc ggcgtttcat ctgtggtgca acgggcgctg
2101  ggtcggttac ggccaggaca gtcgtttgcc gtctgaattt gacctgagcg cattttacg
2161  cgccggagaa aaccgcctcg cggtgatggt gctgcgttgg agtgacggca gttatctgga
2221  agatcaggat atgtggcgga tgagcggcat tttccgtgac gtctcgttgc tgcataaacc
2281  gactacacaa atcagcgatt ccatgttgc cactcgcttt aatgatgatt tcagccgcgc
2341  tgtactggag gctgaagttc agatgtgcgg cgagttgcgt gactacctac gggtaacagt
2401  ttctttatgg cagggtgaaa cgcaggtcgc cagcggcacc gcgcctttcg gcggtgaaat
2461  tatcgatgag cgtggtggtt atgccgatcg cgtcacacta cgtctgaacg tcgaaaaccc
2521  gaaactgtgg agcgccgaaa tcccgaatct ctatcgtgcg gtggttgaac tgcacaccgc
2581  cgacggcacg ctgattgaag cagaagcctg cgatgtcggt ttccgcgagg tgcggattga
2641  aaatggtctg ctgctgctga acggcaagcc gttgctgatt cgaggcgtta accgtcacga
2701  gcatcatcct ctgcatggtc aggtcatgga tgagcagacg atggtgcagg atatcctgct
2761  gatgaagcag aacaacttta cgccgtgcg ctgttcgcat tatccgaacc atcgctgtg
2821  gtacacgctg tgcgaccgct acggcctgta tgtggtggat gaagccaata ttgaaaccca
2881  cggcatggtg ccaatgaatc gtctgaccga tgatccgcgc tggctaccgg cgatgagcga
2941  acgcgtaacg cgaatggtgc agcgcgatcg taatcacccg agtgtgatca tctggtcgct
3001  ggggaatgaa tcaggccacg gcgctaatca cgacgcgctg tatcgctgga tcaaatctgt
3061  cgatccttcc cgcccggtgc agtatgaagg cggcggagcc gacaccacgg ccaccgatat
3121  tatttgcccg atgtacgcgc gcgtggatga agaccagccc ttcccggctg tgccgaaatg
```

Fig. 5B-3

```
3181  gtccatcaaa aaatggcttt cgctacctgg agagacgcgc ccgctgatcc tttgcgaata
3241  cgcccacgcg atgggtaaca gtcttggcgg tttcgctaaa tactggcagg cgtttcgtca
3301  gtatccccgt ttacagggcg gcttcgtctg ggactgggtg gatcagtcgc tgattaaata
3361  tgatgaaaac ggcaacccgt ggtcggctta cggcggtgat tttggcgata cgccgaacga
3421  tcgccagttc tgtatgaacg gtctggtctt tgccgaccgc acgccgcatc cagcgctgac
3481  ggaagcaaaa caccagcagc agttttttcca gttccgttta tccgggcaaa ccatcgaagt
3541  gaccagcgaa tacctgttcc gtcatagcga taacgagctc ctgcactgga tggtggcgct
3601  ggatggtaag ccgctggcaa gcggtgaagt gcctctggat gtcgctccac aaggtaaaca
3661  gttgattgaa ctgcctgaac taccgcagcc ggagagcgcc gggcaactct ggctcacagt
3721  acgcgtagtg caaccgaacg cgaccgcatg gtcagaagcc gggcacatca gcgcctggca
3781  gcagtggcgt ctggcggaaa acctcagtgt gacgctcccc gccgcgtccc acgccatccc
3841  gcatctgacc accagcgaaa tggattttg catcgagctg gtaataagc gttggcaatt
3901  taaccgccag tcaggctttc tttcacagat gtggattggc gataaaaaac aactgctgac
3961  gccgctgcgc gatcagttca cccgtgcacc gctggataac gacattggcg taagtgaagc
4021  gacccgcatt gaccctaacg cctgggtcga acgctggaag gcggcgggcc attaccaggc
4081  cgaagcagcg ttgttgcagt gcacggcaga tacacttgct gatgcggtgc tgattacgac
4141  cgctcacgcg tggcagcatc aggggaaaac cttatttatc agccggaaaa cctaccggat
4201  tgatggtagt ggtcaaatgg cgattaccgt tgatgttgaa gtggcgagcg atacaccgca
4261  tccggcgcgg attggcctga actgccagct ggcgcaggta gcagagcggg taaactggct
4321  cggattaggg ccgcaagaaa actatcccga ccgccttact gccgcctgtt ttgaccgctg
4381  ggatctgcca ttgtcagaca tgtatacccc gtacgtcttc ccgagcgaaa acggtctgcg
4441  ctgcgggacg cgcgaattga attatggccc acaccagtgg cgcggcgact tccagttcaa
4501  catcagccgc tacagtcaac agcaactgat ggaaaccagc catcgccatc tgctgcacgc
4561  ggaagaaggc acatggctga atatcgacgg tttccatatg gggattggtg gcgacgactc
4621  ctggagcccg tcagtatcgg cggaattaca gctgagcgcc ggtcgctacc attaccagtt
4681  ggtctggtgt caaaaataat aataagaatt ccttaaggaa cgtacagacg cttaaaagc
                                    EcoRI
4741  ctttaaaaac gtttttaagg ggtttgtaga caaggtaaag gataaaacag cacaattcca
```

Fig. 5B-4

```
4801  agaaaaacac gatttagaac ctaaaagaa cgaatttgaa ctaactcata accgagaggt
4861  aaaaaaagaa cgaagtcgat tttttattaa aacgtctcaa aatcgtttct gagacgtttt
4921  agcgtttatt tcgtttagtt atcggcataa tcgttaaaac aggcgttatc gtagcgtaaa
4981  agcccttgag cgtagcgtgg ctttgcagcg aagatgttgt ctgttagatt atgaaagccg
5041  atgactgaat gaaataataa gcgcagcgtc cttctatttc ggttggagga ggctcaaggg
5101  agtttgaggg aatgaaattc cctcatgggt ttgattttaa aaattgcttg caattttgcc
5161  gagcggtagc gctggaaaat ttttgaaaaa aatttggaat ttggaaaaaa atgggggaa
5221  aggaagcgaa ttttgcttcc gtactacgac cccccattaa gtgccgagtg ccaatttttg
5281  tgccaaaaac gctctatccc aactggctca agggtttgag gggttttca atcgccaacg
5341  aatcgccaac gttttcgcca acgttttta taaatctata tttaagtagc tttattgttg
5401  ttttatgatt acaaagtgat acactaattt tataaaatta tttgattgga gttttttaaa
5461  tggtgatttc agaatcgaaa aaaagagtta tgatttctct gacaaaagag caagataaaa
5521  atttaggagg catatcaaat gaactttaat aaaattgatt tagacaattg aagagaaaa
               cat ⊢ ─ ─ ─ ─ ─ ─ ─ ─ ─ ─ ─ ─ ─ ─ ─ ─ ─ ─ ─ ─ ─ ─ ─ ─ ─ ─ →
5581  gagatattta atcattattt gaaccaacaa acgacttta gtataaccac agaaattgat
      ─ ─ ─ ─ ─ ─ ─ ─ ─ ─ ─ ─ ─ ─ ─ ─ ─ ─ ─ ─ ─ ─ ─ ─ ─ ─ ─ ─ ─ →
5641  attagtgttt tataccgaaa cataaaacaa gaaggatata aatttaccc tgcatttatt
      ─ ─ ─ ─ ─ ─ ─ ─ ─ ─ ─ ─ ─ ─ ─ ─ ─ ─ ─ ─ ─ ─ ─ ─ ─ ─ ─ ─ ─ →
5701  ttcttagtga caagggtgat aaactcaaat acagctttta gaactggtta caatagcgac
      ─ ─ ─ ─ ─ ─ ─ ─ ─ ─ ─ ─ ─ ─ ─ ─ ─ ─ ─ ─ ─ ─ ─ ─ ─ ─ ─ ─ ─ →
5761  ggagagttag gttattggga taagttagag ccactttata caatttttga tggtgtatct
      ─ ─ ─ ─ ─ ─ ─ ─ ─ ─ ─ ─ ─ ─ ─ ─ ─ ─ ─ ─ ─ ─ ─ ─ ─ ─ ─ ─ ─ →
5821  aaaacattct ctggtatttg gactcctgta aagaatgact tcaaagagtt ttatgattta
      ─ ─ ─ ─ ─ ─ ─ ─ ─ ─ ─ ─ ─ ─ ─ ─ ─ ─ ─ ─ ─ ─ ─ ─ ─ ─ ─ ─ ─ →
5881  tacctttctg atgtagagaa atataatggt tcggggaaat tgtttcccaa acacctata
      ─ ─ ─ ─ ─ ─ ─ ─ ─ ─ ─ ─ ─ ─ ─ ─ ─ ─ ─ ─ ─ ─ ─ ─ ─ ─ ─ ─ ─ →
5941  cctgaaaatg cttttctct ttctattatt ccatgtactt catttactgg gtttaactta
      ─ ─ ─ ─ ─ ─ ─ ─ ─ ─ ─ ─ ─ ─ ─ ─ ─ ─ ─ ─ ─ ─ ─ ─ ─ ─ ─ ─ ─ →
6001  aatatcaata ataatagtaa ttaccttcta cccattatta cagcaggaaa attcattaat
      ─ ─ ─ ─ ─ ─ ─ ─ ─ ─ ─ ─ ─ ─ ─ ─ ─ ─ ─ ─ ─ ─ ─ ─ ─ ─ ─ ─ ─ →
6061  aaaggtaatt caatatattt accgctatct ttacaggtac atcattctgt tgtgatggt
      ─ ─ ─ ─ ─ ─ ─ ─ ─ ─ ─ ─ ─ ─ ─ ─ ─ ─ ─ ─ ─ ─ ─ ─ ─ ─ ─ ─ ─ →
6121  tatcatgcag gattgtttat gaactctatt caggaattgt cagataggcc taatgactgg
      ─ ─ ─ ─ ─ ─ ─ ─ ─ ─ ─ ─ ─ ─ ─ ─ ─ ─ ─ ─ ─ ─ ─ ─ ─ ─ ─ ─ ─ →
6181  cttttataat atgagataat gccgactgta cttttacag tcggttttct aacgatacat
      ─ ─ ─⇥
6241  taataggtac gaaaaagcaa ctttttttgc gcttaaaacc agtcatacca ataacttaag
6301  ggtaactagc ctcgccggaa agagcgaaaa tgcctcacat ttgtgccacc taaaaaggag
6361  cgatttacat atgagttatg cagtttgtag aatgcaaaaa gtgaaatcag ctagatatat
```

Fig. 5B-5

```
6421  agtgccgtct aattttgta tcaaatcact atctaattta gatacttgat aatgaatttt
6481  cttttttgat acgcccaact catcagccaa ctctttaatc gttttaagt tctcactcat
                                                                    |<- -
6541  ggtttaagtc ctgccttta accgtaggta gatattgctc gattgctttt ttcagatact
      <- - - - - - - - - - - - - - - - - - - - - - - - - - - - - - - - -
6601  tcgctacatt gcgtttagaa taggcttctt ttttgctaga tatataagac aagtggtctt
      <- - - - - - - - - - - - - - - - - - - - - - - - - - - - - - - - -
6661  tgacccatt caatcctctt aattccttta actcgtcata caacggatag acgttctttt
      <- - - - - - - - - - - - - - - - - - - - - - - - - - - - - - - - -
6721  gcaaacctgc cataagtgcc gtgtccgtca tttcaagagg ggataagaga aagttttcaa
      <- - - - - - - - - - - - - - - - - - - - - - - - - - - - - - - - -
6781  tcaataatcg tgtgtacttg ctttccattg cctgttttaa taagtcagct tcatttcttg
      <- - - - - - - - - - - - - - - - - - - - - - - - - - - - - - - - -
6841  attttcctc tttgtcggat tgataatctt tatcttctaa cttgtagctg ttatcatctg
      <- - - - - - - - - - - - - - - - - - - - - - - - - - - - - - - - -
6901  ctcgacgttt tttcgtgata tgaaagacaa tagaatcaat gcttcgtcct tttttatct
      <- - - - - - - - - - - - - - - - - - - - - - - - - - - - - - - - -
6961  tgtcatacgt cacgttaaaa gaggtgtttt cgttaatttc ttctattggt tcttttaaaa
      <- - - - - - - - - - - - - - - - - - - - - - - - - - - - - - - - -
7021  ctctatgttc taatctatca aagcgggggt attcatcaac tgtatccgtc atttctcgta
      <- - - - - - - - - - - - - - - - - - - - - - - - - - - - - - - - -
7081  attctcgcat tgaaatggta ggattgcggt aggcttccac ttgttcttct ctccgtccgc
      <- - - - - - - - - - - - - - - - - - - - - - - - - - - - - - - - -
7141  ccttataact ataatgctcg tattggttat aattcatgga taaccaacgg tacaagataa
      <- - - - - - - - - - - - - - - - - - - - - - - - - - - - - - - - -
7201  tagagtattt gctattcagc tctgcaatat cagacaaagc atgttgcgtg aaattttgtt
      <- - - - - - - - - - - - - - - - - - - - - - - - - - - - - - - - -
7261  ttagattaat taagtagggc atgatttcac gatgaaattc aattttacg tcatcatgat
      <- - - - - - - - - - - - - - - - - - - - - - - - - - - - - - - - -
7321  aatctgtcca ctcgacatat ggaatgggaa caatactcct aaatttaaat cctttaccta
      <- - - - - - - - - - - - - - - - - - - - - - - - - - - - - - - - -
7381  cttcttcttt aatttgaaaa aaggcttgtt tttgcatatt ctctactgct tgtttaaaac
      <- - - - - - - - - - - - - - - - - - - - - - - - - - - - - - - - -
7441  gactatgttt gtcattatca gataccttaa aaaaggcaaa caattcttct tttgagagat
      <- - - - - - - - - - - - - - - - - - - - - - - - - - - - - - - - -
7501  aaaccgtatg atctttgggt ggttcttcgg tattaataca agacacggct aattcaaaca
      <- - - - - - - - - - - - - - - - - - - - - - - - - - - - - - - - -
7561  ttttcagtgg cgttttatcc attttcgcaa tactggtaat taaagaatta tgttccacta
      <- - - - - - - - - - - - - - - - - - - - - - - - - - - - - - - - -
7621  cttttcgttt tgacaattcg ttcaaggttt gcacctgctt tgattaggt tcatttttg
      <- - - - - - - - - - - - - - - - - - - - - - - - - - - - - - - - -
7681  atatactaga catagaaaac tgctcctttg tgagtgagtt tagataagca tgaagaaaca
      <- - - - - - -| repB
7741  cttttcgtag agagattctt catgcttta ttatatcatt ataccaac gaaacaaaca
7801  aagaagttgg tatatgcaca gttttttgtt ggtgtatgca cagttttttg ttggtatata
7861  cacagttttt tgttggtata taattctata aagccttgaa atattgatt ttttttgac
7921  gcaaagaat aaaagattaa aatatataag ataaatatat aataggcttc gcctattttt
7981  tattttttc aaaaatttaa aaccaaggt caaagtcatc aaaaaaagga gtgagcgagt
```

Fig. 5B-6

```
8041  gaacgctcac attttacttg cagcgttcac tcgctaaaag aaaagatcaa aaccgctttt
8101  aggaatttat tggattccct ctaattgctc atataagctg ttttaactgt ttgactagct
8161  aaatactcat atcatgcaat caagcgtctt acagacggtc agggcaagcc ctaacaaccc
8221  ttaaatggaa aactgatact ttgtttaact tgttttttt acaacttaca acaagctatt
8281  caattcaaaa tcaatttaaa ccccttaaa agctcgttta agcattctta atgctccctt
8341  tgaacaaata gacagtttcg aattaaagtc gcttaaatcg agttttagaa cgttttaaaa
8401  tagaatgatg aaaaactaaa aagtttcaaa cgctggtcgg cttgtttcgt aaaaaaagag
8461  tgcaatgcgc acttacacat cactctaaaa acgagtgatg taatggctaa aaatcgtgta
8521  ttagaagttg cttatcacaa caacaaaatt tcatgatagt agcttctctt aaatgagtga
8581  gtctttgttt caatttgtga tacatttttc tgatccatca ataacttact caaagataaa
8641  atgcctcagc gctcattcct caatcgccct tgtcattga ttttgtaata agcattgcgc
8701  cctattcggt tacaatcctc acaacaaaat agaccatata aaccataaa tactgcaagc
8761  tatcacattg taatacaaaa cacttcgttc ttgtattaca atgtggcttg aaaagggga
8821  agtttcactt tcccctttta tcccctttgg attgtgtcga tttgctttac acaaacgcca
8881  cctgcccatt ttataaaaat aaaatgggca aaagatctgc ctcgcgcgtt tcggtgatga
8941  cggtgaaaac ctctgacaca tgcagctccc ggagacggtc acagcttgtc tgtaagcgga
9001  tgccgggagc agacaagccc gtcagggcgc gtcagcgggt gttggcgggt gtcggggcgc
9061  agccatgacc cagtcacgta gcgatagcgg agtgtatact ggcttaacta tgcggcatca
9121  gagcagattg tactgagagt gcaccatatg cggtgtgaaa taccgcacag atgcgtaagg
9181  agaaaatacc gcatcaggcg ctcttccgct tcctcgctca ctgactcgct gcgctcggtc
9241  gttcggctgc ggcgagcggt atcagctcac tcaaaggcgg taatacggtt atccacagaa
9301  tcaggggata acgcaggaaa gaacatgtga gcaaaaggcc agcaaaggc caggaaccgt
                                                              ColE1
9361  aaaaaggccg cgttgctggc gttttccat aggctccgcc cccctgacga gcatcacaaa
9421  aatcgacgct caagtcagag gtggcgaaac ccgacaggac tataaagata ccaggcgttt
9481  ccccctggaa gctccctcgt gcgctctcct gttccgaccc tgccgcttac cggatacctg
9541  tccgcctttc tcccttcggg aagcgtggcg ctttctcata gctcacgctg taggtatctc
9601  agttcggtgt aggtcgttcg ctccaagctg ggctgtgtgc acgaaccccc cgttcagccc
```

Fig. 5B-7

```
9661  gaccgctgcg ccttatccgg taactatcgt cttgagtcca acccggtaag acacgactta
9721  tcgccactgg cagcagccac tggtaacagg attagcagag cgaggtatgt aggcggtgct
9781  acagagttct tgaagtggtg cctaactac ggctacacta gaaggacagt atttggtatc
9841  tgcgctctgc tgaagccagt taccttcgga aaaagagttg gtagctcttg atccggcaaa
                                                                    ColE1
9901  caaaccaccg ctggtagcgg tggtttttt gtttgcaagc agcagattac gcgcagaaaa
9961  aaaggatctc aagaagatcc tttgatcttt tctacggggt ctgacgctca gtggaacgaa
10021 aactcacgtt aagggatttt ggtcatgaga ttatcaaaaa ggatcttcac ctagatcctt
10081 ttaaattaaa aatgaagttt taaatcaatc taaagtatat atgagtaaac ttggtctgac
10141 agttaccaat gcttaatcag tgaggcacct atctcagcga tctgtctatt tcgttcatcc
10201 atagttgcct gactcccgt cgtgtagata actacgatac gggagggctt accatctggc
10261 cccagtgctg caatgatacc gcgagaccca cgctcaccgg ctccagattt atcagcaata
10321 aaccagccag ccggaagggc cgagcgcaga agtggtcctg caactttatc cgcctccatc
10381 cagtctatta attgttgccg ggaagctaga gtaagtagtt cgccagttaa tagtttgcgc
10441 aacgttgttg ccattgctgc ag
                          PstI
```

Fig. 6-1

```
   1    ctgcaggaaa agccctgaca acgcttgttc ctaaaaagga ataagcgttc ggtcagtaaa
        ‾‾‾‾‾
        PstI
  61    taatagaaat aaaaaatcag acctaagact gatgacaaaa agagaaaatt ttgataaaat
 121    agtcttagaa ttaaattaaa aagggaggcc aaatataatg aaaaatatga atgacaatga
 181    tgttggtacc atccctttta aagtttattt gataaaattg taaatataat agctattaat
 241    tggttatttt atttgtatat cgctagaatt agttagcaaa tttaacctac ggaggttgat
 301    aaaaatgaag aagtacaaga agttttgttt tttaggtatt ggttattac ctttggtatt
        prgZ ├ ─ ─ ─ ─ ─ ─ ─ ─ ─ ─ ─ ─ ─ ─ ─ ─ ─ ─ ─ ─ ─ ─ ─ ─ ─ ─ ─→
 361    agctagttgt gggacaaata ctgccacaaa agattcacaa gatgcaacag aaaaaaaagt
 421    agaacaggta gcgactttga ctgcaggac acctgtccaa agtttagacc cagcaactgc
 481    tgtagatcaa acgagtataa ctttattagc caatgtgatg gagggttgt atcgattaga
 541    tgaaaaaaat caaccgcaac cagccattgc agctggtcaa ccaaaagtat cgaataatgg
 601    caaaacttat accattgtga ttagagatgg cgctaagtgg tctgatggta cacaaataac
 661    tgctagtgat tttgtggccg cgtggcaaag agttgtagat cctaaaacag tttctccaaa
 721    tgtggaactg ttttctgcta taaaaatgc caaagaaatt gcttcaggaa aacaagcaaa
 781    agatactta gcagtgaaaa gtattggtga gaaacatta gaaatcgaat tagttgaacc
 841    aacaccttat tttactgatc tgttatcctt aaccgcttac tatccagtac agcagaaagc
 901    aattaaagag tatgggaaag actatggggt ttctcaaaaa gcaattgtaa caaatggagc
 961    atttaactta acaaacttag agggagtagg aacttctgat aagtggacga tttctaaaaa
1021    taaagagtac tgggatcaaa aagatgtttc tatggataaa attaatttc aagtcgtcaa
1081    agaaattaat acaggaataa atttgtataa tgatgggcaa ttagatgagg cgcctttagc
1141    tggtgaatat gcaaaacaat acaagaaaga taaagaatat tcaacaacat taatggctaa
1201    tacaatgttt ttagaaatga accaaactgg ggaaataag cttttacaaa acaaaaatgt
1261    ccgaaaagcg attaactatg caattgatcg ggaaagtcta gttaaaaaat tactagataa
1321    tgggtccgtt gcttctgttg gcgtagtacc aaaagaaatg gcctttaatc cggtaaataa
1381    aaaagatttt gctaatgaaa aattagttga atttaacaaa aaacaagcag aagagtattg
1441    ggataaggct aaaaaagaaa ttgatttatc caaaaatact tctttagatt tacttgtaag
```

FIG. 6-2

```
1501 tgatggagag tttgaaaaaa aggcaggaga atttctgcaa ggacagttgc aagatagctt
1561 agaaggattg aaggttactg tgacgccaat tcctgcaaat gtctttatgg aacgcctaac
1621 aaaaaaggat tttactttga gcctaagtgg atggcaagct gattatgcag acccjattag
1681 cttttagca aactttgaaa caaatagtcc aatgaatcat ggtggatatt caaataaaaa
1741 ttatgatgaa ttgctaaagg attcttcttc taaacgttgg caagaattga aaaagctga
1801 aaaattgttg atcaatgata tggggtcgt tccaattttt caagttggaa cagcaaaatt
1861 agaaaaaagt aaaataaaaa atgttttaat gcattcaata ggagcaaaat atgactacaa
1921 aaaaatgaga atagagaagt aatggagggt atatggaatt agttcgtcgc gtttttataa
1981 ggtaccctgc ag
           PstI
```

FIG. 8-1

```
gggatccaaaaggaggagaaaactactatgaaaaaaagattatctcagctattttaatg
                         M  K  K  I  I  S  A  I  L  M
tctacagtgatactttctgctgcagccccgttgtcaggtgtttacgctaccactcatagt   ⎤
 S  T  V  I  L  S  A  A  A  P  L  S  G  V  Y  A  T  T  H  S    ⎪
ggaaaatattatggaaatggagtgtattgcactaaaaataaatgtacggtcgattgggcc   ⎬ entA
 G  K  Y  Y  G  N  G  V  Y  C  T  K  N  K  C  T  V  D  W  A    ⎪
aaggcaactacttgtattgcaggaatgtctataggtggttttttaggtggagcaattcca   ⎪
 K  A  T  T  C  I  A  G  M  S  I  G  G  F  L  G  G  A  I  P    ⎦
ggaagtgctaaaatgaaaaaaaatgctaagcaaattgttcatgaattatataatgatat   ⎤
 G  K  C  -  M  K  K  N  A  K  Q  I  V  H  E  L  Y  N  D  I    ⎪
atctataagtaaagatcctaaatattctgatattcttgaggttttacaaaaggtatattt   ⎪
 S  I  S  K  D  P  K  Y  S  D  I  L  E  V  L  Q  K  V  Y  L    ⎪
aaaattagaaaaacaaaaatatgaattagatcccggtcctttaataaatagattggtgaa   ⎬ entiA
 K  L  E  K  Q  K  Y  E  L  D  P  G  P  L  I  N  R  L  V  N    ⎪
ttatctatattttactgcttatactaataaaataagattcactgaatatcaagaggaatt   ⎪
 Y  L  Y  F  T  A  Y  T  N  K  I  R  F  T  E  Y  Q  E  E  L    ⎪
aataagaaatttgagtgaaattggaagaactgctggaataaatggtttatatcgagcaga   ⎦
 I  R  N  L  S  E  I  G  R  T  A  G  I  N  G  L  Y  R  A  D
ttatggagataaatctcaattttaataaggaggaataataatgaaaaagaaagtattaa   ⎤
 Y  G  D  K  S  Q  F  -              M  K  K  V  L            ⎪
aacattgtgttattctaggaatattaggaacttgtctagctggcatcggtacaggaataa   ⎪
 K  H  C  V  I  L  G  I  L  G  T  C  L  A  G  I  G  T  G  I    ⎬ hirJM79
aagttgatgcagctacttactatggaaatggtctttattgtaacaaagaaaaatgttggg   ⎪
 K  V  D  A  A  T  Y  Y  G  N  G  L  Y  C  N  K  E  K  C  W    ⎪
tagattggaatcaagctaaaggagaaattggaaaaattattgttaatggttgggttaatc   ⎦
 V  D  W  N  Q  A  K  G  E  I  G  K  I  I  V  N  G  W  V  N
atggtccatgggcacctagaaggtagtggtagggaggttattataatggattttactaaa   ⎤
 H  G  P  W  A  P  R  R  -                    M  D  F  T  K    ⎪
gaagaaaaacttttaaatgcaattagtaaagtatacaatgaagcaactatagatgactat   ⎪
 E  E  K  L  L  N  A  I  S  K  V  Y  N  E  A  T  I  D  D  Y    ⎪
cctgacttaaaagaaaagctctttctttattctaaagaaatcagtgagggaaaaagtgtt   ⎬ hirIJM79
 P  D  L  K  E  K  L  F  L  Y  S  K  E  I  S  E  G  K  S  V    ⎪
ggtgaagttagtatgaaattaagtagttttcttggaagatatattttaaaacataaattt   ⎪
 G  E  V  S  M  K  L  S  S  F  L  G  R  Y  I  L  K  H  K  F    ⎪
ggattacctaaatctttaatagaattacaagaaattgttagtaaggaatctcaagtatat   ⎦
 G  L  P  K  S  L  I  E  L  Q  E  I  V  S  K  E  S  Q  V  Y
agaggatgggcttctattggtatttggagttaaaaaggaggtattgatttatgagaaaaa   ⎤
 R  G  W  A  S  I  G  I  W  S  -                 M  R  K       ⎪
aattatttagtttagctcttattggaatatttggttagttgtgacaaattttggtacaa   ⎪
 K  L  F  S  L  A  L  I  G  I  F  G  L  V  V  T  N  F  G  T    ⎪
aagttgatgcagctacgcgttcatatggtaatggtgtttattgtaataatagtaaatgct   ⎬ entP
 K  V  D  A  A  T  R  S  Y  G  N  G  V  Y  C  N  N  S  K  C    ⎪
gggttaactggggagaagctaaagagaatattgcaggaatcgttattagtggctggctt   ⎪
 W  V  N  W  G  E  A  K  E  N  I  A  G  I  V  I  S  G  W  A    ⎦
ctggtttggcaggtatgggacattaatactatgaaaagtaataaatctttcaacaaagtt   ⎤
 S  G  L  A  G  M  G  H  -           M  K  S  N  K  S  F  N  K  V ⎬ entiP
                                                                 ⎦
```

Fig. 8-2

```
ctagaattaactgaaacagcattagccaccccagaaattaaaaaagataaaaatctatgt
 L  E  L  T  E  T  A  L  A  T  P  E  I  K  K  D  K  N  L  C
gaaattttagaaaaagtaaaagctagtgctgctaaaggtgaattttattatgattacaag
 E  I  L  E  K  V  K  A  S  A  A  K  G  E  F  Y  Y  D  Y  K
aaagaatttcaacctgcaattagtggattcactattagaaacggcttttccacaccgaag
 K  E  F  Q  P  A  I  S  G  F  T  I  R  N  G  F  S  T  P  K
gttttattggagttgcttgctgaagtaaaaactcccaaagcatggtcgggactttgataa
 V  L  L  E  L  L  A  E  V  K  T  P  K  A  W  S  G  L  -
gaattc
```
Lys170\*

```
gggatccaaaaggaggagaaaactactatgaaaaaaagattatctcagctattttaatg
                             M  K  K  I  I  S  A  I  L  M
tctacagtgatactttctgctgcagccccgttgtcaggtgtttacgctaagacgtctgca
 S  T  V  I  L  S  A  A  A  P  L  S  G  V  Y  A  K  T  S  A
ggagaagtatttagtagcttgattacaagtgtaaatcctaacccaatgaacgcaggtagt
 G  E  V  F  S  S  L  I  T  S  V  N  P  N  P  M  N  A  G  S
cgtaatggtatccctatcgacaccattatcctacatcacaatgcaacaacaaataaagat
 R  N  G  I  P  I  D  T  I  I  L  H  H  N  A  T  T  N  K  D
gttgctatgaacacatggctattaggtggtggcgcaggtacatctgctcattatgaatgt
 V  A  M  N  T  W  L  L  G  G  A  G  T  S  A  H  Y  E  C
acaccaacagaaattattggatgtgtcggtgagcagtattcagcattccatgccggaggt
 T  P  T  E  I  I  G  C  V  G  E  Q  Y  S  A  F  H  A  G  G
acaggtggtatagatgttcctaagattgctaaccctaaccaacgttcaataggtattgaa
 T  G  G  I  D  V  P  K  I  A  N  P  N  Q  R  S  I  G  I  E
aatgtaaactcgtcaggagcacctaattggtctgtagaccctagaacaattacaaattgt
 N  V  N  S  S  G  A  P  N  W  S  V  D  P  R  T  I  T  N  C
gctcgtttagtggcagatatttgtacacgttatggtattccatgtgaccgacaacacgtg
 A  R  L  V  A  D  I  C  T  R  Y  G  I  P  C  D  R  Q  H  V
ttaggacataacgaagtaactgcaacagcgtgccccggaggtatggacgtagacgaagtt
 L  G  H  N  E  V  T  A  T  A  C  P  G  G  M  D  V  D  E  V
gtacgtcaagctcaacagttcatggcaggaggctctaacaatgcagttaagccggagcca
 V  R  Q  A  Q  Q  F  M  A  G  G  S  N  N  A  V  K  P  E  P
agtaagcctacaccaagcaaaccaagtaataataaaaataaagaaggagtggcaactatg
 S  K  P  T  P  S  K  P  S  N  N  K  N  K  E  G  V  A  T  M
tattgtttatacgaaagacctattaactcaaaaacaggagtactagagtggaatggtgat
 Y  C  L  Y  E  R  P  I  N  S  K  T  G  V  L  E  W  N  G  D
gcatggacagttatgttctgtaatggggtaaactgtcgcagagtatctcatccagatgaa
 A  W  T  V  M  F  C  N  G  V  N  C  R  R  V  S  H  P  D  E
atgaaagtaattgaggatatttacagaaaaaataacggaaaagacattccatttttacagt
 M  K  V  I  E  D  I  Y  R  K  N  N  G  K  D  I  P  F  Y  S
caaaaagaatggaataaaaatgcaccatggtataacagattagagacagtatgtccagta
 Q  K  E  W  N  K  N  A  P  W  Y  N  R  L  E  T  V  C  P  V
gtaggtattactaaaaaatcttaataagaattc
 V  G  I  T  K  K  S  -
```

Fig. 9-1

TET-PC64-GFP (SEQ ID NO:8)

```
   1 AGATCTCAAA TAAAAAGAGT TGGTTGAGAT TTCAACTAGC TCTTTTTATT TTAAATTGGT
     NcoI  <-----------------Terminator---------------------------->
  61 ACCCTCGAGT TCATGAAAAA CTAAAAAAAA TATTGACACT CTATCATTGA TAGAGTATAA
     KpnI  -----------------------------Ptet---------------------------
 121 TTAAAATAAG CTCTCTATCA TTGATAGAGT ATGATGGAAC CGGGAAAAGG TGGTGAACTA
     ---------------------------------Ptet---------------------------
 181 CTCCATGGTA TAATGAAAAA AAGATTATC  TCAGCTATTT TAATGTCTAC AGTGATACTT
      -> NcoI  -------------------PC64a---------------------------
 241 TCTGCTGCAG CCCCGTTGTC AGGTGTTTAC GCTTAACAT ATTGTCGTCG TCGTTTTTGT
     -------------------------------PC64a-------------------------
 301 GTTACAGTTT AAACGTATCT AGAAGAATTC CCCGGCTTTA GGTATAGTGT GTATCTCAAT
     ---------->         XbaI  ---------------PnisR------------------
 361 CCTTGGTATA TTGAAAAGAA AGACTAAAAA TTGATAGATT ATATTTCTTC AGAATGAATG
     -------------------------------PnisR-----------------------------
 421 GTATAATGAA GTAATGAGTA CTAAACAATC GGAGGTAAAA TGATGTCACG TTTAGATAAA
     ------------------------------------------> --------tetR---------
 481 TCAAAAGTTA TTAATTCAGC TTTAGAATTA TTAAATGAAG TTGGTATTGA AGGTTTAACA
     --------------------------------tetR-----------------------------
 541 ACACGTAAAT TAGCTCAAAA ATTAGGTGTT GAACAACCAA CATTATATTG GCATGTTAAA
     ---------------------------tetR----------------------------------
 601 AATAAACGTG CTTTATTAGA TGCTTTAGCT ATTGAAATGT TAGATCGTCA TCATACACAT
     ---------------------------tetR----------------------------------
 661 TTTTGTCCAT TAGAAGGTGA ATCATGGCAA GATTTTTTAC GTAATAATGC TAAATCATTT
     ---------------------------tetR----------------------------------
 721 CGTTGTGCTT TATTATCACA TCGTGATGGT GCTAAAGTTC ATTTAGGTAC ACGTCCAACA
     ---------------------------tetR----------------------------------
 781 GAAAAACAAT ATGAAACATT AGAAAATCAA TTAGCTTTTT TATGTCAACA AGGTTTTTCA
     ---------------------------tetR----------------------------------
 841 TTAGAAAATG CTTTATATGC TTTATCAGCT GTTGGTCATT TTACATTAGG TTGTGTTTTA
     ---------------------------tetR----------------------------------
 901 GAAGATCAAG AACATCAAGT TGCTAAAGAA GAACGTGAAA CACCAACAAC AGATTCAATG
     ---------------------------tetR----------------------------------
 961 CCACCATTAT TACGTCAAGC TATTGAATTA TTTGATCATC AAGGTGCTGA ACCAGCTTTT
     ---------------------------tetR----------------------------------
1021 TTATTTGGTT TAGAATTAAT TATTTGTGGT TTAGAAAAAC AATTAAAATG TGAATCAGGT
     ---------------------------tetR----------------------------------
1081 TCATAAGAGC TCTAATAGCC ATGGTATAAT GCGTAAAGGA GAAGAACTTT TCACTGGAGT
     ------> SacI          NcoI        --------------gfp--------------
```

Fig. 9-2

```
1141  TGTCCCAATT CTTGTTGAAT TAGATGGTGA TGTTAATGGG CACAAATTTT CTGTCAGTGG
      --------------------------------gfp-------------------------------
1201  AGAGGGTGAA GGTGATGCAA CATACGGAAA ACTTACCCTT AAATTTATTT GCACTACTGG
      --------------------------------gfp-------------------------------
1261  AAAACTACCT GTTCCATGGC CAACACTTGT CACTACTTTG ACTTATGGTG TTCAATGCTT
      --------------------------------gfp-------------------------------
1321  TTCAAGATAC CCAGATCATA TGAAACGGCA TGACTTTTTC AAGAGTGCCA TGCCCGAAGG
      --------------------------------gfp-------------------------------
1381  TTATGTACAG GAAAGAACTA TATTTTTCAA AGATGACGGG AACTACAAGA CACGTGCTGA
      --------------------------------gfp-------------------------------
1441  AGTCAAGTTT GAAGGTGATA CCCTTGTTAA TAGAATCGAG TTAAAAGGTA TTGATTTTAA
      --------------------------------gfp-------------------------------
1501  AGAAGATGGA ACATTCTTG GACACAAATT GGAATACAAC TATAACTCAC ACAATGTATA
      --------------------------------gfp-------------------------------
1561  CATCATGGCA GACAAACAAA AGAATGGAAT CAAAGTTAAC TTCAAAATTA GACACAACAT
      --------------------------------gfp-------------------------------
1621  TGAAGATGGA AGCGTTCAAC TAGCAGACCA TTATCAACAA ATACTCCAA TTGGCGATGG
      --------------------------------gfp-------------------------------
1681  CCCTGTCCTT TTACCAGACA ACCATTACCT GTCCACACAA TCTGCCCTTT CGAAAGATCC
      --------------------------------gfp-------------------------------
1741  CAACGAAAAG AGAGACCACA TGGTCCTTCT TGAGTTTGTA ACAGCTGCTG GGATTACACA
      --------------------------------gfp-------------------------------
1801  TGGCATGGAT GAACTATACA AATAAACGTA TCTAGATAAT GAAGCTT
      -----------gfp----------------->  XbaI       HindIII
```

LAC-ALYS (SEQ ID NO:9)

```
  1  AGATCTCAAA TAAAAGAGT TGGTTGAGAT TTCAACTAGC TCTTTTTATT TTAAATTGGT
     NcoI   <---------------------Terminator--------------------------->
 61  ACCGAATTCG GTGGAAACGA GGTCATCATT TCCTTCGAA AAAACGGTTG CATTTAAATC
     KpnI  -----------------------------Plac--------------------------
121  TTACATATGT AATACTTTCA ATTGTGAGCG GATAACAATT CCGGATCAAT CAAATATTCA
     ----------------------------------Plac--------------------------
181  AACGGAGGGA GACGATTTTG CCATGGTATA ATGAAAAAAA AGATTATCTC AGCTATTTA
     -----------------------> NcoI             -----------Alysteserin--------
241  ATGTCTACAG TGATACTTTC TGCTGCAGCC CCGTTGTCAG GTGTTTACGC TGGTTTAAAA
     --------------------------------Alysteserin------------------------
301  GATATTTTTA AAGCTGGTTT AGGTTCATTA GTTAAAGGTA TTGCTGCTCA TGTTGCTAAT
     --------------------------------Alysteserin------------------------
```

Fig. 9-3

```
 361 TAAACGTATC TAGAAGAATT CCCCGGCTTT AGGTATAGTG TGTATCTCAA TCCTTGGTAT
     ->        XbaI      ------------------PnisR----------------------
 421 ATTGAAAAGA AAGACTAAAA ATTGATAGAT TATATTTCTT CAGAATGAAT GGTATAATGA
     -------------------------PnisR---------------------------> ---
 481 AGTAATGAGT ACTAAACAAT CGGAGGTAAA ATGAAACCAG TTACATTATA TGATGTTGCT
     ----------------------------lacI---------------------------------
 541 GAATATGCTG GTGTTTCATA TCAAACAGTT TCTCGTGTTG TTAATCAAGC ATCACATGTT
     ----------------------------lacI---------------------------------
 601 TCAGCTAAAA CACGTGAAAA AGTTGAAGCT GCTATGGCTG AATTAAATTA TATTCCAAAT
     ----------------------------lacI---------------------------------
 661 CGTGTTGCTC AACAATTAGC TGGTAAACAA TCATTATTAA TTGGTGTTGC TACATCATCA
     ----------------------------lacI---------------------------------
 721 TTAGCTTTAC ATGCTCCATC ACAAATTGTT GCTGCTATTA ATCACGTGC TGATCAATTA
     ----------------------------lacI---------------------------------
 781 GGTGCTTCAG TTGTTGTTTC AATGGTTGAA CGTTCAGGTG TTGAAGCATG TAAAGCTGCT
     ----------------------------lacI---------------------------------
 841 GTTCATAATT TATTAGCTCA ACGTGTTTCA GGTTTAATTA TTAATTATCC ATTAGATGAT
     ----------------------------lacI---------------------------------
 901 CAAGATGCTA TTGCTGTTGA AGCTGCTTGT ACAAATGTTC CAGCTTTATT TTTAGATGTT
     ----------------------------lacI---------------------------------
 961 TCAGATCAAA CACCAATTAA TTCAATTATT TTTTCACATG AAGATGGTAC ACGTTTAGGT
     ----------------------------lacI---------------------------------
1021 GTTGAACATT TAGTTGCTTT AGGTCATCAA CAAATTGCTT TATTAGCTGG TCCATTATCA
     ----------------------------lacI---------------------------------
1081 TCAGTTTCAG CTCGTTTACG TTTAGCTGGT TGGCATAAAT ATTTAACACG TAATCAAATT
     ----------------------------lacI---------------------------------
1141 CAACCTATTG CTGAACGTGA AGGTGATTGG TCAGCTATGT CAGGTTTTCA ACAAACAATG
     ----------------------------lacI---------------------------------
1201 CAAATGTTAA ATGAAGGTAT TGTTCCAACA GCTATGTTAG TTGCTAATGA TCAAATGGCT
     ----------------------------lacI---------------------------------
1261 TTAGGTGCTA TGCGTGCTAT TACAGAATCA GGTTTACGTG TTGGTGCTGA TATTTCAGTT
     ----------------------------lacI---------------------------------
1321 GTTGGTTATG ATGATACAGA AGATTCATCA TGTTATATTC CACCATTAAC AACAATTAAA
     ----------------------------lacI---------------------------------
1381 CAAGATTTTC GTTTATTAGG TCAAACATCA GTTGATCGTT TATTACAATT ATCACAAGGT
     ----------------------------lacI---------------------------------
1441 CAAGCTGTTA AAGGTAATCA ATTATTACCA GTTTCATTAG TTAAACGTAA AACAACATTA
     ----------------------------lacI---------------------------------
```

Fig. 9-4

```
1501 GCTCCAAATA CACAAACAGC TTCACCACGT GCTTTAGCTG ATTCATTAAT GCAATTAGCT
     -------------------------------------lacI-------------------------------------
1561 CGTCAAGTTT CACGTTTAGA ATCAGGTCAA TAAGAGCTC
     ------------------------------------> SacI
```

XYL – A3APO (SEQ ID NO:10)

```
  1 AGATCTCAAA TAAAAAGAGT TGGTTGAGAT TCAACTAGC TCTTTTTATT TTAAATTGGT
    NcoI <---------------Terminator-------------------------->
 61 ACCCGAATTC GGTGGAAACG AGGTCATCAT TTCCTTCCGA AAAAACGGAA CATTGAAATA
    KpnI                                                      -----Pxyl----
121 AACATTTATT TTGTATATGA TGAGATAAAG TTAGTTTATT GGATAAACAA ACTAACTCAA
    -----------------------------Pxyl----------------------------------
181 TTAAGATAGT TGATGGATAA ACTTGTTCAC TTAAATCAAA GGGGGAAATG ACAACCATGG
    ----------------------Pxyl---------------------------> NcoI
241 TATAATGAAA AAAAGATTA TCTCAGCTAT TTTAATGTCT ACAGTGATAC TTTCTGCTGC
    -----------------------------A3-APO---------------------------
301 AGCCCCGTTG TCAGGTGTTT ACGCTCGTCC AGATAAACCA CGTCCATATT TACCACGTCC
    -----------------------------A3-APO---------------------------
361 ACGTCCACCA CGTCCAGTTC GTTAAACGTA TCTAGAAGAA TTCCCCGGCT TAGGTATAG
    -----------A3-APO---------> XbaI   -----------PnisR----------
421 TGTGTATCTC AATCCTTGGT ATATTGAAAA GAAAGACTAA AAATTGATAG ATTATATTTC
    ------------------------------PnisR---------------------------
481 TTCAGAATGA ATGGTATAAT GAAGTAATGA GTACTAAACA ATCGGAGGTA AAATGTTTAC
    ------------------------------PnisR--------------------> -------
541 AAAACGTCAT CGTATTACAT TATTATTTAA TGCTAATAAA GCCTATGATC GTCAAGTTGT
    -----------------------------xylR------------------------------
601 TGAAGGTGTT GGTGAATATT TACAAGCCTC ACAATCAGAA TGGGATATTT TTATTGAAGA
    -----------------------------xylR------------------------------
661 AGATTTTCGT GCTCGTATTG ATAAAATTAA AGATTGGTTA GGTGATGGTG TTATTGCTGA
    -----------------------------xylR------------------------------
721 TTTTGATGAT AAACAAATTG AACAAGCCTT AGCTGATGTT GATGTTCCAA TTGTTGGTGT
    -----------------------------xylR------------------------------
781 TGGTGGTTCA TATCATTTAG CTGAATCATA TCCACCAGTT CATTATATTG CTACAGATAA
    -----------------------------xylR------------------------------
841 TTATGCTTTA GTTGAATCAG CTTTTTTACA TTTAAAAGAA AAGGTGTTA ATCGTTTTGC
    -----------------------------xylR------------------------------
901 TTTTTATGGT TTACCAGAAT CATCAGGTAA ACGTTGGGCT ACAGAACGTG AATATGCTTT
    -----------------------------xylR------------------------------
```

Fig. 9-5

```
 961 TCGTCAATTA GTTGCTGAAG AAAAATATCG TGGTGTTGTT TATCAAGGTT TAGAAACAGC
     ---------------------------xylR----------------------------------
1021 TCCAGAAAAT TGGCAACATG CTCAAAATCG TTTAGCTGAT TGGTTACAAA CATTACCACC
     ---------------------------xylR----------------------------------
1081 ACAAACAGGT ATTATTGCTG TTACAGATGC TCGTGCTCGT CATATTTTAC AAGTTTGTGA
     ---------------------------xylR----------------------------------
1141 ACATTTACAT ATTCCAGTTC CAGAAAAATT ATGTGTTATT GGTATTGATA ATGAAGAATT
     ---------------------------xylR----------------------------------
1201 AACTCGTTAT TTATCACGTG TTGCTTTATC ATCAGTTGCT CAAGGTGCTC GTCAAATGGG
     ---------------------------xylR----------------------------------
1261 TTATCAAGCT GCTAAATTAT TACATCGTTT ATTAGATAAA GAAGAAATGC CATTACAACG
     ---------------------------xylR----------------------------------
1321 TATTTTAGTT CCACCAGTTC GTGTTATTGA ACGTCGTTCA ACAGATTATC GTTCATTAAC
     ---------------------------xylR----------------------------------

1381 AGATCCAGCT GTTATTCAAG CTATGCATTA TATTCGTAAT CATGCTTGTA AAGGTATTAA
     ---------------------------xylR----------------------------------
1441 AGTTGATCAA GTTTAGATG CTGTTGGTAT TTCACGTTCA AATTTAGAAA AACGTTTTAA
     ---------------------------xylR----------------------------------
1501 AGAAGAAGTT GGTGAAACAA TTCATGCTAT GATTCATGCT GAAAAATTAG AAAAAGCTCG
     ---------------------------xylR----------------------------------
1561 TTCATTATTA ATTTCAACAA CATTATCAAT TAATGAAATT TCACAAATGT GTGGTTATCC
     ---------------------------xylR----------------------------------
1621 ATCATTACAA TATTTTTATT CAGTTTTTAA AAAAGCCTAT GATACAACAC CAAAAGAATA
     ---------------------------xylR----------------------------------
1681 TCGTGATGTT AATTCAGAAG TTATGTTATA AGAGCTC
     -----------xylR----------------> SacI
```

FIG. 10

SEQ ID NO:3

MFKIGSVLKQIRQELNYHQIDLYSGIMSKSVYIKVEADSRPISVEELSKFSERLGVNFFE
ILNRAGMNTKSVNETGKEKLLISKIFTNPDLFDKNFQRIEPKRLTSLQYFSIYLGYISIA
HHYNIEVPTFNKTITSDLKHLYDKRTTFFGIDYEIVSNLLNVLPYEEVSSIIKPMYPIVD
SFGKDYDLTIQTVLKNALTISIMNRNLKEAQYYINQFEHLKTIKNISINGYYDLEINYLK
QIYQFLTDKNIDSYLNAVNIINIFKIIGKEDIHRSLVEELTKISAKEKFTPPKEVTMYYE
NYVAIENNPIPEIKEQS

SEQ ID NO:4

MKKYKKFCFLGIGLLPLVLASCGTNTATKDSQDATEKKVEQVATLTAGTPVQSLDPATAV
DQTSITLLANVMEGLYRLDEKNQPQPAIAAGQPKVSNNGKTYTIVIRDGAKWSDGTQITA
SDFVAAWQRVVDPKTVSPNVELFSAIKNAKEIASGKQAKDTLAVKSIGEKTLEIELVEPT
PYFTDLLSLTAYYPVQQKAIKEYGKDYGVSQKAIVTNGAFNLTNLEGVGTSDKWTISKNK
EYWDQKDVSMDKINFQVVKEINTGINLYNDGQLDEAPLAGEYAKQYKKDKEYSTTLMANT
MFLEMNQTGENKLLQNKNVRKAINYAIDRESLVKKLLDNGSVASVGVVPKEMAFNPVNKK
DFANEKLVEFNKKQAEEYWDKAKKEIDLSKNTSLDLLVSDGEFEKKAGEFLQGQLQDSLE
GLKVTVTPIPANVFMERLTKKDFTLSLSGWQADYADPISFLANFETNSPMNHGGYSNKNY
DELLKDSSSKRWQELKKAEKLLINDMGVVPIFQVGTAKLEKSKIKNVLMHSIGAKYDYKK
MRIEK

Fig. 11-1 pPD1

SEQ ID NO:5

```
agttaatcta ttttttgtg gtcaaaattt ttggggtcta atacttgtcc atcatcgtca agaacaccaa
atatttgttt tgcttttca tcatcacttt tagaaatgat tgtttgtaag ttttatgga attgctcaac
atattcaggg ctttccactt gtttcaatat ttcaacatac gagaatactt tcataatatg ctctatatct
ccagaagtaa agtatagaag catatttctt gaagctatga aacttaattt atatttataa ctagtgtaat
ttgataacaa agtttcaaag tgatttagaa gtataaagca agaactgtaa tcctttgtaa atatacttag
agcaattgca ttagacaagg ataaacaagc tgtatcttta atctgctcgt cactatcttc acgtaaagga
aatagttgct ctatcaatgt ctgaagatca gagtaaggga atatagtgca tagattagaa agaattttat
agtgatacaa tacaaatctt ttgcttgatg aaaacatctt ttttatatca gctaaatctt gtttatccac
aggaataatt tctgaaatca aactagaggt ttgcaatttt ataagtaaat ataaattcat gtattttaac
gaagtaaatt tttcatgtat agattttga taaagagagt agagttcttg attgtattct gaatcaggat
tttgttgaat ttttgaaaga acaaaataat atgtttctaa atctttatca aaaacacttt taaaatcttc
attacaagtt ctaattattt caggtattgt taaattactt ctatctgcaa gaattggcaa atcagcaatt
tttaaaaaat gttcattatg gttttcaaaa aggcttgctg aattacgctg aaaaatacct tcataaaact
tagcttgaga taatttctcg ctttttcttt gtatttcat taattcattt aaatgcatat attcaactcc
tataaatgta ttctgaatat gacgaaaatc ggcaaaaaaa agaaaataaa taaaaatga attattttc
ccggaaacgt cttttttaaa atacatatac ttgtaatgag taaactttaa tgctatagta gtaactgtaa
tgaatagtta ctaagtgagg taaatttaat gaaacaacaa aaaaaacata tagctgcatt attgtttgca
ctaatattaa ctcttgtttc ttaaaaaaaa
```

TraA (SEQ ID NO:53)

MHLNELMKIQRKSEKLSQAKFYEGIFQRNSASLFENHNEHFLKIADLPILADRSNLTIPEIIRTCNEDFKSVFDKDLETYYFV
LSKIQQNPDSEYNQELYSLYQKSIHEKFTSLKYMNLYLLIKLQTSSLISEIIPVDKQDLADIKKMFSSSKRFVLYHYKILSNLCTI
FPYSDLQTLIEQLFPLREDSDEQIKDTACLSLSNAIALSIFTKDYSSCFILLNHFETLLSNYTSYKYKLSFIASRNMLLYFTSGDI
EHIMKVFSYVEILKQVESPEYVEQFHKNLQTIISKSDDEKAKQIFGVLDDDGQVLDPKNFDHKKID lpd (SEQ ID NO:56)

MKQQKKHIAALLFALILTLVS

Fig. 11-2 pAD1

SEQ ID NO:6

```
ctagagtagt tactctagtc ttttggttat tttcttttcg tttagtttta tatgattatt ttctttagta
agtaaagtat ctggtttact catagaacca ttatttttt ttgagatcat tagataaatg ttatctttca
ttaattttgc tagctcgaca ttttctaagt ctcctaatag atcgacatat ttaattgagt tatttaaaga
atccatgttg tttgttaaaa agtaaccaac taaattataa gttattaaat aatttagttt atacttatat
gacgggaatt tttgcaataa atcattgtag atattcagaa cttctgtaca actttcaaaa tctcggtttt
gaacgagttt agtagtaatg ttttcaagta aatagtatgc tgcttcacta gtaactgttg gagcgtttga
atctaatgga aatagactag atagaaacgg ttgcaattct ttgtaagaaa atacaagaga tagattagta
acaattttat agtcgtaaag agtaaacttt tgttttgata aaatcatttt ttttaactca gataaatctt
gtgagtctgt agggacaatt cttgaatcgt attcagaaca ttggattttt attattaagt aaagattcca
atatattata gaatgttctt ttagctctat agactttttg tataatttgt aaatgtagtc tttatttct
ttttcggtat tattctggaa tatatcaaac aatgaattta agtcttcgtc gtaaggagaa ataaattctt
ctttagcata atgaattatt tctaagatac tcatcatgct tctatctgat aaaacaggta aatctttaac
tttgagatca tgcgtgttgt gtacctcaaa agaagaggca gctctttttt tgaatattcc ttcataaaat
tcttcttgag taaaattata gagttttcgc tgttctttga atagttcgta aagaaacatt ttgaaatact
ccttccgagg cgcaaaaaag tgcattcgtg aatgattttt ttggtttttt tattatgtaa taaatttttt
tgatgaaaaa gcgcaaattt ttgcattttt gtttattttt attttaatct atgctattat taatttgtaa
gttaagttta aataagagga gagctattag aatgagcaaa cgagctatga aaaaattat tccattgata
actttatttg ttgtcacact tgtaggataa
```

TraA (SEQ ID NO:54)

MFLYELFKEQRKLYNFTQEEFYEGIFKKRAASSFEVHNTHDLKVKDLPVLSDRSMMSILEIIHYAKEEFISPYDEDLNSLFDI
FQNNTEKENKDYIYKLYKKSIELKEHSIIYWNLYLIIKIQCSEYDSRIVPTDSQDLSELKKMILSKQKFTLYDYKIVTNLSLVFSY
KELQPFLSSLFPLDSNAPTVTSEAAYYLLENITTKLVQNRDFESCTEVLNIYNDLLQKFPSYKYKLNYLITYNLVGYFLTNNM
DSLNNSIKYVDLLGDLENVELAKLMKDNIYLMISKKNNGSMSKPDTLLTKENNHIKLNEKKITKRLE

Iad (SEQ ID NO:57)

MSKRAMKKIIPLITLFVVTLVG

Fig. 11-3

PAM373

SEQ ID NO:7

```
ctaagtttta actatatttg gaggaattgt ttgcatataa tcaatactgc ttttcgtatt agcaattgca
gctataatat ctttagtgtt atcttctttt tcgattatag aaacagtagc ttctttcatt ctatcagcta
gagaggaaga aggcggttca cagctatcaa taatattaat tatttgtaaa gcttcagtta atttactaga
attattgatc ttatctgtaa gaaaatcaag caatgctcta tcgtgtaaac aaatgagttt aaatttgtat
gatggattaa cttttaattg ttcttcaaaa ttattaatag ctaatttagc tttattgtag tctttatttt
ttatgtgctt agttgttaag tttgttaaag caaggtaagc aggatatagt atctcttcgg gaacattatt
tgctaaaggg tatagtacat caaacataaa gtttaaatca ttgacagtaa ataaaggtag cgttataaga
ttagctaata ctttataatc ggaagaagta taaagcttgc gtgttctata tatttttttt aggtccatga
gatctgcttt gtctacttct aaaatttat ctgtaaattc tgaacaagaa atttttataa gcaaatacaa
attaaaatat tttaaagagt agtatttagg ttcaatacac tgcatatata tggcagtaat atcttttgtg
acttcattta tttcagattt ttcttctaac gattgaaggc tggcatattt atttagaaag gagtctctta
gtttatcaaa atcagtgtgt aatgtatcag aggaatagaa taaaatctcc tcgcaagtta agtctaaacg
atcagctaga atgggaatgc aagatagttt gattgaagtt ttattctttt caaatttatc tgcagtactt
cttgataaaa catctttgta aaaagttgtt tgagataaat ttagattatt acgtgtatgc tttaaaaaat
cgtttataaa cataaaaaaa cctccaatat tcatatgtgt aaaaaaaacg cattttttgtt acttttttga
tgattttcta tgtaatttca gattttttt caaaatgatg tatgtttttt atacattgta ttttactgaa
taaaatcttg tggtatactt attttgtaag aattattgag aggggaaat ccacttgaaa aaagagttaa
ttttaatttt aaagtggttg acaccaatag gtttaagtat ttttacttta gtagcataac attttttgtaa
atggctctgt aatttttta tg
```

TraA (SEQ ID NO:55)

MNIGGFFMFINDFLKHTRNNLNLSQTTFYKDVLSRSTADKFEKNKTSIKLSCIPILADRLDLTCEEILFYSSDTLHTDFDKLR
DSFLNKYASLQSLEEKSEINEVTKDITAIYMQCIEPKYYSLKYFNLYLLIKISCSEFTDKILEVDKADLMDLKKIYRTRKLYTSSD
YKVLANLITLPLFTVNDLNFMFDVLYPLANNVPEEILYPAYLALTNLTTKHIKNKDYNKAKLAINNFEEQLKVNPSYKFKLIC
LHDRALLDFLTDKINNSSKLTEALQIINIIDSCEPPSSSLADRMKEATVSIIEKEDNTKDIIAAIANTKSSIDYMQTIPPNIVKT i373 (SEQ ID NO:58)

MKKELILILKWLTPIGLSIFTLVA

SEQUENCE LISTING

```
<160> NUMBER OF SEQ ID NOS: 66

<210> SEQ ID NO 1
<211> LENGTH: 10462
<212> TYPE: DNA
<213> ORGANISM: artificial
<220> FEATURE:
<223> OTHER INFORMATION: nucelotide sequence of the pBK2 plasmid

<400> SEQUENCE: 1
attttgttgg tggcttggaa atgtttaggc accttatata ataaaaaata aaagagcagt        60
catgaaaata ttttcatgac tgctctttta tttcaggaat aggattattt tctattgcaa       120
cgtaattttc ataatacatg gttacttctt taggggggcgt aaattttttct tttgcagata      180 tttttgtaag ttcctcaact aaagatctgt gaatatcttc ttttccaatg attttaaaga       240
tgttgataat atttaccgca tttaaataag aatcaatatt tttgtcagtt aaaaattgat       300
atatttgttt taaatagttt atttctaagt cgtaatatcc atttatgcta atattttaa        360 ttgttttttaa gtgttcaaat tgattaatat aatactgcgc ttcttttaga tttctattca     420
taattgatat tgttaaagca tttttagaa cagtctgaat agttaaatcg taatctttac        480
caaaggaatc cacgattgga tacataggct taatgatact tgaaacttct tcatacggta      540
agacatttaa aagatttgaa acaatttcat aatcaattcc aaaaaatgtt gttcttttat      600
catataaatg ttttaaatct gaagtaattg ttttattaaa agtaggaact tcaatgttat      660
aatgatgtgc aatagaaata tatccaagat aaatactaaa gtactgaaga ctagttaagc      720
gctttggctc aatcctttga aaatttttgt caaataagtc agggtttgta aatatttttg      780
aaataagaag ttttttcttt cctgtttcat ttacgctttt tgtattcatg ccagctctat      840
ttaaaatttc aaaaaatttt acacctaaac gttctgagaa cttgcttaac tcttctacag      900
aaatcggtcg agagtcagct tcaacttttta tgtaaacaga tttggacatt attccagaat     960
ataaatcaat ctgatggtaa tttaactctt gccttatttg tttcaggaca gaacctatct    1020
taaacatttt cttcctccta atatctcgag tatcaaaaag tagacctaaa attcgataaa    1080
ctacaaaaat ttgttaatat tttaatttta ggtattgaat acgacactcg aagatgtgtt    1140
tattaagcta tatccctttt tttttaaaaaa aaatacatat tttagttgaa aatataatac    1200
ttagatgtta agatgttttt ataggagggg tgtaaatgaa aaccactcta aaaaaactat    1260
caagatatat agctgttgta attgcaataa ccttaatatt tatctgatag aaaaaatcat    1320
agtaacaatt aaacaaatta agaaccgact gccataggac ggcaatccta gggggcagtt    1380
```

-continued

```
aaacaattca tggtatgaca tgaactctac tcggttctcg tttgttgcaa cattagttac   1440
aacgtatagt ataacaattt tttatgtaaa attctagact ttttaaaact cctttatttg   1500
tctaggaaaa gttttacag tgaattgttt ttattagttg tataaatgtt ggagcagcgg    1560
ggaatgtata cagttcatgt atatgttccc cgctttttt gttgtctgtt gggggatcca    1620
aaaggaggag aaaactacta tggaagttac tgacgtaaga ttacgggtcg accgggaaaa   1680
ccctggcgtt acccaactta atcgccttgc agcacatccc cctttcgcca gctggcgtaa   1740
tagcgaagag gcccgcaccg atcgcccttc ccaacagttg cgcagcctga atggcgaatg   1800
gcgctttgcc tggtttccgg caccagaagc ggtgccggaa agctggctgg agtgcgatct   1860
tcctgaggcc gatactgtcg tcgtcccctc aaactggcag atgcacggtt acgatgcgcc   1920 catctcacc aacgtaacct atcccattac ggtcaatccg ccgtttgttc ccacggagaa    1980
tccgacgggt tgttactcgc tcacatttaa tgttgatgaa agctggctac aggaaggcca   2040
gacgcgaatt atttttgatg gcgttaactc ggcgtttcat ctgtggtgca acgggcgctg   2100
ggtcggttac ggccaggaca gtcgtttgcc gtctgaattt gacctgagcg catttttacg   2160
cgccggagaa aaccgcctcg cggtgatggt gctgcgttgg agtgacggca gttatctgga   2220
agatcaggat atgtggcgga tgagcggcat tttccgtgac gtctcgttgc tgcataaacc   2280
gactacacaa atcagcgatt tccatgttgc cactcgcttt aatgatgatt tcagccgcgc   2340
tgtactggag gctgaagttc agatgtgcgg cgagttgcgt gactacctac gggtaacagt   2400
ttctttatgg cagggtgaaa cgcaggtcgc cagcggcacc gcgcctttcg gcggtgaaat   2460
tatcgatgag cgtggtggtt atgccgatcg cgtcacacta cgtctgaacg tcgaaaaccc   2520
gaaactgtgg agcgccgaaa tcccgaatct ctatcgtgcg gtggttgaac tgcacaccgc   2580
cgacggcacg ctgattgaag cagaagcctg cgatgtcggt ttccgcgagg tgcggattga   2640
aaatggtctg ctgctgctga acggcaagcc gttgctgatt cgaggcgtta accgtcacga   2700
gcatcatcct ctgcatggtc aggtcatgga tgagcagacg atggtgcagg atatcctgct   2760
gatgaagcag aacaacttta cgccgtgcg ctgttcgcat tatccgaacc atccgctgtg    2820
gtacacgctg tgcgaccgct acggcctgta tgtggtggat gaagccaata ttgaaaccca   2880
cggcatggtg ccaatgaatc gtctgaccga tgatccgcgc tggctaccgg cgatgagcga   2940
acgcgtaacg cgaatggtgc agcgcgatcg taatcacccg agtgtgatca tctggtcgct   3000
ggggaatgaa tcaggccacg gcgctaatca cgacgcgctg tatcgctgga tcaaatctgt   3060
cgatccttcc cgcccggtgc agtatgaagg cggcggagcc gacaccacgg ccaccgatat   3120
tatttgcccg atgtacgcgc gcgtggatga agaccagccc ttcccggctg tgccgaaatg   3180
gtccatcaaa aaatggcttt cgctacctgg agagacgcgc ccgctgatcc tttgcgaata   3240
cgcccacgcg atgggtaaca gtcttggcgg tttcgctaaa tactggcagg cgtttcgtca   3300 gtatcccgt ttacagggcg gcttcgtctg ggactgggtg atcagtcgc tgattaaata     3360 tgatgaaaac ggcaacccgt ggtcggctta cggcggtgat tttggcgata cgccgaacga   3420
tcgccagttc tgtatgaacg gtctggtctt tgccgaccgc acgccgcatc cagcgctgac   3480
ggaagcaaaa caccagcagc agttttttcca gttccgttta tccgggcaaa ccatcgaagt   3540
gaccagcgaa tacctgttcc gtcatagcga taacgagctc ctgcactgga tggtggcgct   3600
ggatggtaag ccgctggcaa gcggtgaagt gcctctggat gtcgctccac aaggtaaaca   3660
gttgattgaa ctgcctgaac taccgcagcc ggagagcgcc gggcaactct ggctcacagt   3720
acgcgtagtg caaccgaacg cgaccgcatg gtcagaagcc gggcacatca gcgcctggca   3780
```

```
gcagtggcgt ctggcggaaa acctcagtgt gacgctcccc gccgcgtccc acgccatccc    3840
gcatctgacc accagcgaaa tggattttg catcgagctg ggtaataagc gttggcaatt     3900
taaccgccag tcaggctttc tttcacagat gtggattggc gataaaaaac aactgctgac    3960
gccgctcgcg gatcagttca cccgtgcacc gctggataac gacattggcg taagtgaagc    4020
gacccgcatt gaccctaacg cctgggtcga acgctggaag gcggcgggcc attaccaggc    4080
cgaagcagcg ttgttgcagt gcacggcaga tacacttgct gatgcggtgc tgattacgac    4140
cgctcacgcg tggcagcatc aggggaaaac cttatttatc agccggaaaa cctaccggat    4200
tgatggtagt ggtcaaatgg cgattaccgt tgatgttgaa gtggcgagcg ataccgca      4260 tccggcgcgg attggcctga actgccagct ggcgcaggta gcagagcggg taaactggct    4320
cggattaggg ccgcaagaaa actatcccga ccgccttact gccgctgtt ttgaccgctg     4380 ggatctgcca ttgtcagaca tgtataccc gtacgtcttc ccgagcgaaa acggtctgcg     4440
ctgcgggacg cgcgaattga attatggccc acaccagtgg cgcggcgact tccagttcaa    4500
catcagccgc tacagtcaac agcaactgat ggaaaccagc catcgccatc tgctgcacgc    4560
ggaagaaggc acatggctga atatcgacgg tttccatatg gggattggtg gcacgactc     4620 ctggagcccg tcagtatcgg cggaattaca gctgagcgcc ggtcgctacc attaccagtt    4680
ggtctggtgt caaaataat aataagaatt ccttaaggaa cgtacagacg gcttaaaagc     4740
cttaaaaaac gttttaagg ggtttgtaga caaggtaaag gataaaacag cacaattcca     4800
agaaaaacac gatttagaac ctaaaaagaa cgaatttgaa ctaactcata accgagaggt    4860 aaaaaagaa cgaagtcgat tttttattaa aacgtctcaa aatcgtttct gagacgtttt      4920 agcgttatt tcgtttagtt atcggcataa tcgttaaaac aggcgttatc gtagcgtaaa     4980
agcccttgag cgtagcgtgg ctttgcagcg aagatgttgt ctgttagatt atgaaagccg    5040
atgactgaat gaaataataa gcgcagcgtc cttctatttc ggttggagga ggctcaaggg    5100
agtttgaggg aatgaaattc cctcatgggt ttgattttaa aaattgcttg caattttgcc    5160
gagcggtagc gctggaaaat ttttgaaaaa aatttggaat ttggaaaaaa atgggggaa     5220 aggaagcgaa ttttgcttcc gtactacgac ccccattaa gtgccgagtg ccaattttttg    5280 tgccaaaaac gctctatccc aactggctca agggtttgag gggttttca atcgccaacg     5340 aatcgccaac gttttcgcca acgttttta taaatctata tttaagtagc tttattgttg     5400
ttttatgatt acaaagtgat acactaattt tataaatta tttgattgga gttttttaaa     5460
tggtgatttc agaatcgaaa aaaagagtta tgatttctct gacaaagag caagataaaa     5520 atttaggagg catatcaaat gaactttaat aaaattgatt tagacaattg gaagagaaaa    5580
gagatattta atcattattt gaaccaacaa acgacttta gtataaccac agaaaattgat    5640 attagtgttt tataccgaaa cataaaacaa gaaggatata aattttaccc tgcatttatt    5700
ttcttagtga caagggtgat aaaactcaat acagctttta gaactggtta caatagcgac    5760
ggagagttag gttattggga taagttagag ccactttata caattttga tggtgtatct     5820 aaaacattct ctggtatttg gactcctgta aagaatgact tcaaagagtt ttatgattta    5880
taccttcctg atgtagagaa atataatggt tcggggaaat tgtttcccaa acacctata     5940 cctgaaaatg cttttctct ttctattatt ccatggactt catttactgg gtttaactta     6000
aatatcaata ataatagtaa ttaccttcta cccattatta cagcaggaaa attcattaat    6060
aaaggtaatt caatatattt accgctatct ttacaggtac atcattctgt ttgtgatggt    6120
```

-continued

```
tatcatgcag gattgtttat gaactctatt caggaattgt cagataggcc taatgactgg      6180
cttttataat atgagataat gccgactgta cttttttacag tcggttttct aacgatacat     6240
taataggtac gaaaaagcaa ctttttttgc gcttaaaacc agtcatacca ataacttaag      6300
ggtaactagc ctcgccggaa agagcgaaaa tgcctcacat ttgtgccacc taaaaaggag      6360
cgatttacat atgagttatg cagtttgtag aatgcaaaaa gtgaaatcag ctagatatat      6420
agtgccgtct aattttttgta tcaaatcact atctaattta gatacttgat aatgaatttt     6480
cttttttgat acgcccaact catcagccaa ctctttaatc gttttttaagt tctcactcat     6540
ggtttaagtc ctgcctttta accgtaggta gatattgctc gattgctttt ttcagatact      6600
tcgctacatt gcgtttagaa taggcttctt ttttgctaga tatataagac aagtggtctt     6660
tgaccccatt caatcctctt aattccttta actcgtcata caacggatag acgttctttt      6720
gcaaacctgc cataagtgcc gtgtccgtca tttcaagagg ggataagaga aagttttcaa      6780
tcaataatcg tgtgtacttg ctttccattg cctgttttaa taagtcagct tcatttcttg      6840
attttttcctc tttgtcggat tgataatctt tatcttctaa cttgtagctg ttatcatctg     6900
ctcgacgttt tttcgtgata tgaaagacaa tagaatcaat gcttcgtcct tttttttatct    6960
tgtcatacgt cacgttaaaa gaggtgtttt cgttaatttc ttctattggt tcttttaaaa      7020
ctctatgttc taatctatca aagcgggggt attcatcaac tgtatccgtc atttctcgta      7080
attctcgcat tgaaatggta ggattgcggt aggcttccac ttgttcttct ctccgtccgc     7140
ccttataact ataatgctcg tattggttat aattcatgga taaccaacgg tacaagataa      7200
tagagtattt gctattcagc tctgcaatat cagacaaagc atgttgcgtg aaattttgtt     7260
ttagattaat taagtagggc atgatttcac gatgaaattc aatttttacg tcatcatgat     7320
aatctgtcca ctcgacatat ggaatgggaa caatactcct aaatttaaat cctttaccta     7380
cttcttcttt aatttgaaaa aaggcttgtt tttgcatatt ctctactgct tgtttaaaac      7440
gactatgttt gtcattatca gataccttaa aaaaggcaaa caattcttct tttgagagat     7500
aaaccgtatg atctttgggt ggttcttcgg tattaataca agacacggct aattcaaaca      7560
ttttcagtgg cgttttatcc attttcgcaa tactggtaat taaagaatta tgttccacta     7620
cttttcgttt tgacaattcg ttcaaggttt gcacctgctt ttgattaggt tcattttttg     7680
atatactaga catagaaaac tgctcctttg tgagtgagtt tagataagca tgaagaaaca      7740
cttttcgtag agagattctt catgcttttta ttatatcatt ataccaac gaaacaaaca      7800
aagaagttgg tatatgcaca gttttttgtt ggtgtatgca cagttttttg ttggtatata     7860
cacagttttt tgttggtata taattctata aagccttgaa aatattgatt tttttttgac     7920
gcaaaagaat aaaagattaa aatatataag ataaatatat aataggcttc gcctattttt      7980
tatttttttc aaaaatttaa aaccaaaggt caaagtcatc aaaaaaagga gtgagcgagt     8040
gaacgctcac atttttacttg cagcgttcac tcgctaaaag aaaagatcaa aaccgctttt     8100
aggaatttat tggattccct ctaattgctc atataagctg ttttaactgt ttgactagct     8160
aaatactcat atcatgcaat caagcgtctt acagacggtc agggcaagcc ctaacaaccc     8220
ttaaatggaa aactgatact ttgtttaact tgttttttttt acaacttaca acaagctatt    8280
caattcaaaa tcaatttaaa ccccttaaaa agctcgttta agcattctta atgctcccttt    8340
tgaacaaata gacagtttcg aattaaagtc gcttaaatcg agttttagaa cgttttaaaa     8400
tagaatgatg aaaaactaaa aagtttcaaa cgctggtcgg cttgtttcgt aaaaaaagag     8460
tgcaatgcgc acttacacat cactctaaaa acgagtgatg taatggctaa aaatcgtgta    8520
```

```
ttagaagttg cttatcacaa caacaaaatt tcatgatagt agcttctctt aaatgagtga   8580
gtctttgttt caatttgtga tacattttc tgatccatca ataacttact caaagataaa    8640
atgcctcagc gctcattcct caatcgccct ttgtcattga ttttgtaata agcattgcgc   8700
cctattcggt tacaatcctc acaacaaaat agaccatata aaaccataaa tactgcaagc   8760
tatcacattg taatacaaaa cacttcgttc ttgtattaca atgtggcttg aaaagggga    8820 agtttcactt tcccctttta tcccctttgg attgtgtcga tttgctttac acaaacgcca   8880
cctgcccatt ttataaaaat aaaatgggca aaagatctgc ctcgcgcgtt tcggtgatga   8940
cggtgaaaac ctctgacaca tgcagctccc ggagacggtc acagcttgtc tgtaagcgga   9000
tgccgggagc agacaagccc gtcagggcgc gtcagcgggt gttggcgggt gtcggggcgc   9060
agccatgacc cagtcacgta gcgatagcgg agtgtatact ggcttaacta tgcggcatca   9120
gagcagattg tactgagagt gcaccatatg cggtgtgaaa taccgcacag atgcgtaagg   9180
agaaaatacc gcatcaggcg ctcttccgct tcctcgctca ctgactcgct gcgctcggtc   9240
gttcggctgc ggcgagcggt atcagctcac tcaaaggcgg taatacggtt atccacagaa   9300
tcaggggata acgcaggaaa gaacatgtga gcaaaaggcc agcaaaaggc caggaaccgt   9360
aaaaaggccg cgttgctggc gtttttccat aggctccgcc cccctgacga gcatcacaaa   9420
aatcgacgct caagtcagag gtggcgaaac ccgacaggac tataaagata ccaggcgttt   9480
ccccctggaa gctccctcgt gcgctctcct gttccgaccc tgccgcttac cggatacctg   9540
tccgcctttc tcccttcggg aagcgtggcg ctttctcata gctcacgctg taggtatctc   9600
agttcggtgt aggtcgttcg ctccaagctg ggctgtgtgc acgaaccccc cgttcagccc   9660
gaccgctgcg ccttatccgg taactatcgt cttgagtcca acccggtaag acacgactta   9720
tcgccactgg cagcagccac tggtaacagg attagcagag cgaggtatgt aggcggtgct   9780
acagagttct tgaagtggtg gcctaactac ggctacacta aggacagt atttggtatc     9840 tgcgctctgc tgaagccagt taccttcgga aaaagagttg gtagctcttg atccggcaaa   9900
caaaccaccg ctggtagcgg tggttttttt gtttgcaagc agcagattac gcgcagaaaa   9960
aaaggatctc aagaagatcc tttgatcttt tctacggggt ctgacgctca gtggaacgaa  10020
aactcacgtt aagggatttt ggtcatgaga ttatcaaaaa ggatcttcac ctagatcctt  10080
ttaaattaaa aatgaagttt taaatcaatc taaagtatat atgagtaaac ttggtctgac  10140
agttaccaat gcttaatcag tgaggcacct atctcagcga tctgtctatt tcgttcatcc  10200
atagttgcct gactccccgt cgtgtagata actacgatac gggagggctt accatctggc  10260
cccagtgctg caatgatacc gcgagaccca cgctcaccgg ctccagattt atcagcaata  10320
aaccagccag ccgaagggc cgagcgcaga agtggtcctg caactttatc cgcctccatc   10380
cagtctatta attgttgccg ggaagctaga gtaagtagtt cgccagttaa tagtttgcgc  10440
aacgttgttg ccattgctgc ag                                           10462
```

<210> SEQ ID NO 2
<211> LENGTH: 1992
<212> TYPE: DNA
<213> ORGANISM: artificial
<220> FEATURE:
<223> OTHER INFORMATION: nucleotide sequence of the P23 promoter

<400> SEQUENCE: 2

```
ctgcaggaaa agccctgaca acgcttgttc ctaaaaagga ataagcgttc ggtcagtaaa    60
```

```
taatagaaat aaaaaatcag acctaagact gatgacaaaa agagaaaatt ttgataaaat    120
agtcttagaa ttaaattaaa aagggaggcc aaatataatg aaaaatatga atgacaatga    180
tgttggtacc atcccttta aagtttattt gataaaattg taaatataat agctattaat     240
tggttatttt atttgtatat cgctagaatt agttagcaaa tttaacctac ggaggttgat    300
aaaaatgaag aagtacaaga agttttgttt tttaggtatt gggttattac ctttggtatt    360
agctagttgt gggacaaata ctgccacaaa agattcacaa gatgcaacag aaaaaaaagt    420
agaacaggta gcgactttga ctgcagggac acctgtccaa agtttagacc cagcaactgc    480
tgtagatcaa acgagtataa ctttattagc caatgtgatg gaggggttgt atcgattaga    540
tgaaaaaaat caaccgcaac cagccattgc agctggtcaa ccaaaagtat cgaataatgg    600
caaaacttat accattgtga ttagagatgg cgctaagtgg tctgatggta cacaaataac    660
tgctagtgat tttgtggccg cgtggcaaag agttgtagat cctaaaacag tttctccaaa    720
tgtggaactg ttttctgcta taaaaaatgc caaagaaatt gcttcaggaa acaagcaaa     780
agatacttta gcagtgaaaa gtattggtga aaaacatta gaaatcgaat tagttgaacc     840
aacaccttat tttactgatc tgttatcctt aaccgcttac tatccagtac agcagaaagc    900
aattaaagag tatgggaaag actatggggt ttctcaaaaa gcaattgtaa caaatggagc    960
atttaactta acaaacttag agggagtagg aacttctgat aagtggacga tttctaaaaa   1020
taaagagtac tgggatcaaa agatgtttc tatggataaa attaatttc aagtcgtcaa     1080
agaaattaat acaggaataa atttgtataa tgatgggcaa ttagatgagg cgcctttagc   1140
tggtgaatat gcaaacaat acaagaaaga taaagaatat caacaacat taatggctaa    1200
tacaatgttt ttagaaatga accaaactgg ggaaataag cttttacaaa acaaaaatgt    1260
ccgaaaagcg attaactatg caattgatcg ggaaagtcta gttaaaaaat tactagataa   1320
tgggtccgtt gcttctgttg gcgtagtacc aaaagaaatg gcctttaatc cggtaaataa   1380
aaagatttt gctaatgaaa aattagttga atttaacaaa aaacaagcag aagagtattg    1440
ggataaggct aaaaagaaa ttgatttatc caaaaatact tctttagatt tacttgtaag    1500
tgatggagag tttgaaaaaa aggcaggaga atttctgcaa ggacagttgc aagatagctt   1560
agaaggattg aaggttactg tgacgccaat tcctgcaaat gtctttatgg aacgcctaac   1620
aaaaaaggat tttactttga gcctaagtgg atggcaagct gattatgcag accctattag   1680
cttttagca aactttgaaa caaatagtcc aatgaatcat ggtggatatt caaataaaaa    1740
ttatgatgaa ttgctaaagg attcttcttc taaacgttgg caagaattga aaaagctga    1800
aaaattgttg atcaatgata tggggtcgt tccaattttt caagttggaa cagcaaaatt    1860
agaaaaaagt aaaataaaaa atgtttaat gcattcaata ggagcaaaat atgactacaa    1920
aaaaatgaga atagagaagt aatggagggt atatggaatt agttcgtcgc gtttttataa   1980
ggtaccctgc ag                                                       1992
```

<210> SEQ ID NO 3
<211> LENGTH: 317
<212> TYPE: PRT
<213> ORGANISM: Enterococcus faecalis

<400> SEQUENCE: 3

Met Phe Lys Ile Gly Ser Val Leu Lys Gln Ile Arg Gln Glu Leu Asn
1               5                   10                  15

Tyr His Gln Ile Asp Leu Tyr Ser Gly Ile Met Ser Lys Ser Val Tyr
            20                  25                  30

Ile Lys Val Glu Ala Asp Ser Arg Pro Ile Ser Val Glu Glu Leu Ser
             35                  40                  45

Lys Phe Ser Glu Arg Leu Gly Val Asn Phe Phe Glu Ile Leu Asn Arg
 50                  55                  60

Ala Gly Met Asn Thr Lys Ser Val Asn Glu Thr Gly Lys Glu Lys Leu
 65                  70                  75                  80

Leu Ile Ser Lys Ile Phe Thr Asn Pro Asp Leu Phe Asp Lys Asn Phe
                 85                  90                  95

Gln Arg Ile Glu Pro Lys Arg Leu Thr Ser Leu Gln Tyr Phe Ser Ile
             100                 105                 110

Tyr Leu Gly Tyr Ile Ser Ile Ala His His Tyr Asn Ile Glu Val Pro
             115                 120                 125

Thr Phe Asn Lys Thr Ile Thr Ser Asp Leu Lys His Leu Tyr Asp Lys
 130                 135                 140

Arg Thr Thr Phe Phe Gly Ile Asp Tyr Glu Ile Val Ser Asn Leu Leu
 145                 150                 155                 160

Asn Val Leu Pro Tyr Glu Val Ser Ser Ile Ile Lys Pro Met Tyr
                 165                 170                 175

Pro Ile Val Asp Ser Phe Gly Lys Asp Tyr Asp Leu Thr Ile Gln Thr
             180                 185                 190

Val Leu Lys Asn Ala Leu Thr Ile Ser Ile Met Asn Arg Asn Leu Lys
             195                 200                 205

Glu Ala Gln Tyr Tyr Ile Asn Gln Phe Glu His Leu Lys Thr Ile Lys
 210                 215                 220

Asn Ile Ser Ile Asn Gly Tyr Tyr Asp Leu Glu Ile Asn Tyr Leu Lys
225                 230                 235                 240

Gln Ile Tyr Gln Phe Leu Thr Asp Lys Asn Ile Asp Ser Tyr Leu Asn
             245                 250                 255

Ala Val Asn Ile Ile Asn Ile Phe Lys Ile Ile Gly Lys Glu Asp Ile
             260                 265                 270

His Arg Ser Leu Val Glu Glu Leu Thr Lys Ile Ser Ala Lys Glu Lys
             275                 280                 285

Phe Thr Pro Pro Lys Glu Val Thr Met Tyr Tyr Glu Asn Tyr Val Ala
 290                 295                 300

Ile Glu Asn Asn Pro Ile Pro Glu Ile Lys Glu Gln Ser
305                 310                 315

<210> SEQ ID NO 4
<211> LENGTH: 545
<212> TYPE: PRT
<213> ORGANISM: Enterococcus faecalis

<400> SEQUENCE: 4

Met Lys Lys Tyr Lys Lys Phe Cys Phe Leu Gly Ile Gly Leu Leu Pro
 1                   5                  10                  15

Leu Val Leu Ala Ser Cys Gly Thr Asn Thr Ala Thr Lys Asp Ser Gln
             20                  25                  30

Asp Ala Thr Glu Lys Lys Val Glu Gln Val Ala Thr Leu Thr Ala Gly
             35                  40                  45

Thr Pro Val Gln Ser Leu Asp Pro Ala Thr Ala Val Asp Gln Thr Ser
             50                  55                  60

Ile Thr Leu Leu Ala Asn Val Met Glu Gly Leu Tyr Arg Leu Asp Glu
 65                  70                  75                  80

Lys Asn Gln Pro Gln Pro Ala Ile Ala Ala Gly Gln Pro Lys Val Ser

```
                         85                  90                  95
Asn Asn Gly Lys Thr Tyr Thr Ile Val Ile Arg Asp Gly Ala Lys Trp
                100                 105                 110

Ser Asp Gly Thr Gln Ile Thr Ala Ser Asp Phe Val Ala Ala Trp Gln
            115                 120                 125

Arg Val Val Asp Pro Lys Thr Val Ser Pro Asn Val Glu Leu Phe Ser
    130                 135                 140

Ala Ile Lys Asn Ala Lys Glu Ile Ala Ser Gly Lys Gln Ala Lys Asp
145                 150                 155                 160

Thr Leu Ala Val Lys Ser Ile Gly Glu Lys Thr Leu Glu Ile Glu Leu
                165                 170                 175

Val Glu Pro Thr Pro Tyr Phe Thr Asp Leu Leu Ser Leu Thr Ala Tyr
            180                 185                 190

Tyr Pro Val Gln Gln Lys Ala Ile Lys Glu Tyr Gly Lys Asp Tyr Gly
        195                 200                 205

Val Ser Gln Lys Ala Ile Val Thr Asn Gly Ala Phe Asn Leu Thr Asn
    210                 215                 220

Leu Glu Gly Val Gly Thr Ser Asp Lys Trp Thr Ile Ser Lys Asn Lys
225                 230                 235                 240

Glu Tyr Trp Asp Gln Lys Asp Val Ser Met Asp Lys Ile Asn Phe Gln
                245                 250                 255

Val Val Lys Glu Ile Asn Thr Gly Ile Asn Leu Tyr Asn Asp Gly Gln
            260                 265                 270

Leu Asp Glu Ala Pro Leu Ala Gly Glu Tyr Ala Lys Gln Tyr Lys Lys
        275                 280                 285

Asp Lys Glu Tyr Ser Thr Thr Leu Met Ala Asn Thr Met Phe Leu Glu
    290                 295                 300

Met Asn Gln Thr Gly Glu Asn Lys Leu Leu Gln Asn Lys Asn Val Arg
305                 310                 315                 320

Lys Ala Ile Asn Tyr Ala Ile Asp Arg Glu Ser Leu Val Lys Lys Leu
                325                 330                 335

Leu Asp Asn Gly Ser Val Ala Ser Val Gly Val Val Pro Lys Glu Met
            340                 345                 350

Ala Phe Asn Pro Val Asn Lys Lys Asp Phe Ala Asn Glu Lys Leu Val
        355                 360                 365

Glu Phe Asn Lys Lys Gln Ala Glu Glu Tyr Trp Asp Lys Ala Lys Lys
    370                 375                 380

Glu Ile Asp Leu Ser Lys Asn Thr Ser Leu Asp Leu Leu Val Ser Asp
385                 390                 395                 400

Gly Glu Phe Glu Lys Lys Ala Gly Glu Phe Leu Gln Gly Gln Leu Gln
                405                 410                 415

Asp Ser Leu Glu Gly Leu Lys Val Thr Val Thr Pro Ile Pro Ala Asn
            420                 425                 430

Val Phe Met Glu Arg Leu Thr Lys Lys Asp Phe Thr Leu Ser Leu Ser
        435                 440                 445

Gly Trp Gln Ala Asp Tyr Ala Asp Pro Ile Ser Phe Leu Ala Asn Phe
    450                 455                 460

Glu Thr Asn Ser Pro Met Asn His Gly Gly Tyr Ser Asn Lys Asn Tyr
465                 470                 475                 480

Asp Glu Leu Leu Lys Asp Ser Ser Lys Arg Trp Gln Glu Leu Lys
                485                 490                 495

Lys Ala Glu Lys Leu Leu Ile Asn Asp Met Gly Val Val Pro Ile Phe
            500                 505                 510
```

-continued

```
Gln Val Gly Thr Ala Lys Leu Glu Lys Ser Lys Ile Lys Asn Val Leu
        515                 520                 525
Met His Ser Ile Gly Ala Lys Tyr Asp Tyr Lys Lys Met Arg Ile Glu
        530                 535                 540
Lys
545

<210> SEQ ID NO 5
<211> LENGTH: 1220
<212> TYPE: DNA
<213> ORGANISM: artificial
<220> FEATURE:
<223> OTHER INFORMATION: nucleotide sequence of pheromone-responsive
      region pPD1

<400> SEQUENCE: 5
agttaatcta ttttttttgtg gtcaaaattt ttggggtcta atacttgtcc atcatcgtca      60
agaacaccaa atatttgttt tgcttttttca tcatcacttt tagaaatgat tgtttgtaag    120 ttttttatgga attgctcaac atattcaggg cttttccactt gtttcaatat ttcaacatac    180
gagaatactt tcataaatatg ctctatatct ccagaagtaa agtatagaag catatttctt    240
gaagctatga aacttaattt atatttataa ctagtgtaat ttgataacaa agtttcaaag    300
tgatttagaa gtataaagca agaactgtaa tcctttgtaa atatacttag agcaattgca    360
ttagacaagg ataaacaagc tgtatcttta atctgctcgt cactatcttc acgtaaagga    420
aatagttgct ctatcaatgt ctgaagatca gagtaaggga atatagtgca tagattagaa    480
agaattttat agtgatacaa tacaaatctt ttgcttgatg aaaacatctt ttttatatca    540
gctaaatctt gtttatccac aggaataatt tctgaaatca aactagaggt ttgcaatttt    600
ataagtaaat ataaattcat gtattttaac gaagtaaatt tttcatgtat agattttttga    660 taaagagagt agagttcttg attgtattct gaatcaggat tttgttgaat ttttgaaaga    720
acaaaataat atgtttctaa atctttatca aaaacacttt taaaatcttc attacaagtt    780
ctaattattt caggtattgt taaattactt ctatctgcaa gaattggcaa atcagcaatt    840
tttaaaaaat gttcattatg gttttcaaaa aggcttgctg aattacgctg aaaaatacct    900
tcataaaact tagcttgaga taatttctcg cttttttcttt gtattttcat taattcattt    960
aaatgcatat attcaactcc tataaatgta ttctgaatat gacgaaaatc ggcaaaaaaa   1020
agaaaataaa taaaaaatga attatttttc ccggaaacgt ctttttttaaa atacatatac   1080 ttgtaatgag taaactttaa tgctatagta gtaactgtaa tgaatagtta ctaagtgagg   1140
taaatttaat gaaacaacaa aaaaaacata tagctgcatt attgtttgca ctaatattaa   1200
ctcttgtttc ttaaaaaaaa                                                1220

<210> SEQ ID NO 6
<211> LENGTH: 1220
<212> TYPE: DNA
<213> ORGANISM: artificial
<220> FEATURE:
<223> OTHER INFORMATION: nucleotide sequence of pheromone-responsive
      region pAD1

<400> SEQUENCE: 6
ctagagtagt tactctagtc ttttggttat tttcttttcg tttagtttta tatgattatt      60
ttctttagta agtaaagtat ctggtttact catagaacca ttattttttt ttgagatcat    120
tagataaatg ttatctttca ttaattttgc tagctcgaca ttttctaagt ctcctaatag    180
```

```
atcgacatat ttaattgagt tatttaaaga atccatgttg tttgttaaaa agtaaccaac    240
taaattataa gttattaaat aatttagttt atacttatat gacgggaatt tttgcaataa    300
atcattgtag atattcagaa cttctgtaca actttcaaaa tctcggtttt gaacgagttt    360
agtagtaatg ttttcaagta aatagtatgc tgcttcacta gtaactgttg gagcgtttga    420
atctaatgga aatagactag atagaaacgg ttgcaattct ttgtaagaaa atacaagaga    480
tagattagta acaattttat agtcgtaaag agtaaacttt tgttttgata aaatcatttt    540
ttttaactca gataaatctt gtgagtctgt agggacaatt cttgaatcgt attcagaaca    600
ttggattttt attattaagt aaagattcca atatattata gaatgttctt ttagctctat    660 agacttttg tataatttgt aaatgtagtc tttatttct ttttcggtat tattctggaa    720
tatatcaaac aatgaattta agtcttcgtc gtaaggagaa ataaattctt ctttagcata    780
atgaattatt tctaagatac tcatcatgct tctatctgat aaaacaggta aatctttaac    840
tttgagatca tgcgtgttgt gtacctcaaa agaagaggca gctctttttt tgaatattcc    900
ttcataaaat tcttcttgag taaaattata gagttttcgc tgttctttga atagttcgta    960
aagaaacatt ttgaaatact ccttccgagg cgcaaaaaag tgcattcgtg gaatgatttt   1020 ttggttttt tattatgtaa taaatttttt tgatgaaaaa gcgcaaattt ttgcatttt   1080 gtttatttt atttaatct atgctattat taatttgtaa gttaagttta aataagagga   1140
gagctattag aatgagcaaa cgagctatga aaaaaattat tccattgata actttatttg   1200
ttgtcacact tgtaggataa                                              1220
```

<210> SEQ ID NO 7
<211> LENGTH: 1282
<212> TYPE: DNA
<213> ORGANISM: artificial
<220> FEATURE:
<223> OTHER INFORMATION: nucleotide sequence of pheromone-responsive
      region pAM373

<400> SEQUENCE: 7

```
ctaagtttta actatatttg gaggaattgt tgcatataa tcaatactgc ttttcgtatt     60
agcaattgca gctataatat ctttagtgtt atcttctttt tcgattatag aaacagtagc    120
ttctttcatt ctatcagcta gagaggaaga aggcggttca cagctatcaa taatattaat    180
tatttgtaaa gcttcagtta atttactaga attattgatc ttatctgtaa gaaaatcaag    240
caatgctcta tcgtgtaaac aaatgagttt aaatttgtat gatggattaa cttttaattg    300
ttcttcaaaa ttattaatag ctaatttagc tttattgtag tctttatttt ttatgtgctt    360
agttgttaag tttgttaaag caaggtaagc aggatatagt atctcttcgg gaacattatt    420
tgctaaaggg tatagtacat caaacataaa gtttaaatca ttgacagtaa ataaaggtag    480
cgttataaga ttagctaata ctttataatc ggaagaagta taaagcttgc gtgttctata    540
tatttttttt aggtccatga gatctgcttt gtctacttct aaaattttat ctgtaaattc    600
tgaacaagaa atttttataa gcaaatacaa attaaaatat tttaaagagt agtatttagg    660
ttcaatacac tgcatatata tggcagtaat atcttttgtg acttcattta tttcagattt    720
ttcttctaac gattgaaggc tggcatattt atttagaaag gagtctctta gtttatcaaa    780
atcagtgtgt aatgtatcag aggaatagaa taaaatctcc tcgcaagtta agtctaaacg    840
atcagctaga atgggaatgc aagatagttt gattgaagtt ttattctttt caaatttatc    900
tgcagtactt cttgataaaa catctttgta aaaagttgtt tgagataaat ttagattatt    960
```

```
acgtgtatgc tttaaaaaat cgtttataaa cataaaaaaa cctccaatat tcatatgtgt    1020
aaaaaaaacg catttttgtt acttttttga tgattttcta tgtaatttca gattttttt     1080 caaaatgatg tatgtttttt atacattgta ttttactgaa taaaatcttg tggtatactt    1140
attttgtaag aattattgag aggggggaaat ccacttgaaa aaagagttaa ttttaatttt   1200
aaagtggttg acaccaatag gtttaagtat ttttacttta gtagcataac attttttgtaa  1260 atggctctgt aatttttta tg                                              1282

<210> SEQ ID NO 8
<211> LENGTH: 1847
<212> TYPE: DNA
<213> ORGANISM: artificial
<220> FEATURE:
<223> OTHER INFORMATION: nucleotide sequence of a tetracycline promoter
      and coding region encoding a tetracycline repressor (TET-PC64-GFP)

<400> SEQUENCE: 8
agatctcaaa taaaaagagt tggttgagat ttcaactagc tctttttatt ttaaattggt     60
accctcgagt tcatgaaaaa ctaaaaaaaa tattgacact ctatcattga tagagtataa    120
ttaaaataag ctctctatca ttgatagagt atgatggaac cgggaaaagg tggtgaacta    180
ctccatggta taatgaaaaa aaagattatc tcagctattt taatgtctac agtgatactt    240
tctgctgcag ccccgttgtc agtgtttac gctttaacat attgtcgtcg tgttttttgt    300
gttacagttt aaacgtatct agaagaattc cccggcttta ggtatagtgt gtatctcaat    360
ccttggtata ttgaaaagaa agactaaaaa ttgatagatt atatttcttc agaatgaatg    420
gtataatgaa gtaatgagta ctaaacaatc ggaggtaaaa tgatgtcacg tttagataaa    480
tcaaaagtta ttaattcagc tttagaatta ttaaatgaag ttggtattga aggtttaaca    540
acacgtaaat tagctcaaaa attaggtgtt gaacaaccaa cattatattg gcatgttaaa    600
aataaacgtg cttttattaga tgctttagct attgaaatgt tagatcgtca tcatacacat    660
ttttgtccat tagaaggtga atcatggcaa gatttttac gtaataatgc taaatcattt    720
cgttgtgctt tattatcaca tcgtgatggt gctaaagttc atttaggtac acgtccaaca    780
gaaaaacaat atgaaacatt agaaaatcaa ttagctttttt tatgtcaaca aggttttttca   840 ttagaaaatg ctttatatgc tttatcagct gttggtcatt ttacattagg ttgtgttta    900 gaagatcaag aacatcaagt tgctaaagaa gaacgtgaaa caccaacaac agattcaatg    960
ccaccattat tacgtcaagc tattgaatta ttttgatcatc aaggtgctga accagctttt   1020
ttatttggtt tagaattaat tatttgtggt ttagaaaaac aattaaaatg tgaatcaggt   1080
tcataagagc tctaatagcc atggtataat gcgtaaagga gaagaacttt tcactggagt   1140
tgtcccaatt cttgttgaat tagatggtga tgttaatggg cacaaatttt ctgtcagtgg   1200
agagggtgaa ggtgatgcaa catacggaaa acttaccctt aaatttattt gcactactgg   1260
aaaactacct gttccatggc caacacttgt cactactttg acttatggtg ttcaatgctt   1320
ttcaagatac ccagatcata tgaaacggca tgacttttc aagagtgcca tgcccgaagg   1380
ttatgtacag gaaagaacta tatttttcaa agatgacggg aactacaaga cacgtgctga   1440
agtcaagttt gaaggtgata cccttgttaa tagaatcgag ttaaaggta ttgattttaa    1500 agaagatgga acattcttg gacacaaatt ggaatacaac tataactcac acaatgtata    1560
catcatggca gacaaacaaa agaatggaat caaagttaac ttcaaaatta gacacaacat    1620
tgaagatgga agcgttcaac tagcagacca ttatcaacaa aatactccaa ttggcgatgg    1680
```

```
ccctgtcctt ttaccagaca accattacct gtccacacaa tctgcccttt cgaaagatcc    1740
caacgaaaag agagaccaca tggtccttct tgagtttgta acagctgctg ggattacaca    1800
tggcatggat gaactataca aataaacgta tctagataat gaagctt                  1847
```

<210> SEQ ID NO 9
<211> LENGTH: 1599
<212> TYPE: DNA
<213> ORGANISM: artificial
<220> FEATURE:
<223> OTHER INFORMATION: nucleotide sequence of a lactose promoter and
    coding region encoding a lactose repressor (LAC-ALYS)

<400> SEQUENCE: 9

```
agatctcaaa taaaaagagt tggttgagat ttcaactagc tcttttatt ttaaattggt      60 accgaattcg gtggaaacga ggtcatcatt tccttccgaa aaacggttg catttaaatc     120 ttacatatgt aatactttca attgtgagcg gataacaatt ccggatcaat caaatattca    180
aacggaggga gacgattttg ccatggtata atgaaaaaaa agattatctc agctatttta    240
atgtctacag tgatactttc tgctgcagcc ccgttgtcag gtgtttacgc tggttttaaaa   300 gatatttta aagctggttt aggttcatta gttaaaggta ttgctgctca tgttgctaat    360
taaacgtatc tagaagaatt ccccggcttt aggtatagtg tgtatctcaa tccttggtat    420
attgaaaaga aagactaaaa attgatagat tatatttctt cagaatgaat ggtataatga    480
agtaatgagt actaaacaat cggaggtaaa atgaaaccag ttacattata tgatgttgct    540
gaatatgctg gtgtttcata tcaaacagtt tctcgtgttg ttaatcaagc atcacatgtt    600
tcagctaaaa cacgtgaaaa agttgaagct gctatggctg aattaaatta tattccaaat    660
cgtgttgctc aacaattagc tggtaaacaa tcattattaa ttggtgttgc tacatcatca    720
ttagctttac atgctccatc acaaattgtt gctgctatta aatcacgtgc tgatcaatta    780
ggtgcttcag ttgttgtttc aatggttgaa cgttcaggtg ttgaagcatg taaagctgct    840
gttcataatt tattagctca acgtgtttca ggtttaatta ttaattatcc attagatgat    900
caagatgcta ttgctgttga agctgcttgt acaaatgttc agctttatt tttagatgtt    960 tcagatcaaa caccaattaa ttcaattatt ttttcacatg aagatggtac acgtttaggt   1020
gttgaacatt tagttgcttt aggtcatcaa caaattgctt tattagctgg tccattatca   1080
tcagtttcag ctcgtttacg tttagctggt tggcataaat atttaacacg taatcaaatt   1140
caacctattg ctgaacgtga aggtgattgg tcagctatgt caggttttca acaaacaatg   1200
caaatgttaa atgaaggtat tgttccaaca gctatgttag ttgctaatga tcaaatggct   1260
ttaggtgcta tgcgtgctat tacagaatca ggtttacgtg ttggtgctga tatttcagtt   1320
gttggttatg atgatacaga agattcatca tgttatattc caccattaac aacaattaaa   1380
caagattttc gtttattagg tcaaacatca gttgatcgtt tattacaatt atcacaaggt   1440
caagctgtta aaggtaatca attattacca gtttcattag ttaaacgtaa aacaacatta   1500
gctccaaata cacaaacagc ttcaccacgt gctttagctg attcattaat gcaattagct   1560
cgtcaagttt cacgtttaga atcaggtcaa taagagctc                            1599
```

<210> SEQ ID NO 10
<211> LENGTH: 1717
<212> TYPE: DNA
<213> ORGANISM: artificial
<220> FEATURE:
<223> OTHER INFORMATION: nucleotide sequence of a xylose promoter and coding region encoding a xylose repressor (XYL-A3APO)

<400> SEQUENCE: 10

```
agatctcaaa taaaaagagt tggttgagat ttcaactagc tcttttatt ttaaattggt      60
acccgaattc ggtggaaacg aggtcatcat ttccttccga aaaaacggaa cattgaaata    120
aacatttatt ttgtatatga tgagataaag ttagtttatt ggataaacaa actaactcaa    180
ttaagatagt tgatggataa acttgttcac ttaaatcaaa gggggaaatg acaaccatgg    240
tataatgaaa aaaagatta tctcagctat tttaatgtct acagtgatac tttctgctgc     300
agccccgttg tcaggtgttt acgctcgtcc agataaacca cgtccatatt taccacgtcc    360
acgtccacca cgtccagttc gttaaacgta tctagaagaa ttccccggct ttaggtatag    420
tgtgtatctc aatccttggt atattgaaaa gaaagactaa aaattgatag attatatttc    480
ttcagaatga atggtataat gaagtaatga gtactaaaca atcggaggta aaatgtttac    540
aaaacgtcat cgtattacat tattatttaa tgctaataaa gcctatgatc gtcaagttgt    600
tgaaggtgtt ggtgaatatt tacaagcctc acaatcagaa tgggatattt ttattgaaga    660
agattttcgt gctcgtattg ataaaattaa agattggtta ggtgatggtg ttattgctga    720
ttttgatgat aaacaaattg aacaagcctt agctgatgtt gatgttccaa ttgttggtgt    780
tggtggttca tatcatttag ctgaatcata tccaccagtt cattatattg ctacagataa    840
ttatgctta gttgaatcag cttttttaca tttaaaagaa aaaggtgtta atcgttttgc    900
tttttatggt ttaccagaat catcaggtaa acgttgggct acagaacgtg aatatgcttt    960
tcgtcaatta gttgctgaag aaaaatatcg tggtgttgtt tatcaaggtt tagaaacagc   1020
tccagaaaat tggcaacatg ctcaaaatcg tttagctgat tggttacaaa cattaccacc   1080
acaaacaggt attattgctg ttacagatgc tcgtgctcgt catattttac aagtttgtga   1140
acatttacat attccagttc cagaaaaatt atgtgttatt ggtattgata atgaagaatt   1200
aactcgttat ttatcacgtg ttgctttatc atcagttgct caaggtgctc gtcaaatggg   1260
ttatcaagct gctaaattat acatcgtttt attagataaa gaagaaatgc cattacaacg   1320
tattttagtt ccaccagttc gtgttattga acgtcgttca acagattatc gttcattaac   1380
agatccagct gttattcaag ctatgcatta tattcgtaat catgcttgta aaggtattaa   1440
agttgatcaa gttttagatg ctgttggtat ttcacgttca aatttagaaa acgttttaa    1500
agaagaagtt ggtgaaacaa ttcatgctat gattcatgct gaaaaattag aaaaagctcg   1560
ttcattatta atttcaacaa cattatcaat taatgaaatt tcacaaatgt gtggttatcc   1620
atcattacaa tatttttatt cagtttttaa aaaagcctat gatacaacac aaaagaata    1680
tcgtgatgtt aattcagaag ttatgttata agagctc                           1717
```

<210> SEQ ID NO 11  
<211> LENGTH: 47  
<212> TYPE: PRT  
<213> ORGANISM: Enterococcus faecium

<400> SEQUENCE: 11

```
Thr Thr His Ser Gly Lys Tyr Tyr Gly Asn Gly Val Tyr Cys Thr Lys
1               5                   10                  15

Asn Lys Cys Thr Val Asp Trp Ala Lys Ala Thr Thr Cys Ile Ala Gly
            20                  25                  30

Met Ser Ile Gly Gly Phe Leu Gly Gly Ala Ile Pro Gly Lys Cys
        35                  40                  45
```

<210> SEQ ID NO 12
<211> LENGTH: 44
<212> TYPE: PRT
<213> ORGANISM: Enterococcus faecium

<400> SEQUENCE: 12

Ala Thr Arg Ser Tyr Gly Asn Gly Val Tyr Cys Asn Asn Ser Lys Cys
1               5                   10                  15

Trp Val Asn Trp Gly Glu Ala Lys Glu Asn Ile Ala Gly Ile Val Ile
            20                  25                  30

Ser Gly Trp Ala Ser Gly Leu Ala Gly Met Gly His
        35                  40

<210> SEQ ID NO 13
<211> LENGTH: 44
<212> TYPE: PRT
<213> ORGANISM: Enterococcus hirae

<400> SEQUENCE: 13

Ala Thr Tyr Tyr Gly Asn Gly Leu Tyr Cys Asn Lys Glu Lys Cys Trp
1               5                   10                  15

Val Asp Trp Asn Gln Ala Lys Gly Glu Ile Gly Lys Ile Ile Val Asn
            20                  25                  30

Gly Trp Val Asn His Gly Pro Trp Ala Pro Arg Arg
        35                  40

<210> SEQ ID NO 14
<211> LENGTH: 18
<212> TYPE: PRT
<213> ORGANISM: pig

<400> SEQUENCE: 14

Arg Gly Gly Arg Leu Cys Tyr Cys Arg Arg Arg Phe Cys Val Cys Val
1               5                   10                  15

Gly Arg

<210> SEQ ID NO 15
<211> LENGTH: 12
<212> TYPE: PRT
<213> ORGANISM: artificial
<220> FEATURE:
<223> OTHER INFORMATION: peptide analog of pig protegrin-1 (PG-1)

<400> SEQUENCE: 15

Leu Thr Tyr Cys Arg Arg Arg Phe Cys Val Thr Val
1               5                   10

<210> SEQ ID NO 16
<211> LENGTH: 19
<212> TYPE: PRT
<213> ORGANISM: artificial
<220> FEATURE:
<223> OTHER INFORMATION: engineered antimicrobial peptide

<400> SEQUENCE: 16

Arg Pro Asp Lys Pro Arg Pro Tyr Leu Pro Arg Pro Arg Pro Pro Arg
1               5                   10                  15

Pro Val Arg

<210> SEQ ID NO 17
<211> LENGTH: 23
<212> TYPE: PRT

-continued

```
<213> ORGANISM: Alytes obstetricians

<400> SEQUENCE: 17

Gly Leu Lys Asp Ile Phe Lys Ala Gly Leu Gly Ser Leu Val Lys Gly
1               5                   10                  15

Ile Ala Ala His Val Ala Asn
            20

<210> SEQ ID NO 18
<211> LENGTH: 26
<212> TYPE: PRT
<213> ORGANISM: chicken

<400> SEQUENCE: 18

Arg Val Lys Arg Val Trp Pro Leu Val Ile Arg Thr Val Ile Ala Gly
1               5                   10                  15

Tyr Asn Leu Tyr Arg Ala Ile Lys Lys Lys
            20                  25

<210> SEQ ID NO 19
<211> LENGTH: 74
<212> TYPE: PRT
<213> ORGANISM: Escherichia coli

<400> SEQUENCE: 19

Ala Gly Asp Pro Leu Ala Asp Pro Asn Ser Gln Ile Val Arg Gln Ile
1               5                   10                  15

Met Ser Asn Ala Ala Trp Gly Pro Pro Leu Val Pro Glu Arg Phe Arg
            20                  25                  30

Gly Met Ala Val Gly Ala Ala Gly Gly Val Thr Gln Thr Val Leu Gln
        35                  40                  45

Gly Ala Ala Ala His Met Pro Val Asn Val Pro Ile Pro Lys Val Pro
    50                  55                  60

Met Gly Pro Ser Trp Asn Gly Ser Lys Gly
65                  70

<210> SEQ ID NO 20
<211> LENGTH: 88
<212> TYPE: PRT
<213> ORGANISM: Escherichia coli

<400> SEQUENCE: 20

Ala Ser Gly Arg Asp Ile Ala Met Ala Ile Gly Thr Leu Ser Gly Gln
1               5                   10                  15

Phe Val Ala Gly Gly Ile Gly Ala Ala Ala Gly Val Ala Gly Gly
            20                  25                  30

Ala Ile Tyr Asp Tyr Ala Ser Thr His Lys Pro Asn Pro Ala Met Ser
        35                  40                  45

Pro Ser Gly Leu Gly Gly Thr Ile Lys Gln Lys Pro Glu Gly Ile Pro
    50                  55                  60

Ser Glu Ala Trp Asn Tyr Ala Ala Gly Arg Leu Cys Asn Trp Ser Pro
65                  70                  75                  80

Asn Asn Leu Ser Asp Val Cys Leu
                85

<210> SEQ ID NO 21
<211> LENGTH: 11
<212> TYPE: PRT
<213> ORGANISM: Lactobacillus acidophilus
```

```
<400> SEQUENCE: 21

Asn Val Gly Val Leu Asn Pro Pro Leu Val
1               5                   10

<210> SEQ ID NO 22
<211> LENGTH: 11
<212> TYPE: PRT
<213> ORGANISM: Lactobacillus acidophilus

<400> SEQUENCE: 22

Asn Val Gly Val Leu Asn Pro Pro Met Leu Val
1               5                   10

<210> SEQ ID NO 23
<211> LENGTH: 11
<212> TYPE: PRT
<213> ORGANISM: Lactobacillus acidophilus

<400> SEQUENCE: 23

Asn Val Gly Val Leu Leu Pro Pro Pro Leu Val
1               5                   10

<210> SEQ ID NO 24
<211> LENGTH: 11
<212> TYPE: PRT
<213> ORGANISM: Lactobacillus acidophilus

<400> SEQUENCE: 24

Asn Val Gly Val Leu Leu Pro Pro Met Leu Val
1               5                   10

<210> SEQ ID NO 25
<211> LENGTH: 8
<212> TYPE: PRT
<213> ORGANISM: Lactobacillus acidophilus

<400> SEQUENCE: 25

Asn Pro Ser Arg Gln Glu Arg Arg
1               5

<210> SEQ ID NO 26
<211> LENGTH: 5
<212> TYPE: PRT
<213> ORGANISM: Lactobacillus acidophilus

<400> SEQUENCE: 26

Pro Asp Glu Asn Lys
1               5

<210> SEQ ID NO 27
<211> LENGTH: 289
<212> TYPE: PRT
<213> ORGANISM: Enterococcus faecalis

<400> SEQUENCE: 27

Met Ala Gly Glu Val Phe Ser Ser Leu Ile Thr Ser Val Asn Pro Asn
1               5                   10                  15

Pro Met Asn Ala Gly Ser Arg Asn Gly Ile Pro Ile Asp Thr Ile Ile
                20                  25                  30

Leu His His Asn Ala Thr Thr Asn Lys Asp Val Ala Met Asn Thr Trp
            35                  40                  45

Leu Leu Gly Gly Gly Ala Gly Thr Ser Ala His Tyr Glu Cys Thr Pro
        50                  55                  60
```

```
Thr Glu Ile Ile Gly Cys Val Gly Glu Gln Tyr Ser Ala Phe His Ala
 65                  70                  75                  80

Gly Gly Thr Gly Gly Ile Asp Val Pro Lys Ile Ala Asn Pro Asn Gln
             85                  90                  95

Arg Ser Ile Gly Ile Glu Asn Val Asn Ser Ser Gly Ala Pro Asn Trp
            100                 105                 110

Ser Val Asp Pro Arg Thr Ile Thr Asn Cys Ala Arg Leu Val Ala Asp
        115                 120                 125

Ile Cys Thr Arg Tyr Gly Ile Pro Cys Asp Arg Gln His Val Leu Gly
130                 135                 140

His Asn Glu Val Thr Ala Thr Ala Cys Pro Gly Gly Met Asp Val Asp
145                 150                 155                 160

Glu Val Val Arg Gln Ala Gln Gln Phe Met Ala Gly Gly Ser Asn Asn
                165                 170                 175

Ala Val Lys Pro Glu Pro Ser Lys Pro Thr Pro Ser Lys Pro Ser Asn
            180                 185                 190

Asn Lys Asn Lys Glu Gly Val Ala Thr Met Tyr Cys Leu Tyr Glu Arg
        195                 200                 205

Pro Ile Asn Ser Lys Thr Gly Val Leu Glu Trp Asn Gly Asp Ala Trp
210                 215                 220

Thr Val Met Phe Cys Asn Gly Val Asn Cys Arg Arg Val Ser His Pro
225                 230                 235                 240

Asp Glu Met Lys Val Ile Glu Asp Ile Tyr Arg Lys Asn Asn Gly Lys
                245                 250                 255

Asp Ile Pro Phe Tyr Ser Gln Lys Glu Trp Asn Lys Asn Ala Pro Trp
            260                 265                 270

Tyr Asn Arg Leu Glu Thr Val Cys Pro Val Val Gly Ile Thr Lys Lys
        275                 280                 285

Ser

<210> SEQ ID NO 28
<211> LENGTH: 410
<212> TYPE: PRT
<213> ORGANISM: Enterobacteria phage F1

<400> SEQUENCE: 28

Met Ser Asn Ile Asn Met Glu Thr Ala Ile Ala Asn Met Tyr Ala Leu
 1                   5                  10                  15

Lys Ala Arg Gly Ile Thr Tyr Ser Met Asn Tyr Ser Arg Thr Gly Ala
                 20                  25                  30

Asp Gly Thr Gly Asp Cys Ser Gly Thr Val Tyr Asp Ser Leu Arg Lys
             35                  40                  45

Ala Gly Ala Ser Asp Ala Gly Trp Val Leu Asn Thr Asp Ser Met His
         50                  55                  60

Ser Trp Leu Glu Lys Asn Gly Phe Lys Leu Ile Ala Gln Asn Lys Glu
 65                  70                  75                  80

Trp Ser Ala Lys Arg Gly Asp Val Val Ile Phe Gly Lys Lys Gly Ala
                 85                  90                  95

Ser Gly Gly Ser Ala Gly His Val Val Ile Phe Ile Ser Thr Gln
            100                 105                 110

Ile Ile His Cys Thr Trp Lys Ser Ala Thr Ala Asn Gly Val Tyr Val
        115                 120                 125

Asp Asn Glu Ala Thr Thr Cys Pro Tyr Ser Met Gly Trp Tyr Val Tyr
130                 135                 140
```

```
Arg Leu Asn Gly Gly Ser Thr Pro Lys Pro Asn Thr Lys Lys Val
145                 150                 155                 160

Lys Val Leu Lys His Ala Thr Asn Trp Ser Pro Ser Lys Gly Ala
                165                 170                 175

Lys Met Ala Ser Phe Val Lys Gly Gly Thr Phe Glu Val Lys Gln Gln
            180                 185                 190

Arg Pro Ile Ser Tyr Ser Tyr Ser Asn Gln Glu Tyr Leu Ile Val Asn
            195                 200                 205

Lys Gly Thr Val Leu Gly Trp Val Leu Ser Gln Asp Ile Glu Gly Gly
210                 215                 220

Tyr Gly Ser Asp Arg Val Gly Gly Ser Lys Pro Lys Leu Pro Ala Gly
225                 230                 235                 240

Phe Thr Lys Glu Glu Ala Thr Phe Ile Asn Gly Asn Ala Pro Ile Thr
            245                 250                 255

Thr Arg Lys Asn Lys Pro Ser Leu Ser Ser Gln Thr Ala Thr Pro Leu
            260                 265                 270

Tyr Pro Gly Gln Ser Val Arg Tyr Leu Gly Trp Lys Ser Ala Glu Gly
            275                 280                 285

Tyr Ile Trp Ile Tyr Ala Thr Asp Gly Arg Tyr Ile Pro Val Arg Pro
290                 295                 300

Val Gly Lys Glu Ala Trp Gly Thr Phe Lys Gln Asp Ile Glu Gly Gly
305                 310                 315                 320

Tyr Gly Ser Asp Arg Val Gly Gly Ser Lys Pro Lys Leu Pro Ala Gly
            325                 330                 335

Phe Thr Lys Glu Glu Ala Thr Phe Ile Asn Gly Asn Ala Pro Ile Thr
            340                 345                 350

Thr Arg Lys Asn Lys Pro Ser Leu Ser Ser Gln Thr Ala Thr Pro Leu
            355                 360                 365

Tyr Pro Gly Gln Ser Val Arg Tyr Leu Gly Trp Lys Ser Ala Glu Gly
            370                 375                 380

Tyr Ile Trp Ile Tyr Ala Thr Asp Gly Arg Tyr Ile Pro Val Arg Pro
385                 390                 395                 400

Val Gly Lys Glu Ala Trp Gly Thr Phe Lys
            405                 410
```

<210> SEQ ID NO 29
<211> LENGTH: 328
<212> TYPE: PRT
<213> ORGANISM: Enterobacteria phage EFAP-1

<400> SEQUENCE: 29

```
Met Lys Leu Lys Gly Ile Leu Leu Ser Val Val Thr Thr Phe Gly Leu
1               5                   10                  15

Leu Phe Gly Ala Thr Asn Val Gln Ala Tyr Glu Val Asn Asn Glu Phe
            20                  25                  30

Asn Leu Gln Pro Trp Glu Gly Ser Gln Gln Leu Ala Tyr Pro Asn Lys
        35                  40                  45

Ile Ile Leu His Glu Thr Ala Asn Pro Arg Ala Thr Gly Arg Asn Glu
    50                  55                  60

Ala Thr Tyr Met Lys Asn Asn Trp Phe Asn Ala His Thr Thr Ala Ile
65                  70                  75                  80

Val Gly Asp Gly Gly Ile Val Tyr Lys Val Ala Pro Glu Gly Asn Val
                85                  90                  95

Ser Trp Gly Ala Gly Asn Ala Asn Pro Tyr Ala Pro Val Gln Ile Glu
```

```
            100                 105                 110
Leu Gln His Thr Asn Asp Pro Glu Leu Phe Lys Ala Asn Tyr Lys Ala
        115                 120                 125

Tyr Val Asp Tyr Thr Arg Asp Met Gly Lys Lys Phe Gly Ile Pro Met
    130                 135                 140

Thr Leu Asp Gln Gly Gly Ser Leu Trp Glu Lys Gly Val Val Ser His
145                 150                 155                 160

Gln Trp Val Thr Asp Phe Val Trp Gly Asp His Thr Asp Pro Tyr Gly
                165                 170                 175

Tyr Leu Ala Lys Met Gly Ile Ser Lys Ala Gln Leu Ala His Asp Leu
            180                 185                 190

Ala Asn Gly Val Ser Gly Asn Thr Ala Thr Pro Thr Pro Lys Pro Asp
        195                 200                 205

Lys Pro Lys Pro Thr Gln Pro Ser Lys Pro Ser Asn Lys Lys Arg Phe
    210                 215                 220

Asn Tyr Arg Val Asp Gly Leu Glu Tyr Val Asn Gly Met Trp Gln Ile
225                 230                 235                 240

Tyr Asn Glu His Leu Gly Lys Ile Asp Phe Asn Trp Thr Glu Asn Gly
                245                 250                 255

Ile Pro Val Glu Val Val Asp Lys Val Asn Pro Ala Thr Gly Gln Pro
            260                 265                 270

Thr Lys Asp Gln Val Leu Lys Val Gly Asp Tyr Phe Asn Phe Gln Glu
        275                 280                 285

Asn Ser Thr Gly Val Val Gln Glu Gln Thr Pro Tyr Met Gly Tyr Thr
    290                 295                 300

Leu Ser His Val Gln Leu Pro Asn Glu Phe Ile Trp Leu Phe Thr Asp
305                 310                 315                 320

Ser Lys Gln Ala Leu Met Tyr Gln
                325

<210> SEQ ID NO 30
<211> LENGTH: 289
<212> TYPE: PRT
<213> ORGANISM: Enterobacteria phage jEF24C

<400> SEQUENCE: 30

Met Ala Gly Glu Val Phe Ser Ser Leu Ile Thr Ser Val Asn Pro Asn
1               5                   10                  15

Pro Met Asn Ala Gly Ser Arg Asn Gly Ile Pro Ile Asp Thr Ile Ile
                20                  25                  30

Leu His His Asn Ala Thr Thr Asn Lys Asp Val Ala Met Asn Thr Trp
            35                  40                  45

Leu Leu Gly Gly Gly Ala Gly Thr Ser Ala His Tyr Glu Cys Thr Pro
        50                  55                  60

Thr Glu Ile Ile Gly Cys Val Gly Glu Gln Tyr Ser Ala Phe His Ala
65                  70                  75                  80

Gly Gly Thr Gly Gly Ile Asp Val Pro Lys Ile Ala Asn Pro Asn Gln
                85                  90                  95

Arg Ser Ile Gly Ile Glu Asn Val Asn Ser Ser Gly Ala Pro Asn Trp
            100                 105                 110

Ser Val Asp Pro Arg Thr Ile Thr Asn Cys Ala Arg Leu Val Ala Asp
        115                 120                 125

Ile Cys Thr Arg Tyr Gly Ile Pro Cys Asp Arg Gln His Val Leu Gly
    130                 135                 140
```

```
His Asn Glu Val Thr Ala Thr Ala Cys Pro Gly Gly Met Asp Val Asp
145                 150                 155                 160

Glu Val Val Arg Gln Ala Gln Gln Phe Met Ala Gly Gly Ser Asn Asn
                165                 170                 175

Ala Val Lys Pro Glu Pro Ser Lys Pro Thr Pro Ser Lys Pro Ser Asn
            180                 185                 190

Asn Lys Asn Lys Glu Gly Val Ala Thr Met Tyr Cys Leu Tyr Glu Arg
        195                 200                 205

Pro Ile Asn Ser Lys Thr Gly Val Leu Glu Trp Asn Gly Asp Ala Trp
    210                 215                 220

Thr Val Met Phe Cys Asn Gly Val Asn Cys Arg Arg Val Ser His Pro
225                 230                 235                 240

Asp Glu Met Lys Val Ile Glu Asp Ile Tyr Arg Lys Asn Asn Gly Lys
                245                 250                 255

Asp Ile Pro Phe Tyr Ser Gln Lys Glu Trp Asn Lys Asn Ala Pro Trp
            260                 265                 270

Tyr Asn Arg Leu Glu Thr Val Cys Pro Val Val Gly Ile Thr Lys Lys
        275                 280                 285

Ser

<210> SEQ ID NO 31
<211> LENGTH: 237
<212> TYPE: PRT
<213> ORGANISM: Enterobacteria phage F168/08

<400> SEQUENCE: 31

Met Val Lys Leu Asn Asp Val Leu Ser Tyr Val Asn Gly Leu Val Gly
1               5                   10                  15

Lys Gly Val Asp Ala Asp Gly Trp Tyr Gly Thr Gln Cys Met Asp Leu
            20                  25                  30

Thr Val Asp Val Met Gln Arg Phe Phe Gly Trp Arg Pro Tyr Gly Asn
        35                  40                  45

Ala Ile Ala Leu Val Asp Gln Pro Ile Pro Ala Gly Phe Gln Arg Ile
    50                  55                  60

Arg Thr Thr Ser Ser Thr Gln Ile Lys Ala Gly Asp Val Met Ile Trp
65                  70                  75                  80

Gly Leu Gly Tyr Tyr Ala Gln Tyr Gly His Thr His Ile Ala Thr Glu
                85                  90                  95

Asp Gly Arg Ala Asp Gly Thr Phe Val Ser Val Asp Gln Asn Trp Ile
            100                 105                 110

Asn Pro Ser Leu Glu Val Gly Ser Pro Ala Ala Ala Ile His His Asn
        115                 120                 125

Met Asp Gly Val Trp Gly Val Ile Arg Pro Pro Tyr Glu Ala Glu Ser
    130                 135                 140

Lys Pro Lys Pro Pro Ala Pro Lys Pro Asp Lys Pro Asn Leu Gly Gln
145                 150                 155                 160

Phe Lys Gly Asp Asp Asp Ile Met Phe Ile Tyr Lys Lys Thr Lys
                165                 170                 175

Gln Gly Ser Thr Glu Gln Trp Phe Val Ile Gly Gly Lys Arg Ile Tyr
            180                 185                 190

Leu Pro Thr Met Thr Tyr Val Asn Glu Ala Asn Asp Leu Ile Lys Arg
        195                 200                 205

Tyr Gly Gly Asn Thr Asn Val Thr Thr Tyr Asn Tyr Asp Asn Phe Gly
    210                 215                 220
```

Leu Ala Met Met Glu Lys Ala Tyr Pro Gln Val Lys Leu
225                 230                 235

<210> SEQ ID NO 32
<211> LENGTH: 7
<212> TYPE: PRT
<213> ORGANISM: artificial
<220> FEATURE:
<223> OTHER INFORMATION: peptide sequence of a modulating agent
      (pheromone peptide) of a pheromone-responsive promoter

<400> SEQUENCE: 32

Leu Val Thr Leu Val Phe Val
1               5

<210> SEQ ID NO 33
<211> LENGTH: 9
<212> TYPE: PRT
<213> ORGANISM: artificial
<220> FEATURE:
<223> OTHER INFORMATION: peptide sequence of a modulating agent
      (pheromone peptide) of a pheromone-responsive promoter

<400> SEQUENCE: 33

Ala Leu Phe Ser Leu Val Leu Ala Gly
1               5

<210> SEQ ID NO 34
<211> LENGTH: 8
<212> TYPE: PRT
<213> ORGANISM: artificial
<220> FEATURE:
<223> OTHER INFORMATION: peptide sequence of a modulating agent
      (pheromone peptide) of a pheromone-responsive promoter

<400> SEQUENCE: 34

Phe Leu Val Met Phe Leu Ser Gly
1               5

<210> SEQ ID NO 35
<211> LENGTH: 7
<212> TYPE: PRT
<213> ORGANISM: artificial
<220> FEATURE:
<223> OTHER INFORMATION: peptide sequence of a modulating agent
      (pheromone peptide) of a pheromone-responsive promoter

<400> SEQUENCE: 35

Ala Ile Phe Ile Leu Ala Ser
1               5

<210> SEQ ID NO 36
<211> LENGTH: 19
<212> TYPE: PRT
<213> ORGANISM: artificial
<220> FEATURE:
<223> OTHER INFORMATION: synthetic A3APO peptide

<400> SEQUENCE: 36

Arg Pro Asp Lys Pro Arg Pro Tyr Leu Pro Arg Pro Arg Pro Pro Arg
1               5                   10                  15

Pro Val Arg

<210> SEQ ID NO 37
<211> LENGTH: 23
<212> TYPE: PRT
<213> ORGANISM: artificial

```
<220> FEATURE:
<223> OTHER INFORMATION: synthetic alyteserin-1a peptide

<400> SEQUENCE: 37

Gly Leu Lys Asp Ile Phe Lys Ala Gly Leu Gly Ser Leu Val Lys Gly
1               5                   10                  15

Ile Ala Ala His Val Ala Asn
            20

<210> SEQ ID NO 38
<211> LENGTH: 142
<212> TYPE: DNA
<213> ORGANISM: artificial
<220> FEATURE:
<223> OTHER INFORMATION: synthetic A3APO gene

<400> SEQUENCE: 38
atggatgaaa aaaagatta tctcagctat tttaatgtct acagtgatac tttctgctgc       60
agccccgttg tcaggtgttt acgctcgtcc agataaacca cgtccatatt taccacgtcc      120
acgtccacca cgtccagttc gt                                               142

<210> SEQ ID NO 39
<211> LENGTH: 150
<212> TYPE: DNA
<213> ORGANISM: artificial
<220> FEATURE:
<223> OTHER INFORMATION: synthetic alyteserin-1a gene

<400> SEQUENCE: 39
atgaaaaaaa agattatctc agctatttta atgtctacag tgatactttc tgctgcagcc      60
ccgttgtcag gtgtttacgc tggtttaaaa gatattttta agctggttta aggttcatta     120
gttaaaggta ttgctgctca tgttgctaat                                      150

<210> SEQ ID NO 40
<211> LENGTH: 25
<212> TYPE: DNA
<213> ORGANISM: artificial
<220> FEATURE:
<223> OTHER INFORMATION: synthetic oligonucleotide primer

<400> SEQUENCE: 40
cgttgtcagg tgtttacgct ggttt                                            25

<210> SEQ ID NO 41
<211> LENGTH: 26
<212> TYPE: DNA
<213> ORGANISM: artificial
<220> FEATURE:
<223> OTHER INFORMATION: synthetic oligonucleotide primer

<400> SEQUENCE: 41
cgtttaatta gcaacatgag cagcaa                                           26

<210> SEQ ID NO 42
<211> LENGTH: 31
<212> TYPE: DNA
<213> ORGANISM: artificial
<220> FEATURE:
<223> OTHER INFORMATION: synthetic oligonucleotide primer

<400> SEQUENCE: 42
ttttaatgtc tacagtgata ctttctgctg c                                     31
```

```
<210> SEQ ID NO 43
<211> LENGTH: 26
<212> TYPE: DNA
<213> ORGANISM: artificial
<220> FEATURE:
<223> OTHER INFORMATION: synthetic oligonucleotide primer

<400> SEQUENCE: 43
atacgtttaa cgaactggac gtggtg                                    26

<210> SEQ ID NO 44
<211> LENGTH: 20
<212> TYPE: DNA
<213> ORGANISM: artificial
<220> FEATURE:
<223> OTHER INFORMATION: synthetic oligonucleotide primer

<400> SEQUENCE: 44
gcgttctgga gttgggatgt                                           20

<210> SEQ ID NO 45
<211> LENGTH: 20
<212> TYPE: DNA
<213> ORGANISM: artificial
<220> FEATURE:
<223> OTHER INFORMATION: synthetic oligonucleotide primer

<400> SEQUENCE: 45
cctcttgagc gaatacgatt                                           20

<210> SEQ ID NO 46
<211> LENGTH: 30
<212> TYPE: DNA
<213> ORGANISM: artificial
<220> FEATURE:
<223> OTHER INFORMATION: synthetic oligonucleotide primer

<400> SEQUENCE: 46
actcatcatg aaaaaaaaga ttatctcagc                                30

<210> SEQ ID NO 47
<211> LENGTH: 53
<212> TYPE: DNA
<213> ORGANISM: artificial
<220> FEATURE:
<223> OTHER INFORMATION: synthetic oligonucleotide primer

<400> SEQUENCE: 47
gatctagatt agtgatggtg atggtgatga ccaccacgaa ctggacgtgg tgg       53

<210> SEQ ID NO 48
<211> LENGTH: 53
<212> TYPE: DNA
<213> ORGANISM: artificial
<220> FEATURE:
<223> OTHER INFORMATION: synthetic oligonucleotide primer

<400> SEQUENCE: 48
gatctagatt agtgatggtg atggtgatga ccaccattag caacatgagc agc       53

<210> SEQ ID NO 49
<211> LENGTH: 7
<212> TYPE: PRT
<213> ORGANISM: artificial
<220> FEATURE:
<223> OTHER INFORMATION: fragment of iCF10 peptide
```

<400> SEQUENCE: 49

Ala Ile Thr Leu Ile Phe Ile
1               5

<210> SEQ ID NO 50
<211> LENGTH: 8
<212> TYPE: PRT
<213> ORGANISM: artificial
<220> FEATURE:
<223> OTHER INFORMATION: fragment of Ipd peptide

<400> SEQUENCE: 50

Ala Leu Ile Leu Thr Leu Val Ser
1               5

<210> SEQ ID NO 51
<211> LENGTH: 8
<212> TYPE: PRT
<213> ORGANISM: artificial
<220> FEATURE:
<223> OTHER INFORMATION: fragment of Iad peptide

<400> SEQUENCE: 51

Leu Phe Val Val Thr Leu Cys Gly
1               5

<210> SEQ ID NO 52
<211> LENGTH: 7
<212> TYPE: PRT
<213> ORGANISM: artificial
<220> FEATURE:
<223> OTHER INFORMATION: fragment of Ipd peptide

<400> SEQUENCE: 52

Ser Ile Phe Thr Leu Val Ala
1               5

<210> SEQ ID NO 53
<211> LENGTH: 321
<212> TYPE: PRT
<213> ORGANISM: artificial
<220> FEATURE:
<223> OTHER INFORMATION: TraA peptide enclded by pPD1

<400> SEQUENCE: 53

Met His Leu Asn Glu Leu Met Lys Ile Gln Arg Lys Ser Glu Lys Leu
1               5                   10                  15

Ser Gln Ala Lys Phe Tyr Glu Gly Ile Phe Gln Arg Asn Ser Ala Ser
                20                  25                  30

Leu Phe Glu Asn His Asn Glu His Phe Leu Lys Ile Ala Asp Leu Pro
            35                  40                  45

Ile Leu Ala Asp Arg Ser Asn Leu Thr Ile Pro Glu Ile Ile Arg Thr
        50                  55                  60

Cys Asn Glu Asp Phe Lys Ser Val Phe Asp Lys Leu Glu Thr Tyr
65                  70                  75                  80

Tyr Phe Val Leu Ser Lys Ile Gln Gln Asn Pro Asp Ser Glu Tyr Asn
                85                  90                  95

Gln Glu Leu Tyr Ser Leu Tyr Gln Lys Ser Ile His Glu Lys Phe Thr
            100                 105                 110

Ser Leu Lys Tyr Met Asn Leu Tyr Leu Leu Ile Lys Leu Gln Thr Ser
        115                 120                 125

```
Ser Leu Ile Ser Glu Ile Ile Pro Val Asp Lys Gln Asp Leu Ala Asp
    130                 135                 140

Ile Lys Lys Met Phe Ser Ser Lys Arg Phe Val Leu Tyr His Tyr
145                 150                 155                 160

Lys Ile Leu Ser Asn Leu Cys Thr Ile Phe Pro Tyr Ser Asp Leu Gln
                165                 170                 175

Thr Leu Ile Glu Gln Leu Phe Pro Leu Arg Glu Asp Ser Asp Glu Gln
            180                 185                 190

Ile Lys Asp Thr Ala Cys Leu Ser Leu Ser Asn Ala Ile Ala Leu Ser
        195                 200                 205

Ile Phe Thr Lys Asp Tyr Ser Ser Cys Phe Ile Leu Leu Asn His Phe
    210                 215                 220

Glu Thr Leu Leu Ser Asn Tyr Thr Ser Tyr Lys Tyr Lys Leu Ser Phe
225                 230                 235                 240

Ile Ala Ser Arg Asn Met Leu Leu Tyr Phe Thr Ser Gly Asp Ile Glu
                245                 250                 255

His Ile Met Lys Val Phe Ser Tyr Val Glu Ile Leu Lys Gln Val Glu
            260                 265                 270

Ser Pro Glu Tyr Val Glu Gln Phe His Lys Asn Leu Gln Thr Ile Ile
        275                 280                 285

Ser Lys Ser Asp Asp Glu Lys Ala Lys Gln Ile Phe Gly Val Leu Asp
    290                 295                 300

Asp Asp Gly Gln Val Leu Asp Pro Lys Asn Phe Asp His Lys Lys Ile
305                 310                 315                 320

Asp

<210> SEQ ID NO 54
<211> LENGTH: 319
<212> TYPE: PRT
<213> ORGANISM: artificial
<220> FEATURE:
<223> OTHER INFORMATION: TraA peptide analog encloded by pAD1

<400> SEQUENCE: 54

Met Phe Leu Tyr Glu Leu Phe Lys Glu Gln Arg Lys Leu Tyr Asn Phe
1               5                   10                  15

Thr Gln Glu Glu Phe Tyr Glu Gly Ile Phe Lys Lys Arg Ala Ala Ser
            20                  25                  30

Ser Phe Glu Val His Asn Thr His Asp Leu Lys Val Lys Asp Leu Pro
        35                  40                  45

Val Leu Ser Asp Arg Ser Met Met Ser Ile Leu Glu Ile Ile His Tyr
50                  55                  60

Ala Lys Glu Glu Phe Ile Ser Pro Tyr Asp Glu Asp Leu Asn Ser Leu
65                  70                  75                  80

Phe Asp Ile Phe Gln Asn Asn Thr Glu Lys Glu Asn Lys Asp Tyr Ile
                85                  90                  95

Tyr Lys Leu Tyr Lys Lys Ser Ile Glu Leu Lys Glu His Ser Ile Ile
            100                 105                 110

Tyr Trp Asn Leu Tyr Leu Ile Ile Lys Ile Gln Cys Ser Glu Tyr Asp
        115                 120                 125

Ser Arg Ile Val Pro Thr Asp Ser Gln Asp Leu Ser Glu Leu Lys Lys
    130                 135                 140

Met Ile Leu Ser Lys Gln Lys Phe Thr Leu Tyr Asp Tyr Lys Ile Val
145                 150                 155                 160

Thr Asn Leu Ser Leu Val Phe Ser Tyr Lys Glu Leu Gln Pro Phe Leu
```

```
                165                 170                 175
Ser Ser Leu Phe Pro Leu Asp Ser Asn Ala Pro Thr Val Thr Ser Glu
            180                 185                 190

Ala Ala Tyr Tyr Leu Leu Glu Asn Ile Thr Thr Lys Leu Val Gln Asn
        195                 200                 205

Arg Asp Phe Glu Ser Cys Thr Glu Val Leu Asn Ile Tyr Asn Asp Leu
    210                 215                 220

Leu Gln Lys Phe Pro Ser Tyr Lys Tyr Lys Leu Asn Tyr Leu Ile Thr
225                 230                 235                 240

Tyr Asn Leu Val Gly Tyr Phe Leu Thr Asn Asn Met Asp Ser Leu Asn
                245                 250                 255

Asn Ser Ile Lys Tyr Val Asp Leu Leu Gly Asp Leu Glu Asn Val Glu
            260                 265                 270

Leu Ala Lys Leu Met Lys Asp Asn Ile Tyr Leu Met Ile Ser Lys Lys
        275                 280                 285

Asn Asn Gly Ser Met Ser Lys Pro Asp Thr Leu Leu Thr Lys Glu Asn
    290                 295                 300

Asn His Ile Lys Leu Asn Glu Lys Lys Ile Thr Lys Arg Leu Glu
305                 310                 315

<210> SEQ ID NO 55
<211> LENGTH: 337
<212> TYPE: PRT
<213> ORGANISM: artificial
<220> FEATURE:
<223> OTHER INFORMATION: TraA peptide analog enclded by pAM373

<400> SEQUENCE: 55

Met Asn Ile Gly Gly Phe Phe Met Phe Ile Asn Asp Phe Leu Lys His
1               5                   10                  15

Thr Arg Asn Asn Leu Asn Leu Ser Gln Thr Thr Phe Tyr Lys Asp Val
            20                  25                  30

Leu Ser Arg Ser Thr Ala Asp Lys Phe Glu Lys Asn Lys Thr Ser Ile
        35                  40                  45

Lys Leu Ser Cys Ile Pro Ile Leu Ala Asp Arg Leu Asp Leu Thr Cys
    50                  55                  60

Glu Glu Ile Leu Phe Tyr Ser Ser Asp Thr Leu His Thr Asp Phe Asp
65                  70                  75                  80

Lys Leu Arg Asp Ser Phe Leu Asn Lys Tyr Ala Ser Leu Gln Ser Leu
                85                  90                  95

Glu Glu Lys Ser Glu Ile Asn Glu Val Thr Lys Asp Ile Thr Ala Ile
            100                 105                 110

Tyr Met Gln Cys Ile Glu Pro Lys Tyr Tyr Ser Leu Lys Tyr Phe Asn
        115                 120                 125

Leu Tyr Leu Leu Ile Lys Ile Ser Cys Ser Glu Phe Thr Asp Lys Ile
130                 135                 140

Leu Glu Val Asp Lys Ala Asp Leu Met Asp Leu Lys Lys Ile Tyr Arg
145                 150                 155                 160

Thr Arg Lys Leu Tyr Thr Ser Ser Asp Tyr Lys Val Leu Ala Asn Leu
                165                 170                 175

Ile Thr Leu Pro Leu Phe Thr Val Asn Asp Leu Asn Phe Met Phe Asp
            180                 185                 190

Val Leu Tyr Pro Leu Ala Asn Asn Val Pro Glu Glu Ile Leu Tyr Pro
        195                 200                 205

Ala Tyr Leu Ala Leu Thr Asn Leu Thr Thr Lys His Ile Lys Asn Lys
```

```
           210                 215                 220
Asp Tyr Asn Lys Ala Lys Leu Ala Ile Asn Asn Phe Glu Glu Gln Leu
225                 230                 235                 240

Lys Val Asn Pro Ser Tyr Lys Phe Lys Leu Ile Cys Leu His Asp Arg
                245                 250                 255

Ala Leu Leu Asp Phe Leu Thr Asp Lys Ile Asn Asn Ser Ser Lys Leu
                260                 265                 270

Thr Glu Ala Leu Gln Ile Ile Asn Ile Ile Asp Ser Cys Glu Pro Pro
            275                 280                 285

Ser Ser Ser Leu Ala Asp Arg Met Lys Glu Ala Thr Val Ser Ile Ile
            290                 295                 300

Glu Lys Glu Asp Asn Thr Lys Asp Ile Ile Ala Ile Ala Asn Thr
305                 310                 315                 320

Lys Ser Ser Ile Asp Tyr Met Gln Thr Ile Pro Pro Asn Ile Val Lys
                325                 330                 335

Thr

<210> SEQ ID NO 56
<211> LENGTH: 21
<212> TYPE: PRT
<213> ORGANISM: artificial
<220> FEATURE:
<223> OTHER INFORMATION: Ipd peptide enclded by pPD1

<400> SEQUENCE: 56

Met Lys Gln Gln Lys Lys His Ile Ala Ala Leu Leu Phe Ala Leu Ile
1               5                   10                  15

Leu Thr Leu Val Ser
            20

<210> SEQ ID NO 57
<211> LENGTH: 22
<212> TYPE: PRT
<213> ORGANISM: artificial
<220> FEATURE:
<223> OTHER INFORMATION: Iad peptide enclded by pAD1

<400> SEQUENCE: 57

Met Ser Lys Arg Ala Met Lys Lys Ile Ile Pro Leu Ile Thr Leu Phe
1               5                   10                  15

Val Val Thr Leu Val Gly
            20

<210> SEQ ID NO 58
<211> LENGTH: 24
<212> TYPE: PRT
<213> ORGANISM: artificial
<220> FEATURE:
<223> OTHER INFORMATION: i373 peptide enclded by pAM373

<400> SEQUENCE: 58

Met Lys Lys Glu Leu Ile Leu Ile Leu Lys Trp Leu Thr Pro Ile Gly
1               5                   10                  15

Leu Ser Ile Phe Thr Leu Val Ala
            20

<210> SEQ ID NO 59
<211> LENGTH: 2619
<212> TYPE: DNA
<213> ORGANISM: artificial
<220> FEATURE:
```

<223> OTHER INFORMATION: nucleotide sequence of the Bac fragment

<400> SEQUENCE: 59

```
gggatccaaa aggaggagaa aactactatg aaaaaaaaga ttatctcagc tattttaatg      60
tctacagtga tactttctgc tgcagccccg ttgtcaggtg tttacgctac cactcatagt     120
ggaaaatatt atggaaatgg agtgtattgc actaaaaata aatgtacggt cgattgggcc     180
aaggcaacta cttgtattgc aggaatgtct ataggtggtt ttttaggtgg agcaattcca     240
gggaagtgct aaaatgaaaa aaaatgctaa gcaaattgtt catgaattat ataatgatat     300
atctataagt aaagatccta aatattctga tattcttgag gttttacaaa aggtatattt     360
aaaattagaa aaacaaaaat atgaattaga tcccggtcct ttaataaata gattggtgaa     420
ttatctatat tttactgctt atactaataa aataagattc actgaatatc aagaggaatt     480
aataagaaat ttgagtgaaa ttggaagaac tgctggaata aatggtttat atcgagcaga     540
ttatggagat aaatctcaat tttaataaag gaggaataat aatgaaaaag aaagtattaa     600
aacattgtgt tattctagga atattaggaa cttgtctagc tggcatcggt acaggaataa     660
aagttgatgc agctacttac tatggaaatg gtctttattg taacaaagaa aaatgttggg     720
tagattggaa tcaagctaaa ggagaaattg gaaaaattat tgttaatggt tgggttaatc     780
atggtccatg ggcacctaga aggtagtggt agggaggtta ttataatgga ttttactaaa     840
gaagaaaaac ttttaaatgc aattagtaaa gtatacaatg aagcaactat agatgactat     900
cctgacttaa agaaaagct ctttctttat tctaaagaaa tcagtgaggg aaaaagtgtt     960
ggtgaagtta gtatgaaatt aagtagtttt cttggaagat atatttttaaa acataaatttt    1020
ggattaccta aatctttaat agaattacaa gaaattgtta gtaaggaatc tcaagtatat    1080
agaggatggg cttctattgg tatttggagt taaaaggag gtattgattt atgagaaaaa    1140
aattatttag tttagctctt attggaatat ttgggttagt tgtgacaaat tttggtacaa    1200
aagttgatgc agctacgcgt tcatatggta atggtgttta ttgtaataat agtaaatgct    1260
gggttaactg gggagaagct aaagagaata ttgcaggaat cgttattagt ggctgggctt    1320
ctggtttggc aggtatggga cattaatact atgaaaagta ataaatcttt caacaaagtt    1380
ctagaattaa ctgaaacagc attagccacc ccagaaatta aaaaagataa aaatctatgt    1440
gaaattttag aaaaagtaaa agctagtgct gctaaaggtg aattttatta tgattacaag    1500
aaagaatttc aacctgcaat tagtggattc actattagaa acggcttttc cacaccgaag    1560
gttttattgg agttgcttgc tgaagtaaaa actcccaaag catggtcggg actttgataa    1620
gaattcggga tccaaaagga ggagaaaact actatgaaaa aaaagattat ctcagctatt    1680
ttaatgtcta cagtgatact ttctgctgca gccccgttgt caggtgttta cgctaagacg    1740
tctgcaggag aagtatttag tagcttgatt acaagtgtaa atcctaaccc aatgaacgca    1800
ggtagtcgta atggtatccc tatcgacacc attatcctac atcacaatgc aacaacaaat    1860
aaagatgttg ctatgaacac atggctatta ggtggtggcg caggtacatc tgctcattat    1920
gaatgtacac caacagaaat tattggatgt gtcggtgagc agtattcagc attccatgcc    1980
ggaggtacag gtggtataga tgttcctaag attgctaacc ctaaccaacg ttcaataggt    2040
attgaaaatg taaactcgtc aggagcacct aattggtctg tagaccctag aacaattaca    2100
aattgtgctc gtttagtggc agatatttgt acacgttatg gtattccatg tgaccgacaa    2160
cacgtgttag acataacgga agtaactgca acagcgtgcc ccggaggtat ggacgtagac    2220
gaagttgtac gtcaagctca acagttcatg gcaggaggct ctaacaatgc agttaagccg    2280
```

```
gagccaagta agcctacacc aagcaaacca agtaataata aaaataaaga aggagtggca    2340
actatgtatt gtttatacga aagacctatt aactcaaaaa caggagtact agagtggaat    2400
ggtgatgcat ggacagttat gttctgtaat ggggtaaact gtcgcagagt atctcatcca    2460
gatgaaatga agtaattga ggatatttac agaaaaaata acggaaaaga cattccattt    2520
tacagtcaaa aagaatggaa taaaaatgca ccatggtata acagattaga gacagtatgt    2580
ccagtagtag gtattactaa aaaatcttaa taagaattc                          2619
```

<210> SEQ ID NO 60
<211> LENGTH: 74
<212> TYPE: PRT
<213> ORGANISM: artificial
<220> FEATURE:
<223> OTHER INFORMATION: peptide encoded by structural gene entA

<400> SEQUENCE: 60

```
Met Lys Lys Lys Ile Ile Ser Ala Ile Leu Met Ser Thr Val Ile Leu
1               5                   10                  15

Ser Ala Ala Ala Pro Leu Ser Gly Val Tyr Ala Thr Thr His Ser Gly
            20                  25                  30

Lys Tyr Tyr Gly Asn Gly Val Tyr Cys Thr Lys Asn Lys Cys Thr Val
        35                  40                  45

Asp Trp Ala Lys Ala Thr Thr Cys Ile Ala Gly Met Ser Ile Gly Gly
    50                  55                  60

Phe Leu Gly Gly Ala Ile Pro Gly Lys Cys
65                  70
```

<210> SEQ ID NO 61
<211> LENGTH: 103
<212> TYPE: PRT
<213> ORGANISM: artificial
<220> FEATURE:
<223> OTHER INFORMATION: peptide encoded by immunity coding region entiA

<400> SEQUENCE: 61

```
Met Lys Lys Asn Ala Lys Gln Ile Val His Glu Leu Tyr Asn Asp Ile
1               5                   10                  15

Ser Ile Ser Lys Asp Pro Lys Tyr Ser Asp Ile Leu Glu Val Leu Gln
            20                  25                  30

Lys Val Tyr Leu Lys Leu Glu Lys Gln Lys Tyr Glu Leu Asp Pro Gly
        35                  40                  45

Pro Leu Ile Asn Arg Leu Val Asn Tyr Leu Tyr Phe Thr Ala Tyr Thr
    50                  55                  60

Asn Lys Ile Arg Phe Thr Glu Tyr Gln Glu Glu Leu Ile Arg Asn Leu
65                  70                  75                  80

Ser Glu Ile Gly Arg Thr Ala Gly Ile Asn Gly Leu Tyr Arg Ala Asp
                85                  90                  95

Tyr Gly Asp Lys Ser Gln Phe
            100
```

<210> SEQ ID NO 62
<211> LENGTH: 74
<212> TYPE: PRT
<213> ORGANISM: artificial
<220> FEATURE:
<223> OTHER INFORMATION: peptide encoded by structural gene hirJM79

<400> SEQUENCE: 62

Met Lys Lys Val Leu Lys His Cys Val Ile Gly Ile Leu Gly
1               5                  10                 15

Thr Cys Leu Ala Gly Ile Gly Thr Gly Ile Lys Val Asp Ala Ala Thr
                20                  25                  30

Tyr Tyr Gly Asn Gly Leu Tyr Cys Asn Lys Glu Lys Cys Trp Val Asp
                35                  40                  45

Trp Asn Gln Ala Lys Gly Glu Ile Gly Lys Ile Ile Val Asn Gly Trp
            50                  55                  60

Val Asn His Gly Pro Trp Ala Pro Arg Arg
65                  70

<210> SEQ ID NO 63
<211> LENGTH: 95
<212> TYPE: PRT
<213> ORGANISM: artificial
<220> FEATURE:
<223> OTHER INFORMATION: peptide encoded by immunity coding region
      hiriJM79

<400> SEQUENCE: 63

Met Asp Phe Thr Lys Glu Glu Lys Leu Leu Asn Ala Ile Ser Lys Val
1               5                  10                  15

Tyr Asn Glu Ala Thr Ile Asp Asp Tyr Pro Asp Leu Lys Glu Lys Leu
                20                  25                  30

Phe Leu Tyr Ser Lys Glu Ile Ser Glu Gly Lys Ser Val Gly Glu Val
                35                  40                  45

Ser Met Lys Leu Ser Ser Phe Leu Gly Arg Tyr Ile Leu Lys His Lys
            50                  55                  60

Phe Gly Leu Pro Lys Ser Leu Ile Glu Leu Gln Glu Ile Val Ser Lys
65                  70                  75                  80

Glu Ser Gln Val Tyr Arg Gly Trp Ala Ser Ile Gly Ile Trp Ser
                85                  90                  95

<210> SEQ ID NO 64
<211> LENGTH: 71
<212> TYPE: PRT
<213> ORGANISM: artificial
<220> FEATURE:
<223> OTHER INFORMATION: peptide encoded by structural gene entP

<400> SEQUENCE: 64

Met Arg Lys Lys Leu Phe Ser Leu Ala Leu Ile Gly Ile Phe Gly Leu
1               5                  10                  15

Val Val Thr Asn Phe Gly Thr Lys Val Asp Ala Ala Thr Arg Ser Tyr
                20                  25                  30

Gly Asn Gly Val Tyr Cys Asn Asn Ser Lys Cys Trp Val Asn Trp Gly
                35                  40                  45

Glu Ala Lys Glu Asn Ile Ala Gly Ile Val Ile Ser Gly Trp Ala Ser
            50                  55                  60

Gly Leu Ala Gly Met Gly His
65                  70

<210> SEQ ID NO 65
<211> LENGTH: 88
<212> TYPE: PRT
<213> ORGANISM: artificial
<220> FEATURE:
<223> OTHER INFORMATION: peptide encoded by immunity coding region entiP

<400> SEQUENCE: 65

```
Met Lys Ser Asn Lys Ser Phe Asn Lys Val Leu Glu Leu Thr Glu Thr
1               5                   10                  15

Ala Leu Ala Thr Pro Glu Ile Lys Lys Asp Lys Asn Leu Cys Glu Ile
            20                  25                  30

Leu Glu Lys Val Lys Ala Ser Ala Ala Lys Gly Glu Phe Tyr Tyr Asp
            35                  40                  45

Tyr Lys Lys Glu Phe Gln Pro Ala Ile Ser Gly Phe Thr Ile Arg Asn
50                  55                  60

Gly Phe Ser Thr Pro Lys Val Leu Leu Glu Leu Ala Glu Val Lys
65                  70                  75                  80

Thr Pro Lys Ala Trp Ser Gly Leu
                85
```

<210> SEQ ID NO 66
<211> LENGTH: 318
<212> TYPE: PRT
<213> ORGANISM: artificial
<220> FEATURE:
<223> OTHER INFORMATION: peptide encoded by structural gene Lys170

<400> SEQUENCE: 66

```
Met Lys Lys Lys Ile Ile Ser Ala Ile Leu Met Ser Thr Val Ile Leu
1               5                   10                  15

Ser Ala Ala Pro Leu Ser Gly Val Tyr Ala Lys Thr Ser Ala Gly
            20                  25                  30

Glu Val Phe Ser Ser Leu Ile Thr Ser Val Asn Pro Asn Pro Met Asn
            35                  40                  45

Ala Gly Ser Arg Asn Gly Ile Pro Ile Asp Thr Ile Ile Leu His His
50                  55                  60

Asn Ala Thr Thr Asn Lys Asp Val Ala Met Asn Thr Trp Leu Leu Gly
65                  70                  75                  80

Gly Gly Ala Gly Thr Ser Ala His Tyr Glu Cys Thr Pro Thr Glu Ile
            85                  90                  95

Ile Gly Cys Val Gly Glu Gln Tyr Ser Ala Phe His Ala Gly Gly Thr
            100                 105                 110

Gly Gly Ile Asp Val Pro Lys Ile Ala Asn Pro Asn Gln Arg Ser Ile
            115                 120                 125

Gly Ile Glu Asn Val Asn Ser Ser Gly Ala Pro Asn Trp Ser Val Asp
130                 135                 140

Pro Arg Thr Ile Thr Asn Cys Ala Arg Leu Val Ala Asp Ile Cys Thr
145                 150                 155                 160

Arg Tyr Gly Ile Pro Cys Asp Arg Gln His Val Leu Gly His Asn Glu
                165                 170                 175

Val Thr Ala Thr Ala Cys Pro Gly Gly Met Asp Val Asp Glu Val Val
            180                 185                 190

Arg Gln Ala Gln Gln Phe Met Ala Gly Gly Ser Asn Asn Ala Val Lys
            195                 200                 205

Pro Glu Pro Ser Lys Pro Thr Pro Ser Lys Pro Ser Asn Asn Lys Asn
            210                 215                 220

Lys Glu Gly Val Ala Thr Met Tyr Cys Leu Tyr Glu Arg Pro Ile Asn
225                 230                 235                 240

Ser Lys Thr Gly Val Leu Glu Trp Asn Gly Asp Ala Trp Thr Val Met
            245                 250                 255

Phe Cys Asn Gly Val Asn Cys Arg Arg Val Ser His Pro Asp Glu Met
            260                 265                 270
```

-continued

```
Lys Val Ile Glu Asp Ile Tyr Arg Lys Asn Asn Gly Lys Asp Ile Pro
        275                 280                 285

Phe Tyr Ser Gln Lys Glu Trp Asn Lys Asn Ala Pro Trp Tyr Asn Arg
        290                 295                 300

Leu Glu Thr Val Cys Pro Val Val Gly Ile Thr Lys Lys Ser
305                 310                 315
```

METHODS FOR MAKING AND USING ANTIMICROBIAL PEPTIDES

CROSS-REFERENCE TO RELATED APPLICATIONS

This application is a divisional application of U.S. patent application Ser. No. 15/894,408, filed Feb. 12, 2018, which is a divisional application of U.S. patent application Ser. No. 14/431,044, filed Mar. 25, 2015, which is a U.S. National Stage application of International Application No. PCT/US2013/061659, filed on Sep. 25, 2013, which claims the benefit of U.S. Provisional Application No. 61/705,489, filed Sep. 25, 2012, each of which is incorporated by reference herein.

GOVERNMENT FUNDING

This present invention was made with government support under GM086865 awarded by National Institutes of Health, and CBET-0425882 and CBET-0644792 awarded by National Science Foundation. The government has certain rights in the invention.

SEQUENCE LISTING

This application contains a Sequence Listing electronically submitted via EFS-Web to the United States Patent and Trademark Office as an ASCII text file entitled "110-03560101_SequenceListing_ST25.txt" having a size of 81 kilobytes and created on May 12, 2015. The information contained in the Sequence Listing is incorporated by reference herein.

BACKGROUND

There is growing concern worldwide that extensive use of antibiotics is resulting in the development of antibiotic resistance among pathogenic bacteria. In particular, antibiotic overuse in livestock feeds compromises the effectiveness of current therapies via dissemination of antibiotic resistance genes to both disease-causing and commensal microorganisms (Yan and Gilbert, 2004, *Adv. Drug Deliv. Rev.* 56, 1497-1521; DuPont, 2007, *Clin. Infect. Dis.* 45, 1353-1361).

Over 80% of the antibiotics produced in the United States are administered in swine, poultry and cattle farming. In addition to their intended use as therapeutics, antibiotics are administered throughout the life of food producing animals, even in the absence of infection to promote animal growth and improve feed efficiency (Witte, 1998, *Science* 279, 996-997; Mellon et al., 2001, Hogging it: estimates of antimicrobial abuse in livestock. Union of Concerned Scientists: Cambridge, Mass.). These growth-promoting antibiotics are applied at sub-therapeutic concentrations, establishing the conditions for development of resistance to antibiotics. Alarmingly, many of the antibiotics used in agriculture have also been listed as critically important for human health by the World Health Organization. Humans depend on many of these same antibiotics as a first line of defense against pathogens like *Escherichia coli* O157:H7, *Salmonella typhimurium, Staphylococcus aureus, Streptococcus*, and *Pseudomonas aeruginosa* (FAO, 2007, OIE, 2008: Joint FAO/WHO/OIE Expert meeting on critically important antimicrobials, in Report of a meeting held in FAO, Rome, Italy, pp 26-30).

Enterococci are commensal organisms that form part of the normal intestinal flora of humans and animals. However they are fast emerging as pathogens causing serious and life threatening hospital borne infections. Over the last three decades enterococcal strains have evolved to resist in effect all antibiotics, including vancomycin, long considered an antibiotic of last resort for many infections (Cattoir and Leclercq et al., 2013, *J Antimicrob Chemother.* 68:731-42). Antibiotic-resistant enterococci are hard to treat and account for approximately 110,000 urinary tract infections, 25,000 cases of bacteremia, 40,000 wound infections, and 1,100 cases of endocarditis annually in the USA (Huycke et al., 1998, *Emerg Infect Dis.* 4:239-49). Enterococci are the leading cause of surgical site infection, the second leading cause of nosocomial infection, the second most common pathogen for nosocomial bacteremia and bloodstream infections, and the third leading cause of urinary tract infections (Deshpande et al., 2007, *Diagn Microbiol Infect Dis.* 58:163-170; Chou et al., 2008, *J Microbiol Immunol Infect.* 41: 124-129). The potential association between the use of broad-spectrum antibiotics and the increasing incidence of atopic and autoimmune diseases is a particular cause for concern.

One promising alternative to traditional antibiotic molecules are antimicrobial peptides (AMPs). AMPs are small, often positively-charged, peptides with high antimicrobial activity. The activity of AMPs can be broad, efficiently acting on many Gram-positive and Gram-negative bacteria species. There are however AMPs with very specific activity, targeting one particular bacteria species or even a specific subspecies of a given genus (Hancock and Lehrer, 1998, *Trends Biotechnol.* 16, 82-88; Ganz and Lehrer, 1999, *Mol. Med. Today* 5, 292-297; Kokryakov et al., 1993, *FEBS letters* 327, 231-236; Cotter et al., 2013, *Nat. Rev. Microbiol.* 11, 95-105; Brogden et al., 2005, *Nat. Rev. Microb.* 3, 238-250; Marr et al., 2006, *Curr. Opin. Pharmacol.* 6, 468-472).

The current production, purification and delivery methods available for these peptides have numerous limitations. For example, solid state peptide synthesis and peptide production and purification from cell culture are both costly and time consuming (Marr et al., 2006, *Curr. Opin. Pharmacol.* 6, 468-472; Nilsson et al., 2005, *Annu. Rev. Biophys. Biomol. Struct.* 34, 91-118; Gräslund et al., 2008, *Nat. Methods* 5, 135-146). Additionally, the subsequent targeted delivery of active amounts of these compounds can be challenging. Generally, AMPs cannot be administered orally as they are quickly degraded before they are able to reach their target. AMPs cannot be administered systemically either, as they are rapidly identified and targeted for clearance by the immune system before they can reach the site of infection (Marr et al., 2006, *Curr. Opin. Pharmacol.* 6, 468-472). Moreover, high peptide concentrations are required to achieve a therapeutic effect which would be cost-prohibitive and would, more importantly, cause severe toxic side-effects. Taken together, these limitations have thus far stifled the development of AMP-based therapeutics (Marr et al., 2006, *Curr. Opin. Pharmacol.* 6, 468-472).

In recent years probiotic bacteria have emerged as useful tools for effectively boosting overall human and animal health (Oelschlaeger et al., 2010, *Int. J. Med. Microbiol.* 300, 57-62). Probiotics are typically Gram-positive, bile-resistant, bacteria that either colonize or transiently inhabit the gastrointestinal (GI) tract of a host. When administered in adequate amounts they confer health benefits by improving nutrient absorption and decreasing the relative abundance of potentially pathogenic bacteria (Health and Nutritional Properties of Probiotics in Food Including Powder Milk with Live Lactic Acid Bacteria; Report of a Joint FAO/WHO Expert Consultation, Cordoba, Argentina, 1-4 Oct. 2001; *FAO: Rome*, 1-34; Amalaradjou et al., 2012, *Adv. Food. Nutr. Res.* 67, 185-239). Lactic acid bacteria (LAB), which include microbes in the genera *Lactobacillus* and *Lactococcus*, and *Bifidobacterium*, are currently the bacteria most commonly employed as probiotics (Oelschlaeger et al., 2010, *Int. J. Med. Microbiol.* 300, 57-62; Amalaradjou et al., 2012, *Adv. Food. Nutr. Res.* 67, 185-239). A number of probiotic bacteria are currently in use as nutritional supplements for humans and animals (Lodemann et al., 2006, *Arch. Anim. Nutr.* 60, 35-48; Lyra et al., 2010, *BMC Gastroenterol.* 10, 110; Percival et al., 1997, *Clin. Nutr. Insights* 6, 1-4; Whitley et al., 2009, *J. Anim. Sci.* 87, 723-728; Gerasimov et al., 2010, *Am. J. Clin. Dermatol.* 11, 351-361; Berman et al., 2006, *Nutr. Res.* 26, 454-459; Ahmed et al., 2007, *J. Nutr. Health. Aging* 11, 26-31). In addition, recombinant LAB are also significant therapeutic delivery vectors. They are presently being tested as candidates for the delivery of therapeutics inside the GI tract of humans for the treatment of inflammatory bowel syndrome and Crohn's disease (Braat et al., 2006, *Clin. Gastroenterol. Hepatol.* 4, 754-759; Dylaq et al., 2013, Curr. Pharma. Design 10; De Greef E et al., 2013, *Acta Gastroenterol. Belg.* 76, 15-9).

SUMMARY OF THE APPLICATION

Provided herein are genetically modified microbes. In one embodiment, a genetically modified microbe includes an exogenous polynucleotide that includes a pheromone-responsive region. The pheromone-responsive region includes a pheromone-responsive promoter, and a coding region encoding an antimicrobial peptide is operably linked to the pheromone-responsive promoter. In one embodiment, the polynucleotide is integrated into the chromosome of the genetically modified microbe, and in one embodiment it is present on a vector that replicates independently of the chromosome of the genetically modified microbe.

In one embodiment, a genetically modified microbe includes an exogenous first coding region operably linked to a pheromone-responsive promoter. The first coding region is typically part of a pheromone-responsive region. The expression of the first coding region by the pheromone-responsive promoter is repressed by a modulator polypeptide, and the first coding region encodes an antimicrobial peptide. The repression of the pheromone-responsive promoter is inhibited by a modulating agent selected from ALFSLVLAG (SEQ ID NO:33), LVTLVFV (SEQ ID NO:32), FLVMFLSG (SEQ ID NO:34), and AIFILAS (SEQ ID NO:35). The genetically modified microbe also includes second exogenous coding sequence operably linked to a promoter, wherein the second coding region encodes the modulator polypeptide.

In one embodiment, the pheromone-responsive region includes a nucleotide sequence that is essentially identical to nucleotides 1-1640 of SEQ ID NO:1, and in such an embodiment the complement of nucleotides 79-1027 of SEQ ID NO:1 may encode a polypeptide that is essentially identical to SEQ ID NO:3. In one embodiment, the pheromone-responsive region includes a prgQ coding region, wherein the prgQ coding region comprises a deletion of at least one codon encoding an amino acid of the PrgQ polypeptide. In one embodiment, the deletion includes codon ACC at nucleotides 1290-1292 of SEQ ID NO:1.

In one embodiment, the pheromone-responsive region includes a nucleotide sequence that is essentially identical to the nucleotide sequence of SEQ ID NO:5, and in such an embodiment the complement of nucleotides 6-968 of SEQ ID NO:5 may encode a polypeptide that is essentially identical to SEQ ID NO:53.

In one embodiment, the pheromone-responsive region includes a nucleotide sequence that is essentially identical to the nucleotide sequence of SEQ ID NO:6, and in such an embodiment the complement of nucleotides 10-969 of SEQ ID NO:6 may encode a polypeptide that is essentially identical to SEQ ID NO:54.

In one embodiment, the pheromone-responsive region includes a nucleotide sequence that is essentially identical to the nucleotide sequence of SEQ ID NO:7, and in such an embodiment the complement of nucleotides 1-1014 of SEQ ID NO:7 may encode a polypeptide that is essentially identical to SEQ ID NO:55.

In one embodiment, the genetically modified microbe further includes a coding region encoding a pheromone binding polypeptide that is essentially identical to SEQ ID NO:4. In one embodiment, the antimicrobial peptide is EntA, EntP, Hiracin, Protegrin, or a combination thereof, such as at least 2, or at least 3 coding regions encoding antimicrobial peptides, wherein each coding region is operably linked to the pheromone-responsive promoter.

In one embodiment, the genetically modified microbe is a lactic acid bacterium. In one embodiment, the lactic acid bacterium is a *Lactococcus* spp., such as *L. lactis*. In one embodiment, lactic acid bacterium is a *Lactobacillus* spp., such as *Lb. acidophilus, Lb. bulgaricus, Lb. reuteri*, or *Lb. plantarum*.

Also provided herein are vectors. In one embodiment, a vector includes a polynucleotide having a pheromone responsive region that includes a pheromone-responsive promoter. The pheromone-responsive region is essentially identical to nucleotides 1-1640 of SEQ ID NO:1, essentially identical to the nucleotide sequence of SEQ ID NO:5, essentially identical to the nucleotide sequence of SEQ ID NO:6, or essentially identical to the nucleotide sequence of SEQ ID NO:7. The pheromone-responsive promoter is operably linked to a coding region encoding at least on antimicrobial peptide. In one embodiment, a vector further includes a coding region that encodes a modulator polypeptide that represses the pheromone-responsive promoter.

Also provided herein are methods of using the genetically modified microbes. In one embodiment, the method is for inhibiting growth of an *Enterococcus* spp. The method includes combining a first composition that includes a genetically modified microbe described herein with a second composition that include the *Enterococcus* spp. to form a mixture. The mixture is incubated under conditions suitable for replication of the genetically modified microbe, and the genetically modified microbe expresses the antimicrobial peptide when it senses the presence of the *Enterococcus* spp. In one embodiment, the method includes administering the composition with the genetically modified microbe to a subject, and the mixture is present in the gastrointestinal tract of the subject.

In one embodiment, the method is for treating a subject. In one embodiment, the method includes administering to a subject in need thereof an effective amount of a composition that includes a genetically modified microbe described herein. In one embodiment, the subject has or is at risk for having an *Enterococcus* spp. in the gastrointestinal tract, such as an antibiotic resistant *Enterococcus* spp. In one embodiment, the *Enterococcus* spp. is *E. faecalis* or *E. faecium*.

In one embodiment, the method is for modifying a subject's gastrointestinal microflora. In one embodiment, the method includes administering to the subject a composition that includes a genetically modified microbe described herein. In one embodiment, the subject has or is at risk for having an *Enterococcus* spp. in the gastrointestinal tract, such as an antibiotic resistant *Enterococcus* spp. In one embodiment, the *Enterococcus* spp. is *E. faecalis* or *E. faecium*.

Also provided herein is a system includes (a) a microbe; and (b) a first exogenous polynucleotide. The polynucleotide may include a pheromone responsive region that is essentially identical to nucleotides 1-1640 of SEQ ID NO:1, essentially identical to the nucleotide sequence of SEQ ID NO:5, essentially identical to the nucleotide sequence of SEQ ID NO:6, or essentially identical to the nucleotide sequence of SEQ ID NO:7. The pheromone-responsive region includes a pheromone-responsive promoter, wherein a coding region encoding an antimicrobial peptide is operably linked to the pheromone-responsive promoter. In one embodiment, the microbe is a *Lactococcus* spp. or a *Lactobacillus* spp.

As used herein, the term "polypeptide" refers broadly to a polymer of two or more amino acids joined together by peptide bonds. The term "polypeptide" also includes molecules which contain more than one polypeptide joined by a disulfide bond, or complexes of polypeptides that are joined together, covalently or noncovalently, as multimers (e.g., dimers, trimers, tetramers). Thus, the terms peptide, oligopeptide, enzyme, subunit, and protein are all included within the definition of polypeptide and these terms are used interchangeably. It should be understood that these terms do not connote a specific length of a polymer of amino acids, nor are they intended to imply or distinguish whether the polypeptide is produced using recombinant techniques, chemical or enzymatic synthesis, or is naturally occurring.

As used herein, the term "polynucleotide" refers to a polymeric form of nucleotides of any length, either ribonucleotides or deoxynucleotides, and includes both double- and single-stranded RNA and DNA. A polynucleotide can be obtained directly from a natural source, or can be prepared with the aid of recombinant, enzymatic, or chemical techniques. A polynucleotide can be linear or circular in topology. A polynucleotide may be, for example, a portion of a vector, such as an expression or cloning vector, or a fragment. A polynucleotide may include nucleotide sequences having different functions, including, for instance, coding regions, and non-coding regions such as regulatory regions.

As used herein, the terms "coding region," "coding sequence," and "open reading frame" are used interchangeably and refer to a nucleotide sequence that encodes a polypeptide and, when placed under the control of appropriate regulatory sequences expresses the encoded polypeptide. The boundaries of a coding region are generally determined by a translation start codon at its 5' end and a translation stop codon at its 3' end. A "regulatory sequence" is a nucleotide sequence that regulates expression of a coding sequence to which it is operably linked. Non-limiting examples of regulatory sequences include promoters, enhancers, transcription initiation sites, translation start sites, translation stop sites, and transcription terminators. The term "operably linked" refers to a juxtaposition of components such that they are in a relationship permitting them to function in their intended manner. A regulatory sequence is "operably linked" to a coding region when it is joined in such a way that expression of the coding region is achieved under conditions compatible with the regulatory sequence.

As used herein, "genetically modified microbe" refers to a microbe which has been altered "by the hand of man." A genetically modified microbe includes a microbe into which has been introduced an exogenous polynucleotide, e.g., an expression vector.

As used herein, a "vector" is a replicating polynucleotide, such as a plasmid, to which another polynucleotide may be attached so as to bring about the replication of the attached polynucleotide.

As used herein, an "exogenous polypeptide" and "exogenous polynucleotide" refers to a polypeptide and polynucleotide, respectively, that is not normally or naturally found in a microbe, and/or has been introduced into a microbe. An exogenous polynucleotide may be separate from the genomic DNA of a cell (e.g., it may be a vector, such as a plasmid), or an exogenous polynucleotide may be integrated into the genomic DNA of a cell.

Conditions that are "suitable" for an event to occur, such as expression of an exogenous polynucleotide in a cell to produce a polypeptide, or production of a product, or "suitable" conditions are conditions that do not prevent such events from occurring. Thus, these conditions permit, enhance, facilitate, and/or are conducive to the event.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIGS. 1a and 1b show a synthetic antimicrobial peptide (AMP) screen against *E. coli*, *Salmonella* and *L. lactis*. (FIG. 1a) Alyteserin and (FIG. 1b) A3APO were diluted and applied to *E. coli*, *Salmonella* and *L. lactis* IL1403. Inhibitory concentrations for *E. coli* and *Salmonella* are emphasized in boxed areas, the smallest of which is the MIC observed for each Gram-negative pathogen and AMP combination. *L. lactis* growth inhibition was not achieved by any AMP concentration tested.

FIGS. 2a and 2b show *E. coli* growth inhibition by Alyteserin. (FIG. 2a) Pathogenic (grey bars) and non-pathogenic (white bars) *E. coli* are inhibited by Alyteserin. Cultures grown in the presence of Alyteserin achieved a density 20-fold lower than the cultures grown in control supernatant (C-SN). (FIG. 2b) Pathogenic and non-pathogenic *E. coli* growth was inhibited by when cultured in Alyteserin supernatant (Alys-SN) (triangles) relative to the control supernatant (circles) through 15 h post-inoculation.

FIGS. 3a and 3b show *Salmonella* growth inhibition by Alyteserin and A3APO. (FIG. 3a) *Salmonella infantis* (grey bars) and *typhimurium* (white bars) are both inhibited by Alyteserin and A3APO. *S. infantis* culture density, in the presence of Alyteserin, was reduced by about one-half and *S. typhimurium* was reduced by 10-fold. *S. infantis* cultures grown in the presence of A3APO achieved a density 20-fold less than the cultures in the control supernatant while *S. typhimurium* culture density was reduced by 4-fold. (FIG. 3b) *Salmonella* growth is inhibited by 15% when cultured in the presence of Alyteserin (triangles) relative to the control supernatant (circles) through 15 h post-inoculation. Growth inhibition by A3APO is not observed at these longer times however (squares).

FIGS. 5B-1 through 5B-7. The nucleotide sequence of the plasmids pBK1, pBK2, and pBK2idT. The nucleotide sequence (SEQ ID NO:1) of pBK2 is shown. The nucleotide sequence of pBK1 is identical pBK2, but pBK1 does not include nucleotides 1-1044. The nucleotide sequence of pBK2idT is identical pBK2, but pBK2idT does not include nucleotides 1290-1292. The coding regions for prgX, prgQ, lacZ, cat, and repB are shown, and the ColE1 origin of replication is also shown.

FIGS. 6-1 and 6-2 show the nucleotide sequence (SEQ ID NO:2) of the P23 promoter and an operably linked prgZ coding region.

FIG. 7. LacZ-activity in Miller Units (M.U.) of *L. lactis* NZ9000 transformed with different recombinant vectors.

FIGS. 8-1 and 8-2 show the nucleotide sequence (SEQ ID NO:59) of the Bac fragment described in Table 7 of coding regions entA, hirJM79, entP, and Lys170, and the corresponding proteins encoded by the coding regions (SEQ ID NO:60, SEQ ID NO:62, SEQ ID NO:64, and SEQ ID NO:66, respectively), and immunity coding regions entiA, hiriJM79, entiP and the corresponding proteins encoded by the coding regions (SEQ ID NO:61, SEQ ID NO:62, and SEQ ID NO:65, respectively) are shown. The ribosome binding sites are underlined.

FIGS. 9-1 through 9-5 show the nucleotide sequences of promoters and coding sequence encoding corresponding repressor polypeptides. SEQ ID NO:8 includes a tetracyline promoter and coding region encoding a tetacyline repressor. SEQ ID NO:9 includes a lactose promoter and coding region encoding a lactose repressor. SEQ ID NO:10 includes a xylose promoter and coding region encoding a xylose repressor. Terminator, nucleotides corresponding to a transcription terminator; Ptet, nucleotides corresponding to a tet promoter; PC64a, nucleotides encoding a PC64a antimicrobial peptide; PnisA, nucleotides corresponding to a nisA promoter; tetR, nucleotides encoding a tet repressor; gfp, nucleotides encoding green fluorescent protein; Plac, nucleotides corresponding to a lac promoter; Alysteserin, nucleotides encoding an Alysteserin antimicrobial peptide; lad, nucleotides encoding a lac repressor; Pxyl, nucleotides corresponding to a xyl promoter; A3-APO, nucleotides encoding an A3-APO antimicrobial peptide; xylR, nucleotides encoding a xyl repressor.

FIG. 10. Amino acid sequences of PrgX (SEQ ID NO:3) and PrgZ (SEQ ID NO:4).

FIGS. 11-1 through 11-3 show the nucleotide sequences of pheromone-responsive regions. pPD1, SEQ ID NO:5; pAD1, SEQ ID NO:6; pAM373, SEQ ID NO:7. The underlined nucleotides of pPD1, pAD1, and pAM373 encode TraA, an analog of PrgX. The double underlined nucleotides of pPD1, pAD1, and pAM373 encode Ipd, Iad, and i373, respectively, analogs of PrgQ, the negative regulators of the pheromone-responsive promoters disclosed herein.

DETAILED DESCRIPTION OF ILLUSTRATIVE EMBODIMENTS

Figure 1:
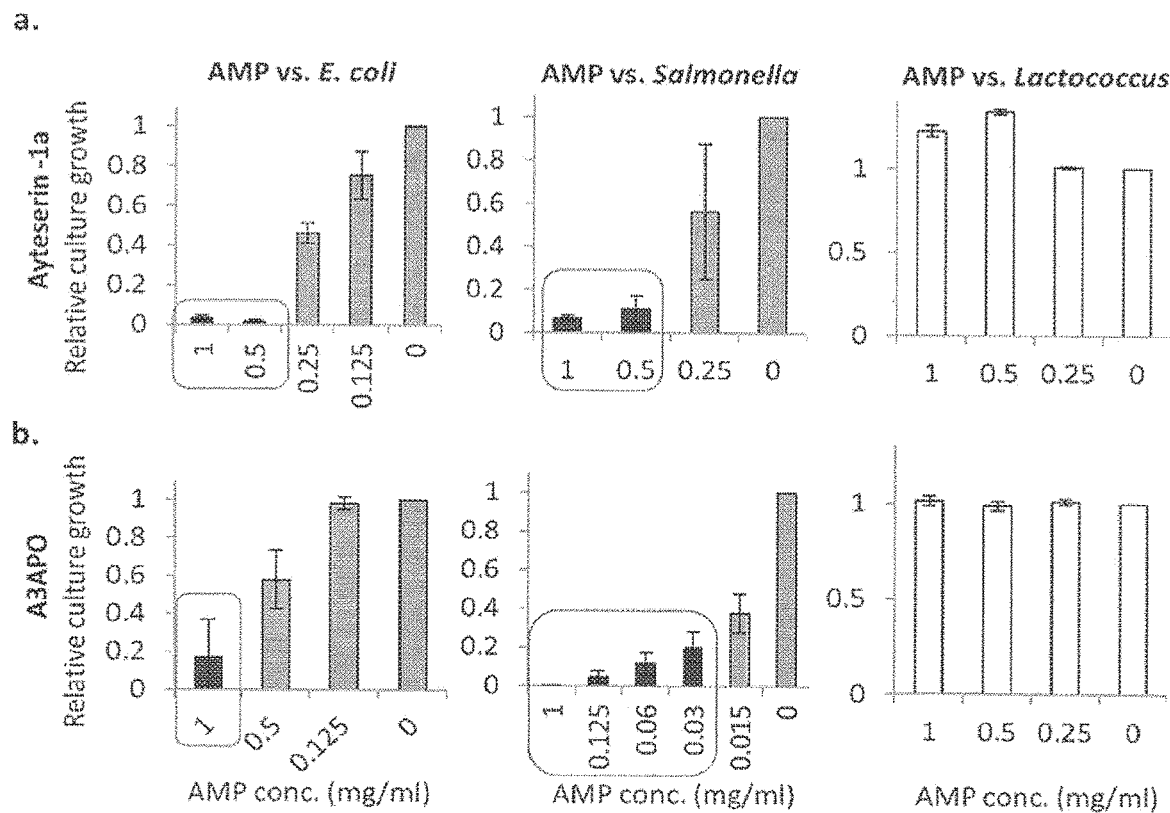

Provided herein are vectors. In one embodiment, a vector includes a first coding sequence operably linked to a first promoter, and a second coding sequence operably linked to a second promoter. The first promoter is a controllable promoter and the first coding sequence encodes one or more antimicrobial peptides (AMPs). The second coding region encodes a polypeptide that regulates the expression of the first promoter. Thus, the vectors described herein are a system for controlling expression of antimicrobial peptides. In one embodiment described herein, a genetically modified microbe expresses antimicrobial peptides only when it has sensed the presence of a predetermined target microbe.

The first coding sequence encodes an antimicrobial peptide. Antimicrobial peptides are small proteins, typically between 10 and 100 amino acids in length that inhibit, and often kill, certain bacteria. An antimicrobial peptide may affect the structural integrity of bacteria cell membranes, permeabilize the membrane of bacteria, and/or induce the collapse of cell transmembrane potential. In one embodiment, an antimicrobial peptide has antimicrobial activity for Gram negative microbes that is greater that the antimicrobial activity it has against Gram positive microbes. In one embodiment, an antimicrobial peptide has essentially similar antimicrobial activity for Gram negative microbes and Gram positive microbes. In one embodiment, an antimicrobial peptide has antimicrobial activity for Gram positive microbes that is greater that the antimicrobial activity it has against Gram negative microbes. In one embodiment, multiple coding regions may be operably linked to the first promoter. For instance, 1, 2, 3, or more coding regions may be operably linked, resulting in the expression of more than one antimicrobial peptide. In one embodiment, the multiple coding regions may be arranged to form an operon.

An antimicrobial peptide has antimicrobial activity that inhibits or kills a target microbe, for instance, *E. coli*, a member of the genus *Salmonella*, and/or a member of the genus *Enterococcus*. Examples of *Enterococcus* spp. include, for instance, *E. faecalis* and *E. faecium*. The target microbe may be in vitro or in vivo. In one embodiment, the antimicrobial peptide may disrupt the integrity of the bacterial cell membrane, which results in the collapse of the transmembrane potential across the membrane and the subsequent osmotic lysis of the cells. In another embodiment, an antimicrobial peptide may act as an immunomodulator of an animal's immune system. For instance, an antimicrobial peptide may induce animal immune cells to produce cytokines and/or chemokines, and attract and/or activate immune cells. Such immune system activation may aid in the clearance of a pathogenic microbe.

Whether an antimicrobial peptide has antimicrobial activity can be determined using different indicator strains. Examples of indicator strains include, but are not limited to, pathogenic *Salmonella*, enterohemorrhagic *E. coli* O157:H7, lactic acid bacteria such as *Lactococcus lactis*, *Lactobacillus acidophilus* and *Lb. bulgaricus*, and *Enterococcus* spp. Examples of suitable indicator strains include, but are not limited to, those listed in Table 1. In one embodiment, an indicator strain is a member of the genus *Enterococcus*, such as *E. faecalis* and *E. faecium*. Methods for testing the activity of an AMP include, but are not limited to, the stab-on-agar test as well as other methods useful for evaluating the activity of bacteriocins. Such methods are known in the art and are routine.

TABLE 1

Examples of indicator strains.

*Escherichia coli* serotype O157:H7
*Salmonella enterica* subsp enterica
serovar *Typhimurium*
serovar *Tennessee*
serovar *St Paul*
serovar *Infantis*
*Lactococcus lactis* subsp lactis IL1403
*Lactobacillus acidophilus* ATCC 4356
*Lactobacillus bulgaricus* ATCC 11842

TABLE 1-continued

Examples of indicator strains.

*Enterococcus faecalis* ATCC 700802
*Enterococcus faecalis* ATCC 47077

An antimicrobial peptide may be naturally occurring or may be engineered. Antimicrobial peptides are produced by all classes of organisms, including mammals, bacteria, and phage. Examples of antimicrobial peptides are shown in Table 2. Examples of antimicrobial peptides from bacteria are bacteriocins, and include class I and class II bacteriocins. An example of class II bacteriocins includes members of the subclass IIa bacteriocins. Class IIa bacteriocins are small (usually 37 to 48 amino acid), heat-stable, and non-post-translationally modified proteins that are typically positively charged and may contain an N-terminal consensus sequence -Tyr-Gly-Asn-Gly-(Val/Lys)-Xaa-Cys- (for example SEQ ID NO:11, SEQ ID NO:12, SEQ ID NO:13). Examples of bacteriocins include, but are not limited to, those described in Table 2. Another example of antimicrobial peptides includes endolysins. Endolysins are double-stranded DNA bacteriophage-encoded peptidoglycan hydrolases produced in phage-infected bacterial cells, and cause rapid lysis when applied to Gram-positive bacteria (Fenton et al., 2010, Bioeng Bugs. 1:9-16; Fischetti, 2008, Curr Opin Microbiol. 11:393-400). Other antimicrobial peptides are known to the person skilled in the art and may also be used as described herein. The present invention is not limited by the antimicrobial peptide.

TABLE 2

| Antimicrobial Peptide | Amino acid sequence | Origin |
|---|---|---|
| Enterocin A (EntA) | TTHSGKYYGNGVYCTKNKCTVDWAKATTCIAGMSIGGFLGGAI PGIKC (SEQ ID NO: 11) | *E. faecium* (1) |
| Enterocin P (EntP) | ATRSYGNGVYCNNSKCWVNWGEAKENIAGIVISGWASGLAG MGH (SEQ ID NO: 12) | *E. faecium* (2) |
| Hiracin JM79 (HirJM79) | ATYYGNGLYCNKEKCWVDWNQAKGEIGKIIVNGWVNHGPW APRR (SEQ ID NO: 13) | *E. hirae* (3) |
| Protegrin 1 (PG-1) | RGGRLCYCRRRFCVCVGR (SEQ ID NO: 14) | Pig leukocyte (5) |
| PC64A | LTYCRRRFCVTV (SEQ ID NO: 15) | PG-1 analogue (6) |
| A3-APO | RPDKPRPYLPRPRPPRPVR (SEQ ID NO: 16) | Engineered antimicrobial peptide (7) |
| Alyteserin-1a | GLKDIFKAGLGSLVKGIAAHVAN (SEQ ID NO: 17) | Peptide from the skin of the frog *Alytes obstetricans* (8) |
| Fowlicidin | RVKRVWPLVIRTVIAGYNLYRAIKKK (SEQ ID NO: 18) | Cathelicidin from chicken (9) |
| Microcin 24 | AGDPLADPNSQIVRQIMSNAAWGPPLVPERFRGMAVGAAG GVTQTVLQGAAAHMPVNVPIPKVPMGPSWNGSKG (SEQ ID NO: 19) | *Escherichia coli* (10) |
| Colicin V | ASGRDIAMAIGTLSGQFVAGGIGAAAGGVAGGAIYDYASTHK PNPAMSPSGLGGTIKQKPEGIPSEAWNYAAGRLCNWSPNNLS DVCL (SEQ ID NO: 20) | *Escherichia coli* (11) |
| Acidocin LCHV NP | NVGVLNPPPLV (SEQ ID NO: 21) | Bacteriocin from *Lb. acidophilus* n.v. Er 317/402 strain Narine (12) |
| Acidocin LCHV HV | NVGVLNPPMLV (SEQ ID NO: 22) | Bacteriocin from *Lb. acidophilus* n.v. Er 317/402 strain Narine (12) |

TABLE 2-continued

| Antimicrobial Peptide | Amino acid sequence | Origin |
|---|---|---|
| Acidocin LCHV LP | NVGVLLPPPLV (SEQ ID NO: 23) | Bacteriocin from Lb. acidophilus n.v. Er 317/402 strain Narine (12) |
| Acidocin LCHV LM | NVGVLLPPMLV (SEQ ID NO: 24) | Bacteriocin from Lb. acidophilus n.v. Er 317/402 strain Narine (12) |
| LGG NPSRQERR | NPSRQERR (SEQ ID NO: 25) | Small bioactive peptide from Lactobacillus GG (12) |
| LGG PDENK | PDENK (SEQ ID NO: 26) | Small bioactive peptide from Lactobacillus GG (13) |
| Endolysin 170 (Lys170) | MAGEVFSSLITSVNPNPMNAGSRNGIPIDTIILHHNATTNKDV AMNTWLLGGGAGTSAHYECTPTEIIGCVGEQYSAFHAGGTGG IDVPKIANPNQRSIGIENVNSSGAPNWSVDPRTITNCARLVADI CTRYGIPCDRQHVLGHNEVTATACPGGMDVDEVVRQAQQF MAGGSNNAVKPEPSKPTPSKPSNNKNKEGVATMYCLYERPIN SKTGVLEWNGDAWTVMFCNGVNCRRVSHPDEMKVIEDIYRK NNGKDIPFYSQKEWNKNAPWYNRLETVCPVVGITKKS (SEQ ID NO: 27) | E. faecalis phage F170/08 (4) |
| PlyV12 | MSNINMETAIANMYALKARGITYSMNYSRTGADGTGDCSGTV YDSLRKAGASDAGWVLNTDSMHSWLEKNGFKLIAQNKEWSA KRGDVVIFGKKGASGGSAGHVVIFISSTQIIHCTWKSATANGVY VDNEATTCPYSMGWYVYRLNGGSTPPKPNTKKVKVLKHATN WSPSSKGAKMASFVKGGTFEVKQQRPISYSYSNQEYLIVNKGT VLGWVLSQDIEGGYGSDRVGGSKPKLPAGFTKEEATFINGNAP ITTRKNKPSLSSQTATPLYPGQSVRYLGWKSAEGYIWIYATDGR YIPVRPVGKEAWGTFKQDIEGGYGSDRVGGSKPKLPAGFTKEE ATFINGNAPITTRKNKPSLSSQTATPLYPGQSVRYLGWKSAEGY IWIYATDGRYIPVRPVGKEAWGTFK (SEQ ID NO: 28) | Encoded by phage F1 (14) |
| EFAL-1 | MKLKGILLSVVTTFGLLFGATNVQAYEVNNEFNLQPWEGSQQ LAYPNKIILHETANPRATGRNEATYMKNNWFNAHTTAIVGDG GIVYKVAPEGNVSWGAGNANPYAPVQIELQHTNDPELFKANY KAYVDYTRDMGKKFGIPMTLDQGGSLWEKGVVSHQWVTDF VWGDHTDPYGYLAKMGISKAQLAHDLANGVSGNTATPTPKP DKPKPTQPSKPSNKKRFNYRVDGLEYVNGMWQIYNEHLGKID FNWTENGIPVEVVDKVNPATGQPTKDQVLKVGDYFNFQENST GVVQEQTPYMGYTLSHVQLPNEFIWLFTDSKQALMYQ (SEQ ID NO: 29) | Produced by phage EFAP-1 (15) |
| ORF9 | MAGEVFSSLITSVNPNPMNAGSRNGIPIDTIILHHNATTNKDV AMNTWLLGGGAGTSAHYECTPTEIIGCVGEQYSAFHAGGTGG IDVPKIANPNQRSIGIENVNSSGAPNWSVDPRTITNCARLVADI CTRYGIPCDRQHVLGHNEVTATACPGGMDVDEVVRQAQQF MAGGSNNAVKPEPSKPTPSKPSNNKNKEGVATMYCLYERPIN SKTGVLEWNGDAWTVMFCNGVNCRRVSHPDEMKVIEDIYRK NNGKDIPFYSQKEWNKNAPWYNRLETVCPVVGITKKS (SEQ ID NO: 30) | From phage jEF24C (16) |
| Lys168 | MVKLNDVLSYVNGLVGKGVDADGWYGTQCMDLTVDVMQR FFGWRPYGNAIALVDQPIPAGFQRIRTTSSTQIKAGDVMIWGL GYYAQYGHTHIATEDGRADGTFVSVDQNWINPSLEVGSPAAA IHHNMDGVWGVIRPPYEAESKPKPPAPKPDKPNLGQFKGDD DIMFIYYKKTKQGSTEQWFVIGGKRIYLPTMTYVNEANDLIKRY GGNTNVTTYNYDNFGLAMMEKAYPQVKL (SEQ ID NO: 31) | From phage F168/08 (17) |

1. Aymerich et al., 1996, Appl Environ Microbiol. 62: 1676-1682; 2. Cintas et al., 1997, Appl Environ Microbiol., 63: 4321-4330; 3. Sánchez et al., 2007, FEMS Microbiol Lett. 270: 227-236; 4. Proença et al., 2012, Microb Drug Resist., 18: 322-332; 5. Fahrner et al., 1996, Chemistry & Biology 3: 543-550; 6, Chang et al., U.S. Pat. No. 5,994,306; 7. Szabo et al., 2010, International journal of antimicrobial agents 35: 357-361; 8. Conlon et al., 2009, Peptides 30, 1069-1073; 9. Xiao, 2005, Journal of Biological Chemistry 281: 2858-2867; 10. O'Brien et al., 1994, Plasmid 31: 288-296; 11. Gillor et al., 2004, Advances in applied microbiology 54: 129-146; 12. Mkrtchyan et al., 2010, International journal of antimicrobial agents 35: 255-260; 13. Lu et al., 2009, J. Pediatr. Gastroenterol. Nutr. 49: 23-30; 14. Yoong et al., 2004, J. Bacteriol. 186: 4808-4812; 15. Uchiyama et al., 2011, Appl Environ Microbiol. 77: 580-585; 16. Son et al., 2010, J. Appl Microbiol. 108: 1769-1779; 17. Proença et al., 2012, .Microb Drug Resist. 18: 322-332.

Examples of antimicrobial peptides also include those that are essentially identical to any one of the AMPS in Table 2. As used herein, in the context of a polypeptide "essentially identical" refers to a polypeptide that differs from one of the polypeptides disclosed herein. A polypeptide that is essentially identical to an AMP differs from one of the AMPS in Table 2 at 1, 2, 3, 4, 5, 6, 7, 8, 9, 10, 11, or 12 amino acid residues and has antimicrobial activity. In one embodiment, the difference is a conservative substitution. Conservative amino acid substitutions are defined to result from exchange of amino acids residues from within one of the following classes of residues: Class I: Ala, Gly, Ser, Thr, and Pro (representing small aliphatic side chains and hydroxyl group side chains); Class II: Cys, Ser, Thr, and Tyr (representing side chains including an —OH or —SH group); Class III: Glu, Asp, Asn, and Gln (carboxyl group containing side chains); Class IV: His, Arg, and Lys (representing basic side chains); Class V: Ile, Val, Leu, Phe, and Met (representing hydrophobic side chains); and Class VI: Phe, Trp, Tyr, and His (representing aromatic side chains).

A nucleotide sequence of a coding sequence encoding an antimicrobial peptide may be easily predicted based on reference to the standard genetic code. When an antimicrobial peptide is to be expressed in a particular microbe, a nucleotide sequence encoding the antimicrobial peptide may be produced with reference to preferred codon usage for the particular microbe.

The first coding sequence may further include nucleotides encoding a secretion signaling polypeptide, such that the antimicrobial peptide and the secretion signaling polypeptide are fused and expressed as a single polypeptide. A secretion signaling polypeptide targets a polypeptide for secretion out of the cell. A secretion signaling polypeptide is usually present at the amino-terminal end of a polypeptide. Secretion signaling polypeptides useful in prokaryotic microbes are known in the art and routinely used. Examples of secretion signaling polypeptides useful in lactic acid bacteria, including *L. lactis, Lb. acidophilus, Lb. acidophilus, Lb. bulgaricus, Lb. reuteri*, and *Lb. plantarum* are known. One example of a useful secretion signaling polypeptide is from the protein Usp45 (Van Asseldonk et al., 1990, Gene, 95, 155-160).

The first promoter controls expression of the operably linked coding region encoding an antimicrobial peptide. The first promoter may be a controllable promoter, such as an inducible promoter or a repressible promoter. Examples of controllable promoters include promoters to which a modulating polypeptide binds to inhibit or activate transcription in the presence of a modulating agent. Modulating polypeptides and modulating agents are described below.

Examples of such promoters include the tetracycline promoter, the lactose promoter, the xylose promoter, and the PnisA promoter. Such controllable promoters are known in the art and are routinely used to control expression of operably linked coding regions in prokaryotes. Such promoters often include −35 and −10 regions with an operator site also present, typically between the −35 and −10 regions. Variants of known controllable promoters may be produced and used as described herein.

An example of a useful tetracycline promoter is shown at nucleotides 64 to 182 of SEQ ID NO:8). An example of a useful lactose promoter is shown at nucleotides 64 to 200 of SEQ ID NO: 9). An example of a useful xylose promoter is shown at nucleotides 64 to 234 of SEQ ID NO: 10). An example of other useful promoters include those described in Volzing et al. (ACS Chem. Biol., 2011, 6:1107-1116).

The second coding sequence of the vectors described herein encode a modulating polypeptide. A modulating polypeptide is a polypeptide that modulates expression of a coding sequence operably linked to a first promoter described herein. In one embodiment, a modulating polypeptide binds to a promoter or to other nucleotides around the promoter and modulates expression of a coding sequence operably linked to that promoter. The modulating polypeptide may either induce or prevent expression of the operably linked coding sequence in the presence of a modulating agent. Examples of modulating polypeptides that bind to a tetracycline promoter are known in the art and include tetracycline repressor proteins, reverse tetracycline repressor proteins, as well as synthetic repressor and activator proteins PROTEON and PROTEOFF described in Volzing et al. (ACS Chem. Biol., 2011, 6:1107-111). Modulating agents that interact with tetracycline repressor proteins, reverse tetracycline repressor proteins, PROTEON and PROTEOFF proteins include tetracycline, doxycycline and anhydrotetracycline (aTc). Examples of modulating polypeptides that bind to a lactose promoter are known in the art and include lac-repressor, and modulating agents that interact with a lac-repressor include lactose, and isopropyl β-D-1-thiogalactopyranoside (IPTG). Examples of modulating polypeptides that bind to a xylose promoter are known in the art and include xyl-repressor, and modulating agents that interact with a xyl-repressor include xylose. Examples of modulating polypeptides that bind to a PnisA promoter are known in the art and include NisR polypeptide.

The second promoter controls expression of the operably linked coding region encoding a modulating polypeptide. The second promoter may be a constitutive promoter. Examples of constitutive promoters include, but are not limited to, P23 and PnisR. These and other constitutive promoters are known in the art and routinely used to control expression of operably linked coding regions in prokaryotes. Variants of known constitutive promoters may be produced and used as described herein.

In one embodiment, the first promoter and the second promoter are part of a pheromone-responsive region. A pheromone-responsive region includes a first promoter, also referred to as a pheromone-responsive promoter, which is a controllable promoter where expression of an operably linked coding sequence is repressed in the presence of a modulating peptide, and is induced in the presence of a modulating agent. In the context of a pheromone-responsive promoter, a modulating agent may be referred to as a pheromone.

Examples of pheromone-responsive regions are found in many conjugative plasmids of *E. faecalis* (Clewell and Dunny, 2002, In: The Enterococci: Pathogenesis, Molecular Biology, and Antibiotic Resistance, Eds Gilmore et al., ASM Press, pp. 265-300; Wirth, 1994, Eur. J. Biochem., 222:235-246). The conjugative plasmids of *E. faecalis* are a family of mobile genetic elements whose ability to transfer from a donor to a recipient bacterial cell is controlled by intercellular signaling via a pheromone peptide. The pheromone-responsive regions present on these conjugative plasmids include a pheromone-responsive promoter and a second promoter that drives expression of a modulating peptide. These two promoters correspond to the first promoter and second promoter described for the vectors of the present invention. The two promoters are in opposite orientations that overlap and face each other in a convergent transcription configuration, where a first promoter is repressed by a modulating peptide, and the modulating peptide is expressed by the second promoter. As a result, these promoters display a very tight bistable switch behavior; expression of the first promoter is essentially off until a threshold of pheromone concentration is reached.

One example of a conjugative plasmid of *E. faecalis* is pCF10. Donor cells carrying pCF10 are induced to high expression of conjugative transfer by a pheromone peptide. Donor cells import the pheromone peptide into the cytoplasm, where its binding to the pCF10-encoded modulator peptide PrgX abolishes repression of transcription of the prgQ operon encoding the conjugation genes. The mating response of donor cells to the pheromone peptide is encoded by pCF10, whereas the pheromone peptide is produced from a conserved chromosomal gene present in most if not all *E.* faecalis strains (Chatterjee et al., 2013, Proc Natl Acad Sci USA. 110: 7086-7090). Donor *E. faecalis* cells harboring pCF10 produce reduced levels of the pheromone (Buttaro et al., 2000, J Bacteriol. 182: 4926-33). This residual pheromone activity is neutralized by the production of the peptide iCF10 from the prgQ locus of pCF10, which negatively regulates the promoter for the prgQ operon. Therefore the molar ratio of chromosomally encoded pheromone peptide to plasmid-encoded inhibitor (iCF10) determines the induction state of the donor cell (Nakayama et al., 1994, J Bacteriol. 176: 7405-7408).

The pheromone-responsive regions of the conjugative plasmids are complex, with transcriptional interference and sense-antisense regulation playing roles in the regulation of expression of the prgQ locus. Further, in the pCF10 plasmid the effect of the pheromone peptide on transcription from the prgQ locus is enhanced greatly by several co-transcriptional and post-transcriptional mechanisms (Chatterjee et al., 2011, PNAS, 108:9721-9726; Chatterjee et al., 2013, PNAS, 110: 7086-7090). For these reasons, it was surprising to find that a relatively small region of the pCF10 conjugative plasmid could be expressed in a non-Enterococcal cell yet retain sensitivity to a pheromone peptide and the ability to be regulated by a pheromone peptide.

Figure 5A:
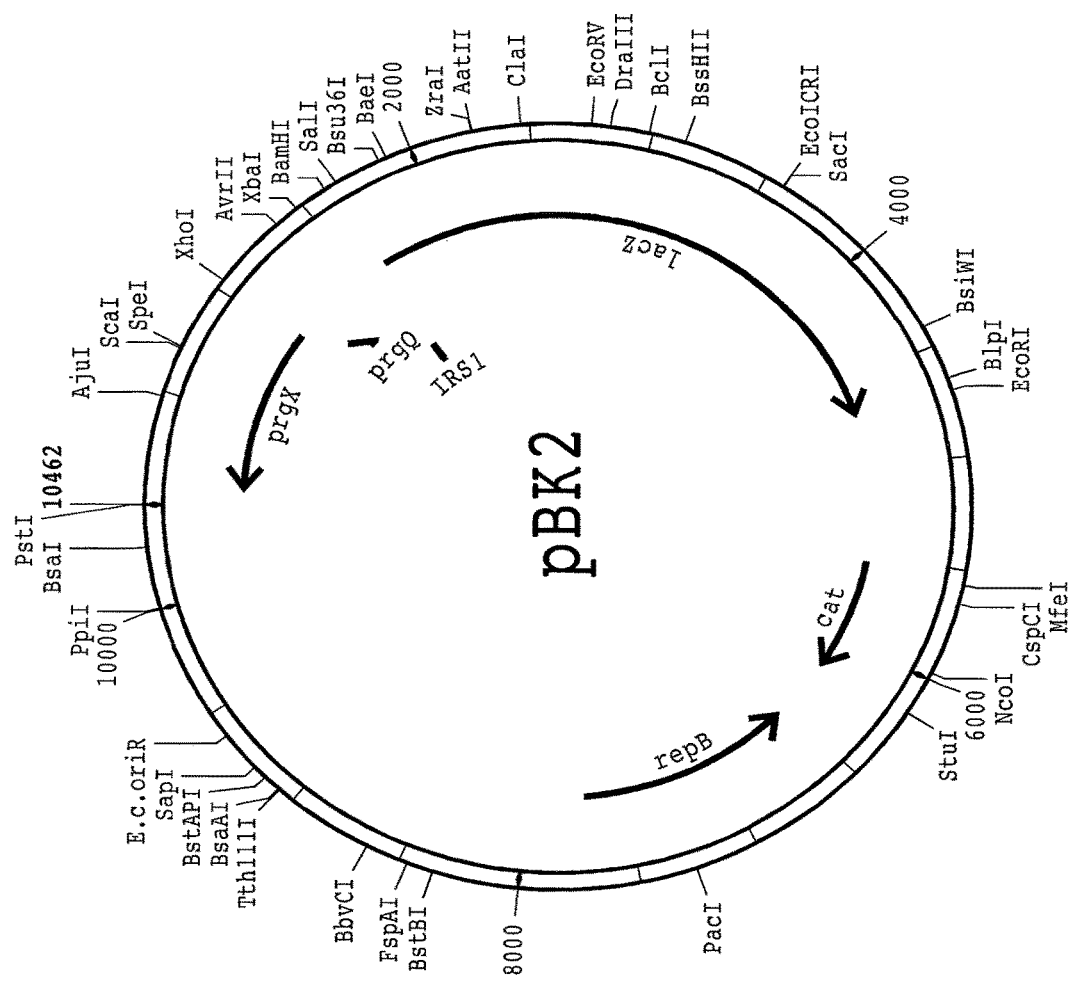
FIG. 5A. A schematic of pBK2.

An example of a pheromone-responsive region present on a pCF10 conjugative plasmid is shown in FIG. 5. In one embodiment, a pheromone-responsive region includes nucleotides 1-1640 of SEQ ID NO:1. In one embodiment, a pheromone-responsive region includes nucleotides 80-1640 of SEQ ID NO:1. In this embodiment, the nucleotides of the first promoter that are required for controllable expression are present and drive expression of a coding sequence that is located downstream of nucleotide 1640. In FIG. 5, a coding region encoding LacZ is present. As described herein, the nucleotides encoding LacZ may be, and preferably are, replaced with nucleotides that encode one or more antimicrobial peptides.

In one embodiment, a pheromone-responsive region includes a nucleotide sequence that is essentially identical to nucleotides 1-1640 of SEQ ID NO:1, or essentially identical to nucleotides 1028-1640 of SEQ ID NO:1. In the context of a polynucleotide "essentially identical" refers to a polynucleotide that differs from one of the polynucleotides disclosed herein. A polynucleotide that is essentially identical to nucleotides 1-1640 of SEQ ID NO:1, or essentially identical to nucleotides 1028-1640 of SEQ ID NO:1, includes an altered nucleotide sequence but retains the characteristics of the pheromone responsive region. Thus, while the nucleotide sequence is different, the nucleotide sequence maintains the bistable switch behavior of a wild type pheromone responsive region. In one embodiment, a pheromone responsive region is essentially identical to a wild type pheromone responsive region if it includes between 1 and 160 differences in the nucleotide sequence.

The pheromone-responsive region includes the prgQ coding region. This encodes iCF10, which includes AITLIFI (SEQ ID NO:49), and negatively regulates the promoter for the prgQ operon. In one embodiment, this coding region is expressed by a pheromone-responsive region in a genetically modified microbe, and in one embodiment this coding region encodes an inactive peptide in a genetically modified microbe. For instance, in one embodiment, the nucleotides at positions 1290-1292 are deleted, which results in deletion of one amino acid in the PrgQ peptide encoded by the prgQ coding region, but does not decrease expression of the operably linked antimicrobial peptide coding regions located downstream of the prgQ coding region. Decreased expression of the prgQ coding region modifies the induction state of the cell that can express the antimicrobial peptides, and results in greater levels of expression of the antimicrobial peptides when a pheromone peptide is present.

An example of the pheromone peptide that abolishes repression of expression by the first promoter of pheromone-responsive region present on a pCF10 conjugative plasmid, for instance, nucleotides 1-1640 of SEQ ID NO:1 or nucleotides 80-1640 of SEQ ID NO:1, is the heptapeptide LVTLVFV (SEQ ID NO:32). This pheromone peptide is naturally expressed by a cell, such as a member of the genus *Enterococcus*, including *E. faecalis* and *E. faecium*, that does not include a pCF10 conjugative plasmid.

With respect to the nucleotides that encode the modulating peptide PrgX (the complement of nucleotides 1027-79), the skilled person will recognize that the nucleotide sequence disclosed in FIG. 5 is not necessary, and that due to codon degeneracy many different nucleotide sequences are possible but still encode a PrgX polypeptide as described by SEQ ID NO:3. A PrgX polypeptide includes those that are essentially identical to SEQ ID NO:3. A PrgX polypeptide that is essentially identical to SEQ ID NO:3 has between 1 and 30 amino acid substitutions, and all integers subsumed within that range. In one embodiment, one or more of the substitutions are conservative substitutions.

Other examples of pheromone-responsive regions present on conjugative plasmids are shown in FIG. 11. In one embodiment, a pheromone-responsive region is from a pPD1 conjugative plasmid, and has the nucleotide sequence SEQ ID NO:5, or essentially identical to SEQ ID NO:5. In this embodiment, nucleotides encoding one or more antimicrobial peptides may be inserted at the 3' end of SEQ ID NO:5. This pheromone-responsive region includes the ipd coding region (the nucleotides double underlined in SEQ ID NO:5). This encodes the analog of iCF10, and negatively regulates the promoter for the ipd operon. In one embodiment, this coding region is expressed by a pheromone-responsive region in a genetically modified microbe, and in one embodiment this coding region encodes an inactive peptide a genetically modified microbe. For instance, in one embodiment, it is expected that nucleotides within the ipd coding region (nucleotides 1188-1211 of SEQ ID NO:5) can be deleted to result in deletion of one amino acid in the portion of the Ipd peptide (ALILTLVS, SEQ ID NO:50) encoded by the ipd coding region, but not decrease expression of the operably linked antimicrobial peptide coding regions located downstream of the ipd coding region. With respect to the nucleotides that encode the modulating peptide TraA (the complement of nucleotides underlined in SEQ ID NO:5), the skilled person will recognize that the nucleotide sequence disclosed in FIG. 5 is not necessary, and that due to codon degeneracy many different nucleotide sequences are possible but still encode a TraA polypeptide. In one embodiment, a TraA polypeptide includes those that are essentially identical to SEQ ID NO:53. A TraA polypeptide that is essentially identical to SEQ ID NO:53 has between 1 and 30 amino acid substitutions, and all integers subsumed within that range. In one embodiment, one or more of the substitutions are conservative substitutions.

In one embodiment, a pheromone-responsive region is from a pAD1 conjugative plasmid, and has the nucleotide sequence SEQ ID NO:6, or essentially identical to SEQ ID NO:6. In this embodiment, nucleotides encoding one or more antimicrobial peptides may be inserted at the 3' end of SEQ ID NO:6. This pheromone-responsive region includes the iad coding region (the nucleotides double underlined in SEQ ID NO:6). This encodes the analog of iCF10, and negatively regulates the promoter for the iad operon. In one embodiment, this coding region is expressed by a pheromone-responsive region in a genetically modified microbe, and in one embodiment this coding region encodes an inactive peptide a genetically modified microbe. For instance, in one embodiment, it is expected that nucleotides within the iad coding region (nucleotides 1194-1217 of SEQ ID NO:6) can be deleted to result in deletion of one amino acid in the portion of the Iad peptide (LFVVTLCG, SEQ ID NO:51) encoded by the iad coding region, but not decrease expression of the operably linked antimicrobial peptide coding regions located downstream of the iad coding region. With respect to the nucleotides that encode the modulating peptide TraA (the complement of nucleotides underlined in SEQ ID NO:6), the skilled person will recognize that the nucleotide sequence disclosed in FIG. 5 is not necessary, and that due to codon degeneracy many different nucleotide sequences are possible but still encode a TraA polypeptide. In one embodiment, a TraA polypeptide includes those that are essentially identical to SEQ ID NO:54. A TraA polypeptide that is essentially identical to SEQ ID NO:54 has between 1 and 30 amino acid substitutions, and all integers subsumed within that range. In one embodiment, one or more of the substitutions are conservative substitutions.

In one embodiment, a pheromone-responsive region is from a pAM373 conjugative plasmid, and has the nucleotide sequence SEQ ID NO:7, or essentially identical to SEQ ID NO:7. In this embodiment, nucleotides encoding one or more antimicrobial peptides may be inserted at the 3' end of SEQ ID NO:7. This pheromone-responsive region includes the 1373 coding region (the nucleotides double underlined in SEQ ID NO:7). This encodes the analog of iCF10, and negatively regulates the promoter for the 1373 operon. In one embodiment, this coding region is expressed by a pheromone-responsive region in a genetically modified microbe, and in one embodiment this coding region encodes an inactive peptide a genetically modified microbe. For instance, in one embodiment, it is expected that nucleotides within the ipd coding region (nucleotides 1226-1246 of SEQ ID NO:7) can be deleted to result in deletion of one amino acid in the portion of the Ipd peptide (SIFTLVA, SEQ ID NO:52) encoded by the ipd coding region, but not decrease expression of the operably linked antimicrobial peptide coding regions located downstream of the ipd coding region. With respect to the nucleotides that encode the modulating peptide TraA (the complement of nucleotides underlined in SEQ ID NO:7), the skilled person will recognize that the nucleotide sequence disclosed in FIG. 5 is not necessary, and that due to codon degeneracy many different nucleotide sequences are possible but still encode a TraA polypeptide. In one embodiment, a TraA polypeptide includes those that are essentially identical to SEQ ID NO:55. A TraA polypeptide that is essentially identical to SEQ ID NO:55 has between 1 and 30 amino acid substitutions, and all integers subsumed within that range. In one embodiment, one or more of the substitutions are conservative substitutions.

Construction of vectors described herein may employ standard ligation techniques known in the art. See, e.g., (Sambrook et al., 1989. Molecular cloning: a laboratory manual, 2nd ed. Cold Spring Harbor Laboratory Press, Cold Spring Harbor, N.Y.). Selection of a vector depends upon a variety of desired characteristics in the resulting construct, such as a selection marker, vector replication rate, and the like. Vectors can be introduced into a host cell using methods that are known and used routinely by the skilled person. The vector may replicate separately from the chromosome present in the microbe, or the polynucleotide may be integrated into a chromosome of the microbe. A vector introduced into a host cell optionally includes one or more marker sequences, which typically encode a molecule that inactivates or otherwise detects or is detected by a compound in the growth medium. For example, the inclusion of a marker sequence may render the transformed cell resistant to an antibiotic, or it may confer compound-specific metabolism on the transformed cell. Examples of a marker sequence include, but are not limited to, sequences that confer resistance to kanamycin, ampicillin, chloramphenicol, tetracycline, streptomycin, neomycin, and erythromycin. Generally, introduction of a vector into a host cell, origin of replication, ribosomal sites, marker sequences, and other aspects of vectors may vary depending on whether the host cell is a gram positive or a gram negative microbe; however, these aspects of vector biology and heterologous gene expression are known to the skilled person.

Also provided herein are genetically modified microbes that include a vector disclosed herein. Compared to a control microbe that is not genetically modified in the same way, a genetically modified microbe will exhibit expression and secretion of an antimicrobial polypeptide in the presence of a modulating agent. In one embodiment, a genetically modified microbe may produce detectable levels of an antimicrobial peptide in the absence of an inducer; however, such levels of an antimicrobial peptide are substantially lower than the levels detectable in the presence of a modulating agent. A vector may be present in the microbe as a vector or integrated into a chromosome. In one embodiment, a portion of the vector is integrated into a microbe chromosome.

Examples of useful bacterial host cells that may be modified to have a vector described herein include, but are not limited to, those that are normally part of the gastrointestinal microflora of an animal. Useful characteristics of a bacterial host cell include, for instance, resistance to bile-acids, generally recognized as safe (GRAS), suited to surviving passage to the gastrointestinal tract, and ability to colonize the gastrointestinal tract. Examples of useful bacterial hosts include, but are not limited to, lactic acid bacteria, including members of the Order Lactobacillales, such as *Lactobacillus* spp., (including, but not limited to, *Lb. acidophilus, Lb. acidophilus, Lb. bulgaricus, Lb. reuteri*, and *Lb. plantarum*), *Lactococcus* spp., (including, but not limited to, *L. lactis*), and *Enterococcus* spp.; members of the family Clostridiaceae, such as *Clostridium* spp.; members of the family Bifidobacteriaceae, such as *Bifidobacterium* spp.; and enterobacteria, such as *E. coli*. In one embodiment, a bacterial host cell is probiotic microbe.

In one embodiment, a genetically modified microbe includes an additional polypeptide that aids entry of the modulating agent (e.g., a pheromone) into a cell, and thereby increases the sensitivity of a genetically modified microbe to a pheromone peptide. Such a polypeptide is referred to as a pheromone binding polypeptide. The polypeptide is a surface receptor that binds the modulating agent (e.g., pheromone), which is then imported into the cell. Such a polypeptide is referred to as a pheromone binding polypeptide. The pheromone binding polypeptide depends upon the type of pheromone-responsive region present in the genetically modified microbe. When the pheromone-responsive region is from a pCF10 conjugative plasmid, the pheromone binding polypeptide is PrgZ, which is encoded by the prgZ coding region on the pCF10 plasmid. An example of a PrgZ polypeptide is shown at SEQ ID NO:4. A PrgZ polypeptide includes those that are essentially identical to SEQ ID NO:4. A PrgZ polypeptide that is essentially identical to SEQ ID NO:4 has between 1 and 30 amino acid substitutions, and all integers subsumed within that range. In one embodiment, one or more of the substitutions are conservative substitutions.

Also provided are methods of using the vectors and genetically modified microbes disclosed herein. In one embodiment, the method includes co-culturing a genetically modified microbe and a second microbe. The co-culturing may be in vitro (in an artificial environment, such as a test tube) or in vivo (within the body of a subject).

The genetically modified microbe may be present in a composition, such as a pharmaceutically acceptable formulation. In one embodiment, a formulation may be a fluid composition. Fluid compositions include, but are not limited to, solutions, suspensions, dispersions, and the like. In one embodiment, a formulation may be a solid composition. Solid compositions include, but are not limited to, powder, granule, compressed tablet, pill, capsule, chewing gum, wafer, and the like. Those formulations may include a pharmaceutically acceptable carrier to render the composition appropriate for administration to a subject. As used herein "pharmaceutically acceptable carrier" includes pharmacologically inactive compounds compatible with pharmaceutical administration. The compositions may be formulated to be compatible with its intended route of administration. A composition may be administered by any method suitable for depositing in the gastrointestinal tract of a subject. Examples of routes of administration include rectal administration (e.g., by suppository, enema, upper endoscopy, upper push enteroscopy, or colonoscopy), intubation through the nose or the mouth (e.g., by nasogastric tube, nasoenteric tube, or nasal jejunal tube), or oral administration (e.g., by a solid such as a pill, tablet, or capsule, or by liquid).

For therapeutic use, a composition may be conveniently administered in a form containing one or more pharmaceutically acceptable carriers. Suitable carriers are well known in the art and vary with the desired form and mode of administration of the composition. For example, they may include diluents or excipients such as fillers, binders, wetting agents, disintegrators, surface-active agents, glidants, lubricants, and the like. Typically, the carrier may be a solid (including powder), liquid, or combinations thereof. Each carrier is preferably "acceptable" in the sense of being compatible with the other ingredients in the composition and not injurious to the subject. The carrier is preferably biologically acceptable and inert, i.e., it permits the composition to maintain viability of the biological material until delivered to the appropriate site.

Oral compositions may include an inert diluent or an edible carrier. For the purpose of oral therapeutic administration, the active compound can be incorporated with excipients and used in the form of tablets, troches, or capsules, e.g., gelatin capsules. Oral compositions can also be prepared by combining a composition of the present invention with a food. In one embodiment a food used for administration is chilled. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

The active compounds can also be prepared in the form of suppositories (e.g., with conventional suppository bases such as cocoa butter and other glycerides) or retention enemas for rectal delivery.

The active compounds may be prepared with carriers that will protect the compound against rapid elimination from the body, such as a controlled release formulation, including implants. Biodegradable, biocompatible polymers can be used, such as ethylene vinyl acetate, polyanhydrides, polyglycolic acid, collagen, polyorthoesters, and polylactic acid. Such formulations can be prepared using standard techniques. The materials can also be obtained commercially from, for instance, Alza Corporation and Nova Pharmaceuticals, Inc. Liposomal suspensions can also be used as pharmaceutically acceptable carriers. These can be prepared according to methods known to those skilled in the art.

In one embodiment, a composition may be encapsulated. For instance, when the composition is to be administered orally, the dosage form is formulated so the composition is not exposed to conditions prevalent in the gastrointestinal tract before the desired site, e.g., high acidity and digestive enzymes present in the stomach and/or upper intestine. The encapsulation of compositions for therapeutic use is routine in the art. Encapsulation may include hard-shelled capsules, which may be used for dry, powdered ingredients soft-shelled capsules. Capsules may be made from aqueous solutions of gelling agents such as animal protein (e.g., gelatin), plant polysaccharides or derivatives like carrageenans and modified forms of starch and cellulose. Other ingredients may be added to a gelling agent solution such as plasticizers (e.g., glycerin and or sorbitol), coloring agents, preservatives, disintegrants, lubricants and surface treatment.

In one embodiment, the method includes administering an effective amount of a genetically modified microbe to a subject in need of such a genetically modified microbe. The subject may be, for instance, a human, or avian (including, for instance, chickens or turkeys), bovine (including, for instance, cattle), caprine (including, for instance, goats), ovine (including, for instance, sheep), porcine (including, for instance, swine), equine (including, for instance, horses), canine (including, for instance, dogs), or feline (including, for instance, cats). The subject may be of any age. A subject in need of genetically modified microbe includes a subject having a gastrointestinal microflora that requires modification. For instance, a subject may have a microbial pathogen, such as a nosocomial pathogen, present in its gastrointestinal tract.

In one embodiment, the method may further include administering to the subject a modulating agent. In one embodiment, such a modulating agent will interact with the modulating polypeptide, e.g., a tet-repressor, and result in expression of the coding sequence encoding the antimicrobial peptide. The modulating agent may be administered to the subject before, with, or after the administration of the genetically modified microbe, or a combination thereof.

In one embodiment, it is not necessary to administer a modulating agent to the subject. When the genetically modified microbe includes a vector that includes a pheromone-responsive region, the modulating agent is produced by the target microbe, and sensed by the genetically modified microbe to result in induction of the first promoter of the pheromone-responsive promoter and the expression of the operably linked coding regions encoding one or more antimicrobial peptides. The target microbe in this embodiment is one that produces the appropriate modulating agent, e.g., the peptide LVTLVFV (SEQ ID NO:32) when the pheromone-responsive region is from a pCF10 plasmid (e.g., nucleotides 1-1640 of SEQ ID NO:1), the peptide ALFSLV-LAG (SEQ ID NO:33) when the pheromone-responsive region is from a pAD1 plasmid (e.g., SEQ ID NO:5), the peptide FLVMFLSG (SEQ ID NO:34) when the pheromone-responsive region is from a pPD1 plasmid (e.g., SEQ ID NO:6), or the peptide AIFILAS (SEQ ID NO:35) when the pheromone-responsive region is from a pAM373 plasmid (e.g., SEQ ID NO:7), such as *E. faecalis* or *E. faecium*.

In one embodiment, a method includes treating a subject having a pathogenic microbe present in its gastrointestinal tract. In another embodiment, the present invention is directed to methods for treating certain conditions in a subject that may be caused by, or associated with, a microbe. Such conditions include, for instance, Gram negative microbial infections and Gram positive microbial infections of the gastrointestinal tract. Examples of conditions that may be caused by the presence of certain microbes in a subject's gastrointestinal tract include, but are not limited to, diarrhea, gastroenteritis, hemolytic-uremic syndrome, inflammatory bowel disease, irritable bowel disease, and Crohn's Disease.

Treating a subject, such as a subject having a pathogenic microbe or a subject having a condition, can be prophylactic or, alternatively, can be initiated after the need for treatment arises. Treatment that is prophylactic, for instance, initiated before a subject manifests symptoms of a condition caused by a pathogenic microbe, such as a member of the genus *Enterococcus*, is referred to herein as treatment of a subject that is "at risk" of developing the condition. Typically, a subject "at risk" of developing a condition is a subject likely to be exposed to a pathogenic microbe, such as a member of the genus *Enterococcus*, causing the condition. For instance, the subject is present in an area where the condition has been diagnosed in at least one other subject (e.g., a hospital in the case of a nosocomial infection). Accordingly, administration of a composition can be performed before, during, or after the occurrence of a condition caused by a pathogenic microbe. Treatment initiated after the development of a condition may result in decreasing the severity of the symptoms of one of the conditions, or completely removing the symptoms. In this aspect of the invention, an "effective amount" is an amount effective to prevent the manifestation of symptoms of a condition, decrease the severity of the symptoms of a condition, and/or completely remove the symptoms. The potency of a composition described herein can be tested according to routine methods (see, for instance, Stanfield et al., Microb Pathog., 3:155-165 (1987), Fox et al., Am. J. Vet. Res., 48:85-90 (1987), Ruiz-Palacios, Infect. Immun., 34:250-255 (1981), and Humphrey et al., J. Infect. Dis., 151:485-493 (1985)). Methods for determining whether a subject a condition caused by a pathogenic microbe and symptoms associated with the conditions are routine and known to the art.

The microbe targeted by the antimicrobial peptide expressed and secreted by a genetically modified microbe may be a Gram negative or a Gram positive microbe. Examples of Gram negative microbes include, but are not limited to, *Salmonella* spp., *E. coli* (including *E. coli* O157: H7, enterotoxigenic *E. coli*, enteroinvasive *E. coli*, and enteropathogenic *E. coli*), *Shigella* spp., *Campylobacter* spp., *Listeria* spp., and *Vibrio* spp. Examples of Gram positive microbes include, but are not limited to, *Staphylococcus* spp. Target microbes may be microbes transmitted to a subject through the ingestion of contaminated food, or by transmission from another subject (for instance, transmission from animal to animal, including animal to human).

The method may further include determining whether at least one symptom associated with a condition cause by a target microbe is reduced, and/or determining whether the shedding of the target microbe by the subject is reduced. Methods for determining whether a subject has a reduction in a symptom associated with a condition are routine and known in the art. Methods for measuring shedding of a microbe are likewise routine and known in the art.

The present invention is illustrated by the following examples. It is to be understood that the particular examples, materials, amounts, and procedures are to be interpreted broadly in accordance with the scope and spirit of the invention as set forth herein.

Example 1

Presented herein are results of tests with recombinant *Lactococcus lactis* that produce and secrete heterologous antimicrobial peptides with activity against Gram-negative pathogenic *Escherichia coli* and *Salmonella*. In an initial screening, the activities of numerous candidate antimicrobial peptides, made by solid state synthesis, were assessed against several indicator pathogenic *E. coli* and *Salmonella* strains. Peptides A3APO and Alyteserin were selected as top performers based on high antimicrobial activity against the pathogens tested and on significantly lower antimicrobial activity against *L. lactis*. Expression cassettes containing the signal peptide of the protein Usp45 fused to the codon optimized sequence of mature A3APO and Alyteserin were cloned under the control of a nisin-inducible promoter nisA and transformed into *L. lactis* IL1403. The resulting recombinant strains were induced to express and secrete both peptides. A3APO- and Alyteserin-containing supernatants from these recombinant *L. lactis* inhibited the growth of pathogenic *E. coli* and *Salmonella* by up to 20-fold, while maintaining the host's viability. This system may serve as a model for the production and delivery of antimicrobial peptides by lactic acid bacteria to target Gram-negative pathogenic bacteria populations.

Methods

Synthetic Peptide Synthesis

The synthetic AMPS used in this study (Table 4) were synthesized by solid-phase methods at the BioMedical Genomics Center at the University of Minnesota (20 mg aliquots at 99% purity).

TABLE 4

Synthetic peptides used in this study.

| Synthetic peptides | Description |
|---|---|
| A3APO (single chain) | RPDKPRPYLPRPRPPRPVR (SEQ ID NO: 36) |
| Alyteserin - 1a | GLKDIFKAGLGSLVKGIA AHVAN (SEQ ID NO: 37) |

Bacterial Strains and Growth Conditions

The bacteria used in this study are listed in Table 5. *L. lactis* IL1403 was cultured at 30° C. in M17 broth (Oxoid Ltd., Basingstoke, UK) supplemented with 0.5% (w/v) glucose (GM17). The *E. coli* and *Salmonella* strains were grown in LB broth (Fisher Scientific, Fair Lawn, N.J., USA) at 37° C., with shaking. Agar plates were made by the addition of 1.5% (wt/vol) agar (Oxoid) to the liquid media. When necessary, erythromycin (Sigma Chemical Co., St.

Louis, Mo., USA) was added to the cultures at 200 μg/ml and 5 μg/ml, for *E. coli* and *L. lactis* respectively.

TABLE 5

Strains used in this study

| Strains | Description |
| --- | --- |
| *E. coli* JM109 (1) | Selection of recombinant plasmids |
| *L. lactis* IL1403 (2) | Plasmid-free strain, non-bacteriocin producer |
| Indicator organisms | |
| *E. coli* BL21(3) | AMP indicator |
| *E. coli* 0157-H7 | |
| 2026 | AMP indicator |
| 2031 | AMP indicator |
| *S. infantis* 129B | AMP indicator |
| *S. typhimurium* 2219B | AMP indicator |

1. Yanisch-Perron et al., 1985, *Gene 33*, 103-19; 2. Chopin et al., 1984, *Plasmid 11*, 260-263; 3. Wood, 1966, *J. Mol. Biol.* 16, 118-33.

Molecular Biology

The amino acid sequences of the peptides Alyteserin and A3APO (Table 4) were used as templates for design of the synthetic genes. The nucleotide sequences for each peptide were then based on the preferred codon usage for expression by *L. lactis*. The nucleotide sequences of the synthetic expression cassettes contained the Usp45 signal peptide nucleotide sequence ($SP_{usp45}$) (Table 6) and a 5'-nucleotide extension containing a NcoI restriction site at the N-terminus. It also included and a 3'-nucleotide extension with the stop codon (TAA) and the XbaI restriction site. All synthetic genes were supplied by GeneArt® (Life Technologies, Paisley, UK).

Molecular cloning techniques were performed according to Sambrook et al (1989, Molecular cloning. Cold spring harbor laboratory press New York) and all DNA restriction enzymes were supplied from New England BioLabs (Beverly, Mass., USA) and used as recommended by the supplier. Ligations were performed with the T4 DNA ligase (New England Biolabs). *E. coli* JM109 competent cells were transformed as described by the supplier, and electrocompetent *L. lactis* cells were transformed with a Gene Pulser XCell™ (Bio-Rad Laboratories, Hercules, Calif., USA) as described previously (Holo and Nes, 1995, *Methods Mol. Biol.* 47:195-199).

Construction of Expression Vectors

The plasmids and synthetic genes used in this study are listed in Table 6. The $SP_{usp45}$: Alyteserin and $SP_{usp45}$: A3APO containing NcoI-XbaI fragments were obtained from the digestion of the Geneart vectors pMK-RQ-Alys and pMK-RQ-A3APO, respectively. These fragments were inserted into plasmid pMSP3545, in frame with the strong inducible Nisin A (PnisA) promoter, obtaining plasmids pMS-Alys and pMS-A3APO, respectively.

TABLE 6

Plasmids and synthetic genes used in this study.

| Plasmids | Description | Reference |
| --- | --- | --- |
| pMK-RQ-A3APO | Kan$^r$, pMK-RQ plasmid carrying $SP_{usp45}$: A3APO | Geneart |
| pMK-RQ-Alys | Kan$^r$, pMK-RQ plasmid carrying $SP_{usp45}$: Alys | Geneart |
| pMSP3545 | Em$^r$; expression vector | 1 |
| pMS-A3APO | Em$^r$; pMSP3545 derivative carrying $SP_{usp45}$: A3APO | This work |
| pMS-Alys | Em$^r$; pMSP3545 derivative carrying $SP_{usp45}$: Alys | This work |
| pMS-A3APO: HIS | Em$^r$; pMSP3545 derivative carrying $SP_{usp45}$: A3APO: HIS | This work |
| pMS-Alys: HIS | Em$^r$; pMSP3545 derivative carrying $SP_{usp45}$: Alys: HIS | This work |
| Synthetic genes | Nucleotide sequence | |
| $SP_{usp45}$: A3APO | <u>ATGGATGAAAAAAAAGATTATCTCAGCTATTTTAATGTCTA CAGTGATACTTTCTGCTGCAGCCCCGTTGTCAGGTGTTTAC GCT</u>CGTCCAGATAAACCACGTCCATATTTACCACGTCCACGTC CACCACGTCCAGTTCGT (SEQ ID NO: 38) | |
| $SP_{usp45}$: Alys | <u>ATGAAAAAAAAGATTATCTCAGCTATTTTAATGTCTACAGT GATACTTTCTGCTGCAGCCCCGTTGTCAGGTGTTTACGCTG</u>GTTTAAAAGATATTTTTAAAGCTGGTTTAGGTTCATTAGTTAAA GGTATTGCTGCTCATGTTGCTAAT (SEQ ID NO: 39) | |

1. Bryan et al., 2000 Plasmid 44: 183-190. The underlined nucleotides encode the Usp45 signal sequence.

Protein Production

Recombinant *L. lactis* were induced to produce both AMPs upon reaching an $OD_{600}$ of 0.5, using nisin A (Sigma) at a final concentration of 25 ng/ml as the inducer. Cell-free culture supernatants were obtained by centrifugation of cultures at 12,000×g at 4° C. for 10 min and filtering through 0.2 µm pore-size filters (Whatman Int. Ltd., Maidstone, UK.). Supernatants were stored at −20° C. until use.

Peptide Transcript Quantification by qPCR

A3APO and Alyteserin production was induced as described above. At 3 hrs post-induction mRNA was isolated using the RNeasy kit and RNAprotect Bacteria Reagent (Qiagen). cDNA libraries were made from each RNA sample using SuperScript II reverse transcriptase (Life Technologies) as directed and qPCR was performed using Brilliant III Ultra-Fast SYBR Green QPCR Master Mix (Agilent Technologies) as directed using the internal ROX dye as a reference. Primers Alys-qPCR-F (CGTTGTCAGGTGTTTACGCTGGTTT) (SEQ ID NO:40) and Alys-qPCR-R (CGTTTAATTAGCAACAT-GAGCAGCAA) (SEQ ID NO:41) were designed to amplify a 95 bp product of Alyteserin gene. Primers A3APO-qPCR-F (TTTTAATGTCTACAGTGA-TACTTTCTGCTGC) (SEQ ID NO:42) and A3APO-qPCR-R (ATACGTTTAACGAACTGGACGTGGTG) (SEQ ID NO:43) were designed to amplify a 122 bp product of A3APO gene. Primers Tuf-qPCR-F (GCGTTCTG-GAGTTGGGATGT) (SEQ ID NO:44) and Tuf-qPCR-R (CCTCTTGAGCGAATACGATT) (SEQ ID NO:45) were designed to amplify a 149 bp product of the elongation factor Tu gene (tuf), which was used as an internal control. Relative transcript increases upon induction were calculated for both AMPs from CT values.

Production and Immunodetection of His-Tagged Proteins.

To confirm the production of recombinant Alyteserin and A3APO by *L. lactis* using immulogical technics, a 6×His-tag sequence was fused to the C-terminus of the cloned genes. Primers SPUsp45-F (ACTCATCATGAAAAAAAAGAT-TATCTCAGC) (SEQ ID NO:46) and A3APO-HIS-R (GATCTAGATTAGTGATGGTGATGGTGATGACCAC-CACGAACTGGACGTGGTGG) (SEQ ID NO:47) were used in a PCR reaction to amplify a BspHI/XbaI 180 bp fragment containing $SP_{usp45}$: A3APO fused to a C-terminal 6×His-tag (fragment $SP_{usp45}$: A3APO:HIS). Primers SPUsp45-F and Alys-HIS-R (GATCTAGATTAGT-GATGGTGATGGTGATGACCACCATTAGCAACAT-GAGCAGC) (SEQ ID NO:48) were used in a PCR reaction to amplify a BspHI/XbaI 192 bp fragment containing $SP_{usp45}$:Alys fused to a C-terminal 6×His-tag (fragment $SP_{usp45}$:Alys:HIS). Fragments $SP_{usp45}$:A3APO:HIS and $SP_{usp45}$: Alys:HIS were digested with the indicated restriction enzymes and inserted into pMSP3545, digested with NcoI and XbaI. The ligation mixtures were used to transform *L. lactis* IL1403 competent cells. The plasmid derivatives pMS-Alys:HIS and pMS-A3APO:HIS, respectively, were checked by PCR and sequencing of the inserts.

*L. lactis* IL1403 (pMSP3545), *L. lactis* IL1403 (pMS-A3APO:HIS) and *L. lactis* IL1403 (pMS-Alys:HIS) strains were grown in 100 ml of GM17 medium and induced with nisin A at an $OD_{600}$ of 0.5 as previously described. At 3 hours after induction the cultures were centrifuged at 12,000×g at 4° C. for 15 min. 50 ml of the supernatants (SN) were stored at −20° C. until use, while the remaining 50 ml were subjected to precipitation with ammonium sulphate (50%) and resuspended in 1 ml phosphate-buffered saline (PBS) (AS-SN). The cell-pellets where washed with PBS and resuspended in 2 ml of ice-cold PBS. Cells were lysed in a Fast-prep apparatus (Biospec) using 0.1 mm glass beads and 6 cycles of 45 s (speed 6.0), with cooling intervals of 45 s on ice. The unbroken cells, cell debris and glass beads were separated from the cell lysate (CL) by centrifugation at 16,100×g at 4° C. for 30 min. 20 µl of SN, AS-SN and CL were spotted into a Amersham Hybond-P PVDF membrane (GE Healthcare) as indicated by the manufacturer. After transfer of the proteins onto the membranes, a dot blots analysis was performed using the Chemiluminescent Western Breeze kit (Invitrogen, Carlsbad, Calif., USA). For detection of Alys:His and A3APO:His, an anti-His (C-term) mouse monoclonal antibody (Invitrogen) was used as recommended by the manufacturer.

Bioassays for Antimicrobial Activity

MICs of the synthetic AMPs were determined in triplicate by a liquid growth inhibition microdilution assays in flat-bottom sterile polypropylene 96-well plates (Maxisorp, Nunc, Roskilde, Denmark), in a final volume of 150 µl. The bacteria were diluted 2% in fresh media and grown to an $OD_{600}=0.5\pm0.05$ ($OD_{600}=1\approx10^9$ cells/ml). The cells were diluted 50-fold to $10^7$ cells/ml in fresh media. The AMP stocks were serially diluted (150 µl/well) in liquid growth media in a 96-well plate, covering a concentration range of 1,000 µg/ml-1 ng/ml. Briefly, 150 µl of the serially diluted AMPs were inoculated with 5 µl of the bacterial strains to achieve a final indicator concentration of $3\times10^5$ cells/ml. For each strain a row with no peptide was included as growth control, and for each test a row of medium-only wells was included as a sterility control. Plates were then incubated at 37° C. for 16-20 h without shaking, and growth inhibition was assessed measuring $OD_{600}$ using a microplate reader (SpectraMax® Plus384; Molecular Devices, Sunnyvale, Calif., USA). MICs were identified as the lowest antimicrobial concentration where the $OD_{600}$ just exceed that of the control.

The loss of cell viability was monitored to determine the antimicrobial activity of the supernatants from the recombinant *L. lactis* strains. Briefly, 0.3 ml of fresh medium, individually inoculated with the target strains, was added to tubes containing 0.7 ml of the supernatants, to reach a final concentration of $1\times10^3$ cells/ml. As a control, a supernatant sample from the *L. lactis* strain containing only the expression vector pMSP3545 (C-SN) was used. Tubes were incubated at 37° C. with agitation. Samples were taken at 30 min, 2 and 6 h, and the number of colony forming units per ml (CFU/ml) was determined by plating 25 µl on LB agar plates. The plates were incubated for 16 h at 37° C., and the number of viable cells was assessed by counting CFUs. Additionally, the $OD_{600}$ was monitored up to 15 h post-inoculation to follow the influence of AMPs on culture growth.

Results and Discussion

Motivated by the current state of antibiotic overuse and the rapid emergence of bacterial strains with resistance to antibiotics molecules, the overall goal of this work was to engineer a LAB strain to inducibly express and secrete AMPs with high activity against important Gram-negative pathogens. In summary, this was achieved by first screening AMPs for high activity against pathogenic *E. coli* and *Salmonella* strains and low activity against LAB. Genes encoding peptides that displayed the most favorable activity were then included in expression cassettes for use in *L. lactis*. In the following, we detail how we 1) selected the AMPs of interest, 2) engineered *L. lactis* to express the heterologous peptides and 3) tested the recombinant expression systems. To our knowledge this is one of the first works in which LAB have been engineered to express and secrete AMPs that are specifically active against Gram-negative pathogens.

Screening of AMPs with Activity Against Gram-Negative Bacteria

Recently discovered AMPs that have been introduced into clinical practice largely display activity against Gram-positive organisms while being ineffective against Gram-negative bacteria (Gruenheid and Moual, 2012, FEMS Microbiol. Lett. 330:81-89). This is due in part to the unique cell wall and membrane structure of these two classes of bacteria (Papagianni et al., 2009, Microb. Cell Fact. 8:3; Bassetti et al., 2011, Crit. Care/5:215). However there are a few exceptional AMPs that show high specific activity against Gram-negative bacteria (Hoffmann et al., 1999, Biochim. Biophys. Acta 1426:459-467; Cassone et al., 2008, Peptides 29:1878-1886). To select top candidate AMPs to use in our study, we initially searched the literature for functional peptides fulfilling the following requirements: 1) lack of post-translational modifications and disulfide bonds, 2) activity against Gram-negative bacteria at low concentrations (≤500 µg/ml) and 3) no or significantly less activity against Gram-positive bacteria, in particular against the L. lactis host LAB. From this first screen, numerous candidates were chosen and chemically synthesized as described in Methods. The minimum inhibitory concentration (MIC) of the synthetic peptides was evaluated against a panel of pathogenic strains of E. coli and Salmonella and against L. lactis.

Two peptides, Alyteserin-la (Alyteserin) and A3APO, emerged as promising candidate AMPs. Alyteserin was previously identified in the secretions on frog skin while A3APO was discovered in a synthetic peptide library screen (Szabo et al., 2010, Int. J. Antimicrob. Agents 35:357-361; Conlon et al., 2009, Peptides 30:1069-1073). The MIC of pure Alyteserin was 500 µg/ml against indicator E. coli and Salmonella strains. Additionally, L. lactis remained viable despite treatment with up to 1 mg/ml Alyteserin (FIG. 1a). Inhibition of E. coli by A3APO was observed only at a concentration of 1 mg/ml. However, Salmonella growth was inhibited by 30 µg/ml Alyteserin, reducing viability through the highest concentration tested (1 mg/ml). Similarly, L. lactis growth was not inhibited with the different A3APO concentrations tested (FIG. 1b).

The two AMPs chosen in this study did not require post-translational modifications for activity. The heterologous production of proteins that require post-translational modifications to be active can be problematic when using LAB as hosts. There are several examples where recombinant peptides that required post-translational modifications were being produced at high concentrations but had low specific activity (Borrero et al., 2011, 1 Biotechnol. 156:76-86). This has been attributed to a variety of causes, such as non-efficient disulfide bond formation, problems in protein folding, and protein aggregation (Borrero et al., 2011, Appl. Microbiol. Biotechnol. 89:131-143).

Once the two candidate peptides were identified, L. lactis was engineered to express Alyteserin and A3APO. Details of this process are presented in the Materials and Methods. The resulting L. lactis were cultured to express and secrete the peptides. The cell-free supernatants containing these AMPs were isolated and their effect on E. coli and Salmonella growth and viability were assessed as also described in the Materials and Methods.

Construction of Recombinant L. lactis Strains for AMP Production

Lactococcus lactis strain IL1403 was engineered to express the AMPs Alyteserin and A3APO as detailed in the Materials and Methods. Briefly, the codon-optimized nucleotide sequences of both peptides were synthesized by GeneArt and fused to the Usp45 secretion signal peptide sequence ($SP_{usp45}$) (Van Asseldonk et al., 1990, Gene 95:155-160). The expression cassettes were cloned downstream of the nisin inducible promoter, PnisA, from plasmid pMSP3545 (Bryan et al., 2000, Plasmid 44:183-190) resulting in recombinant vectors pMS-Alys and pMS-A3APO, respectively. L. lactis IL1403 was transformed with both recombinant vectors, and the resulting L. lactis (pMS-A3APO) and L. lactis (pMS-Alys) strains, as well as the control L. lactis strain (L. lactis containing the empty pMSP3545 vector), were cultured to express and secrete each AMP. The AMP-containing supernatants (AMP-SNs: Alys-SN, A3APO-SN and C-SN for supernatants containing AMPs Alyteserin, A3APO and the control supernatant lacking AMPs, respectively) were collected as described in Methods.

Growth of pathogenic and non-pathogenic E. coli strains was assessed in medium containing these AMP-SNs while only pathogenic Salmonella strains were tested. In all cases, AMP-SNs diluted 7:3 with LB were inoculated with each indicator strain and growth was monitored spectrophotometrically at 600 nm for 15 hr.

Peptide Production and Secretion

QPCR was performed to determine the transcript levels of Alysteserin and A3APO genes upon induction. A3APO transcript increased by over 100-fold upon induction while Alyteserin mRNA increased by 30-fold. To confirm the production of recombinant Alyteserin and A3APO by L. lactis, a His-tag sequence was fused to the C-terminus of both genes. The induced cultures were centrifuged and 2 fractions were collected: the cell pellet and the cell-free supernatant. The cell-pellet was lysed, as described in Methods, obtaining a cell lysate. The cell-free supernatants were treated with ammonium sulfate to 50% saturation to precipitate and concentrate the proteins. The crude supernatants, the ammonium sulfate and the cell-lysate fractions were subjected to dot blotting and immunological detection using Anti-His (C-terminal) antibodies. No signal was detected in any of the fractions obtained from the L. lactis control strain. A signal was detected in the crude supernatant samples from the AMP producing L. lactis and cell-lysate fractions. Increased signal was detected upon concentration with ammonium sulfate and in the cell-lysate fractions. Although this confirms the presence of AMPs in the supernatants, it illustrates that a significant amount of peptide still remains inside the cells. Similar observations have also been made with other recombinant peptides fused to the Usp45 signal peptide (Rodriguez-Rubio et al., 2012, Appl. Environ. Microbiol. 78:3469-3472). The protein size and the particular combination of signal peptide and mature protein are factors that may be limiting the secretion of the peptides.

E. coli Growth Inhibition by Alyteserin Produced by L. lactis

As shown in FIG. 2, Alys-SN inhibited growth of E. coli strains. Culture titer was assessed starting at 30 min post-inoculation and culture density was monitored by $OD_{600}$ 10-15 h post-inoculation. Prior to the 6 h time point, E. coli cultures treated with Alys-SN and C-SN were not statistically different. However, different culture concentrations were observed beginning 6 h post-inoculation (FIG. 2a), and this differential growth pattern was maintained through 15 h (FIG. 2b). Upon treatment with Alys-SN, culture concentrations were reduced by over 20-fold relative to those treated with C-SN at 6 h post-inoculation and maintained a density at or less than this value through the 15 h incubation period. The same trends were found with all *E. coli* strains tested. Growth rates for *E. coli*, as shown in Table 7, were calculated based on culture densities 10-15 h post inoculation. There was no significant *E. coli* growth when treated with Alys-SN during this time and the cultures never achieved exponential growth. Thus, Alys-SN effectively inhibited *E. coli* growth during the 15 h culture period.

TABLE 7

Growth rates and relative culture growth of *E. coli* and *Salmonella* with AMP treatment.

| | E. coli | Salmonella |
|---|---|---|
| | Growth rate (hr$^{-1}$) | |
| C-SN | 0.73 | 0.66 |
| Alys-SN | ≈0 | 0.57 |
| A3APO-SN | >0.8 | 0.7 |
| | Relative Growth rate (%) | |
| C-SN | 100 | 100 |
| Alys-SN | ≈0 | 86 |
| A3APO-SN | >100 | >100 |

In contrast, there was no change in *E. coli* culture concentration when strains were cultured with A3APO-SN. The MIC value for synthetic A3APO against *E. coli* strains was 1 mg/ml (FIG. 1) and it is reasonable that the concentration of active peptide is lower than this in tested supernatant samples.

*Salmonella* Growth Inhibition by Alyteserin-La and A3APO Produced by *L. lactis*

Alys-SN and A3APO-SN inhibited growth of pathogenic *S. typhimurium* and *S. infantis* as shown in FIG. 3a. As before, the culture titer was assessed beginning 30 min post-inoculation and culture density was monitored by $OD_{600}$ from 10 to 15 h. By 2 h post-inoculation, a differential titer between cultures treated with Alys-SN and A3APO-SN was observed (FIG. 3a). Relative to culture growth with C-SN treatment, growth of *S. infantis* treated with Alys-SN was reduced by about one-half while *S. typhimurium* was reduced by 10-fold. Moreover, A3APO-SN reduced the culture density of *S. infantis* by over 20-fold relative to C-SN while *S. typhimurium* culture density was reduced by 4-fold. The inhibition of *Salmonella* by Alys-SN was maintained through 15 h, while culture density with A3APO-SN was the same as C-SN by 10 h post-inoculation (FIG. 3b). At 15 h post inoculation, the Alys-SN maintained *Salmonella* culture densities at only 25% relative to the same strains treated with the C-SN. These trends were consistent across both the *S. infantis* and *S. typhimurium* strains tested.

The strong activity shown by A3APO-SN against *Salmonella* is consistent with the significantly lower MIC value observed (30 µg/ml) for synthetic A3APO peptide against *Salmonella*.

As shown in Table 7, growth rates for *Salmonella* were calculated based on culture densities 10 to 15 h post inoculation. In contrast to what was observed with *E. coli*, there was significant *Salmonella* growth in the presence of Alys-SN and the cultures achieved exponential growth. However, growth rates were reduced by 15% relative to cultures grown in C-SN during this time. Additionally, although the densities of the *Salmonella* cultures grown in A3APO-SN were significantly reduced at earlier time points, relative to C-SN, no differences were observed by 10 h after inoculation.

Improving Active Peptide Production

Currently, the factors that most significantly improve the antimicrobial activity of Alyteserin and A3APO produced by recombinant *L. lactis* are difficult to determine. We postulate that the use of $SP_{usp45}$ to produce and secrete these peptides is likely to be one such factor as there are significant context dependencies between a secretion peptide and the molecule for which they are driving secretion (Ng et al., 2013, *Appl. Environ. Microbiol.* 79:347-356). Peptide translation, targeting the Sec-dependent protein to the membrane, the translocation process itself, and the peptide's subsequent processing by a signal peptidase likely represent the major bottlenecks for efficient translocation, and thus production of heterologous proteins (Degering et al., 2010, *Appl. Environ. Microbiol.* 76:6370-6376). Since there are no good prediction methods for determining the right combination of secretion peptide and target protein to achieve a high protein production system (Borrero et al., 2011, *J. Biotechnol.* 156:76-86; Brockmeier et al., 2006, *J. Mol. Biol.* 362:393-402), screening for a more efficient secretion peptide and protein combinations for overproduction and secretion may still further improve active peptide secretion (Degering et al., 2010, *Appl. Environ. Microbiol.* 76:6370-6376; Stammen et al., 2010, *Appl. Environ. Microbiol.* 76:4037-4046). Several strategies have been used in this direction. Using different signal petides (Borrero et al., 2011, *J. Biotechnol.* 156:76-86), modifying the amino acids of the N-terminus of the signal peptide (Ng and Sarkar, 2013, *Appl. Environ. Microbiol.* 79:347-356) or adding a propeptide between the signal peptide and the mature protein may help increase peptide secretion (Le et al., 2001, *Appl. Environ. Microbiol.* 67:4119-4127). Further experiments must be performed in order to maximize the secretion of AMPs and further increase the antimicrobial activity of the supernatants. Improper protein folding may also account for compromised antagonistic activity. Thus, the use of chaperones, increasing specific peptide activity through rounds of mutagenesis, and increasing peptide gene copy number are approaches currently being pursued to improve these expression systems (Drouault et al., 2002, *Appl. Environ. Microbiol.* 68:3932-3942).

Summary

In this study we report that *L. lactis* can be used to produce and secrete the antimicrobial peptides Alyteserin-la and A3APO, with sufficient activity to inhibit pathogenic *E. coli* and *Salmonella* strains, while maintaining the host's viability. Previous studies have reported the production and secretion of AMPs by recombinant *L. lactis* (Borrero et al., 2011, *J. Biotechnol.* 156:76-86; Borrero et al., 2011, *Appl. Microbiol. Biotechnol.* 89:131-143; Munoz et al., 2011, *Recent Pat. Biotechnol.* 5:199-211). However, these peptides have frequently displayed antimicrobial activity against Gram-positive bacteria but either no or poor activity against Gram-negative indicators (McCormick et al., 1999, *Lett. Appl. Microbiol.* 29:37-41; Acuria et al., 2011, *Food Bioprocess Tech.* 4:1029-1049). While the activity of A3APO and Alyteserin in the supernatants of recombinant *L. lactis* is still not at the level of many small molecule antibiotics, to our knowledge this is the first time that a synthetic or animal-origin AMP has been produced by *L. lactis* with activity against Gram-negative bacteria pathogens. This opens up possibilities for the design of new synthetic peptides and the engineering of known AMPs to improve their antimicrobial activity and spectrum of action.

Lactic acid bacteria are bile-resistant, generally considered safe to consume organisms that may take hold in the gastrointestinal tract of animal or human hosts. As such, they can be considered as promising delivery vehicles for AMPs to the site of gastrointestinal infections. By making and delivering peptides to the site of *E. coli* or *Salmonella* infections, AMP-producing organisms may circumvent previous limitations of the short half-lives that are characteristic of AMPs and the high production and purification costs also associated with peptides (Marr et al., 2006, *Curr. Opin. Pharmacol.* 6:468-472; Nilsson et al., 2005, *Annu. Rev. Biophys. Biomol. Struct.* 34:91-118; Gräslund et al., 2008, *Nat. Methods* 5:135-146).

Example 2

Methods
Gene Design.

Based on the AMPs nucleotide sequences obtained from NCBI we designed two different genetic fragments (ANEX 1): a synthetic polycistronic operon containing the enterocin A structural (entA) and immunity gene (entiA) (GenBank: AF240561.1), the hiracin JM79 structural (hiriJM79) and immunity gene (hirJM79) (GenBank: DQ664500.1), and the enterocin P structural (entP) and immunity gene (entiP) (GenBank: AF005726.1); and the gene from endolysin Lys170 (lys170) (Proenca et al., 2012, *Microb Drug Resist.* 18: 322-332). In bacteria, most proteins are secreted via the general secretory pathway or Sec system, being synthesized as precursors containing the mature protein and N-terminal signal peptides (SP) (Borrero et al., 2011, *J Biotechnol.* 156:76-86). Both EntP and HirJM79 are produced with a signal peptide, but EntA is naturally produced with a leader sequence (LSEntA) and needs a dedicated ABC transporter system in order to be secreted. It has been shown that the substitution of LSEntA by the signal peptide from protein Usp45 ($SP_{usp45}$) is enough to secrete active EntA through the Sec system by *L. lactis* (Borrero et al., 2011, *J Biotechnol.* 156:76-86). Therefore both entA and lys170 were fused to $SP_{usp45}$. All the sequences were synthesized by Geneart (Invitrogen).

Construction of the Recombinant Vectors

All plasmids, PCR fragments and primers used in this study are summarized in Table 8. All fragments were digested with the indicated restriction enzymes and inserted into vector pBK2idTZ. The ligation mixtures were used to transform *E. coli* DH5a competent cells. The presence of the correct recombinant plasmids was checked by PCR and sequencing of the inserts. The recombinant vectors were then isolated from *E. coli* and used to transform *L. lactis* NZ9000 competent cells.

TABLE 8

| Plasmids | Description | Source |
| --- | --- | --- |
| pBK2 | $Cm^r$; inducible expression vector carrying the prgX/prgQ system | UMN |
| pBK2idT | $Cm^r$; inducible expression vector carrying the prgX/prgQ system with a 3 nucleotide deletion in prgQ | UMN |
| pBK1 | Cnnr; constitutive expression vector carrying the prgX/prgQ system with a deletion of the entire prgX gene | UMN |
| pBK2Z | pBK2 carrying prgZ under the control of the constitutive promoter P23 | This work |
| pBK2idTZ | pBK2idT carrying prgZ under the control of the constitutive promoter P23 | This work |
| pBK2idtZ:Bac | pBK2idT derivative carrying fragment Bac | This work |
| pBK2idTZ:EntA | pBK2idT derivative carrying fragment EntA | This work |
| pBK2idTZ:HirJM79 | pBK2idT derivative carrying fragment HirJM79 | This work |
| pBK2idTZ:EntP | pBK2idT derivative carrying fragment EntP | This work |
| pBK2idTZ:Lys170 | pBK2idT derivative carrying fragment Lys170 | This work |

| Fragments | Description |
| --- | --- |
| Bac | 1,628-bp BamHI-EcoRI fragment containing the enterocin A structural gene (entA) with its immunity gene (entiA), the enterocin P structural gene (entP) with its immunity gene (entiP) and the hiracin JM79 structural gene (hirJM79) with its immunity gene (hiriJM79) |
| EntA | 538-bp BamHI-EcoRI fragment containing entA + entiA |
| HirJM79 | 546-bp BamHI-EcoRI fragment containing hirJM79 + hiriJM79 |
| EntP | 504-bp BamHI-EcoRI fragment containing entP + entiP |
| Lys170 | 538-bp BamHI-EcoRI fragment containing the endolysin 170 structural gene (Lys170) |

| Primers | Amplification of fragment |
| --- | --- |
| prg:usp45-F | Bac, EntA and Lys170 |
| EntiA-R | EntA |
| prg:HirJM79-F | HirJM79 |
| HiriJM79-R | Bac and HirJM79 |
| prg:EntP-F | EntP |
| EntiP-R | EntP |
| Lys170-R | Lys170 |

Indicator Strains

The project has the aim of targeting pathogenic enterococci. *Enterococcus faecalis* are ubiquitous members of the mammalian gastrointestinal flora, a leading cause of nosocomial infections and a growing public health concern. The enterococci responsible for these infections are often resistant to multiple antibiotics and have become notorious for their ability to acquire and disseminate antibiotic resistances. In the current study we have selected several *E. faecalis* from different origins as indicator strains. These strains are listed in Table 9.

TABLE 9

| | Source | Description |
|---|---|---|
| *E. faecalis* (1) | | |
| V583 | Blood | ATCC700802; St. Louis, MO, U.S.; First isolated Vancomycin-resistant and first sequenced *E. faecalis* genome |
| Pan7 | Commensal | Panose 7; fecal sample of healthy volunteer; Boston, MA, U.S. |
| Com1 | Commensal | Fecal sample of healthy volunteer; Boston, MA, U.S. |
| CH116 | Fecal | Boston, MA; U.S.; Gent/Kan/Strep/Tet/Erm/Pen resistant, b2lactamase-producing isolate; from L.B. Rice |
| OG1RF | Oral | ATCC 47077; plasmid-free, Rif/Fus resistant mutant of OG1; common laboratory strain |
| JRC105 (2) | UMN | OG1RF Δ(gelE-sprE)10 |
| JH2-2 | Clinical | U.K.; Rif/Fus resistant mutant; common laboratory strain |
| *E. faecium* | | |
| isolate 6 | Urine | UMN isolate, Amp/Vanc/Linezolid resistant |
| isolate 7a | Cerebrospinal fluid (CSF) | UMN isolate, Amp/Vanc/Linezolid resistant |
| isolate 8 | Urine | UMN isolate, Amp/Vanc/Linezolid resistant |
| isolate 9b | Blood | UMN isolate, Amp/Vanc/Linezolid resistant |

1. McBride et al., 2007, PLoS One. 2. e582; 2. Kristich et al., 2007, Plasmid. 57:131-44.

Expression System

Herein, we prepare and use a set of novel vectors based on the peptide pheromone-inducible conjugation system of *E. faecalis* plasmids pCF10.

The antibiotic resistance plasmid pCF10 of *E. faecalis* is a member of a family of mobile genetic elements whose ability to transfer from a donor to a recipient bacterial cell is controlled by intercellular signalling via a peptide mating pheromone. Donor cells carrying pCF10 are induced to high expression of conjugative transfer and virulence genes by a heptapeptide (LVTLVFV)-mating pheromone cCF10 (also referred to as C, SEQ ID NO:32). Donor cells import C into the cytoplasm, where its binding to the pCF10-encoded master regulator Prg X [the protein product of pheromone responsive gene X (prgX)] abolishes repression of transcription of the prgQ operon encoding the conjugation genes. The mating response of donor cells to C is encoded by pCF10, whereas C is produced from a conserved chromosomal gene present in most if not all *E. faecalis* strains (Chatterjee et al., 2013, *Proc Natl Acad Sci USA*. 110: 7086-90). The donor cells produce reduced but still significant levels of cCF10 in both cell wall fractions and supernatants (Buttaro et al., 2000, *J Bacteriol*. 182: 4926-33). This residual pheromone activity is neutralized by the production of the peptide iCF10 from the prgQ locus of pCF10, which negatively regulates the promoter for the prgQ operon. Therefore the molar ratio of chromosomally encoded pheromone (cCF10) to plasmid-encoded inhibitor (iCF10) determines the induction state of the donor cell (Nakayama et al., 1994, *J Bacteriol*. 176: 7405-8).

Figure 4:
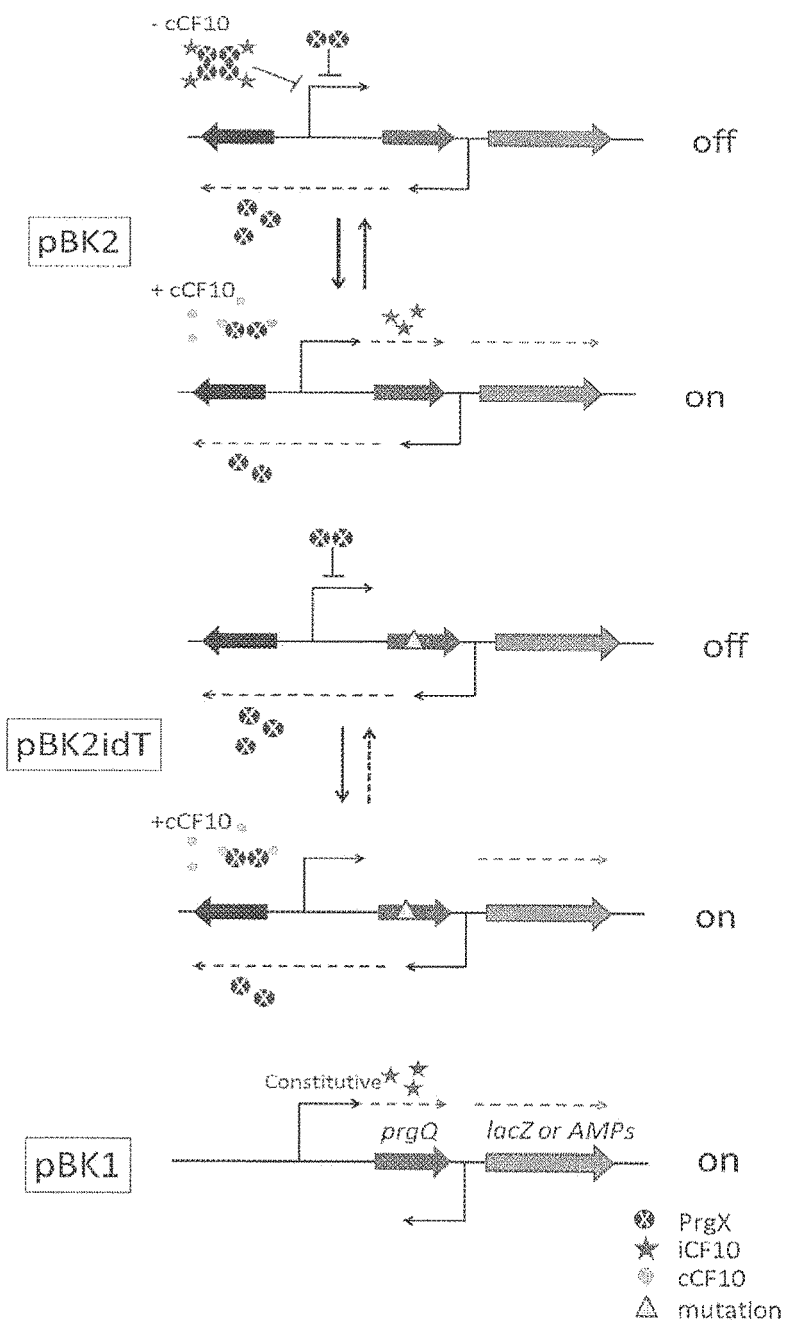
FIG. 4. Regulatory architectures cloned in lactic acid bacteria. pBK1 is a constitutive promoter. pBK2 maintains the prgX/prgQ region intact. pBK2iDT does not express inhibitor iCF10. Switching on is then possible at smaller concentrations of cCF10, making this a more sensitive promoter to the presence of EF.

Based on the prgX/prgQ system, we developed a set of shuttle vectors able to replicate in *E. coli* and in Gram-positive bacteria. These new vectors contain the prgX/prgQ promoter region controlling the expression of both prgX and prgQ, respectively, in the same conformation as in pCF10. These vectors have been complemented with an *E. coli* and a gram-positive replication origin and a chloramphenicol resistance marker. Downstream of prgQ there is a multi-cloning site for the expression of the gene of interest under control of prgX/prgQ. As a start point the gene encoding the protein beta-galactosidase (lacZ) has been selected as reporter gene. Three different vectors have been constructed (FIG. 4 and FIG. 5):

pBK2: this vector maintains the prgX/prgQ region intact, so in normal conditions the expression of prgQ and lacZ is off. On the other hand, the addition of the mating-pheromone cCF10 to the media abolishes repression of the transcription of both prgQ and lacZ. The expression of both genes remains "on" until the levels of iCF10 (the peptide derived from PrgQ) are high enough to overcome the induction by cCF10 and turn back off the promoter.

pBK2idT: this vector presents a 3 amino acid deletion in prgQ that negatively affects the inhibitor activity of iCF10. It works the same way as pBK2 with the difference that upon induction with cCF10 the expression of prgQ and lacZ is on, and remains this way until the levels of cCF10 in the media are low enough to continue abolishing the repression of the expression of both genes.

pBK1: this vector has a deletion of the entire prgX gene. This deletion affects the repression of the prgQ promoter ($P_Q$) by PrgX. Therefore it works as a constitutive promoter where both PrgQ and downstream genes are constitutively produced.

In a first approach, these vectors were used to transform competent cells of the strain *L. lactis* NZ9000. Using a β-galactosidase assay we were able to detect the expression of lacZ when the mating pheromone cCF10 was added to media. In order to quantify the leakiness of prgX/prgQ, the β-Galactosidase activity was measured spectrophotometrically in cell lysates, following cleavage of ONPG. No β-Gal activity was detected in the absence of cCF10, obtaining values similar to those observed with the wildtype strain (*L. lactis* without plasmid). On the other hand when the cultures were induced with cCF10, we were able to detect the expression of lacZ. These results confirm the tight regulation of prgX/prgQ.

One of the goals of this work is engineering LAB able to detect the presence of enterococci in the unpredictable and dynamic environment of the GI tract. Although the regulation of the gene encoding cCR10 has not been well characterized, it seems like most if not all enterococci include the chromosomal gene encoding for cCF10. In an initial approach we tested whether the presence of enterococci producing cCF10 was enough to activate the expression of prgX/prgQ in our recombinant *L. lactis* strains. We streaked 2 different *E. faecalis* strains in plates supplemented with X-Gal and put them in contact with *L. lactis*-pBK1, *L. lactis*-pBK2 and *L. lactis*-pBK2idT. Moreover, in a similar assay, we tested 8 different *E. faecalis* strains in contact with the recombinant *L. lactis* using a drop of the cultures. The recombinant *L. lactis*-pBK2 and *L. lactis*-pBK2idT were able to express lacZ when in close contact with the enterococci strains. This confirms that cCF10 is constitutively produced by the enterococci tested, and that the levels of cCF10 are enough to activate the expression of lacZ from the prgX/prgQ system in *L. lactis*. The activity observed when cCF10 was added directly to the media was much higher, suggesting that the basal production of cCF10 by *E. faecalis* is much lower than the 50 mg/ml used to induce the promoters.

Although these results were quite promising, the expression of lacZ was observed only in those colonies that directly interact with enterococci. This may indicate that cCF10 is associated with the cell wall of the enterococci, or that the concentration of cCF10 is only high enough to induce prgX/prgQ in the close proximity of these strains. Therefore we studied new mechanisms to improve the sensitivity of prgX/prgQ to cCF10. The first approach taken in this direction was the expression of prgZ in the recombinant vectors.

Figure 7:
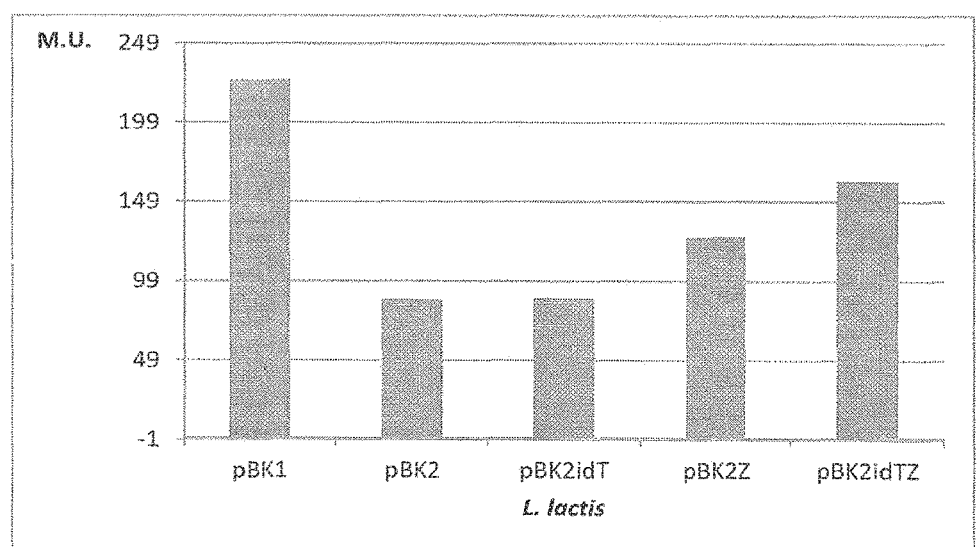

Recently PrgZ, a component of the prgQ operon, has been characterized. PrgZ is an anchored extra-cellular peptide-binding protein playing an important role in the transport of cCF10 inside the enterococcal cells (Dunny, 2007, Philos Trans R Soc Lond B Biol Sci. 362:1185-93). Our hypothesis was that the presence of PrgZ in the membrane of the recombinant LAB may increase the transport of cCF10 inside the cell, and therefore a lower concentration of cCF10 may be required to induce prgX/prgQ. A set of vectors have been constructed that incorporate the prgZ gene under the control of a strong constitutive promoter (P23) (van der Vossen et al., 1987, Appl. Environ. Microbiol., 53:2451-2457). This fragment has been incorporated in plasmids pBK2 and pBK2idT (pBK2Z and pBK2idTZ, respectively). pBK2Z and pBK2idTZ were constructed by inserting the prgZ coding region and P23 promoter into pBK2 and pBK2idT at the PstI restriction site in the antisense strand (in the same direction as prgX). The prgZ coding region and P23 promoter are shown in FIG. 6. As observed in FIG. 7 under the same amount of cCF10 (50 ng/ml), the expression of lacZ was 18% and 32% higher in *L. lactis*-pBK2Z and *L. lactis* pBK2idTZ respectively, in comparison with the same plasmids lacking prgZ.

Antimicrobial Activity

The antimicrobial activity of individual *L. lactis* NZ9000 pBK2idTZ:Bac, *L. lactis* NZ9000 pBK2idTZ:EntA, *L. lactis* NZ9000 pBK2idTZ:HirJM79, *L. lactis* NZ9000 pBK2idTZ:EntP, *L. lactis* NZ9000 pBK2idTZ:Lys170 colonies was examined by the stab-on-agar test (SOAT). Briefly, individual colonies were stabbed onto M17 plates supplemented with glucose (GM17) and the inducer cCF10 (100 ng/ml), incubated at 32° C. for 5 h, and then 40 ml of the corresponding soft agar (0.8%, w/v) medium containing about $1 \times 10^5$ CFU/ml of the indicator strain was poured over the plates. After incubation at 37° C. for 16 h, the plates were checked for inhibition zones (absence of visible microbial growth around the stabbed cultures).

The strains *L. lactis* NZ9000 pBK2idTZ:Bac, *L. lactis* NZ9000 pBK2idTZ:EntA, *L. lactis* NZ9000 pBK2idTZ:HirJM79, *L. lactis* NZ9000 pBK2idTZ:EntP produced and secreted biologically active bacteriocins with activity against the indicator strain *E. faecalis* JH2-2. The strain *L. lactis* NZ9000 pBK2idTZ:Lys170 did not exhibit antimicrobial activity against the same indicator. The production of the three bacteriocins by the same strain (*L. lactis* NZ9000 pBK2idTZ:Bac) improved the inhibitory activity with respect those strains producing individual bacteriocins. This is probably due to a synergistic effect of the three bacteriocins together. Moreover, the production of the three bacteriocins by *L. lactis* NZ9000 pBK2idTZ:Bac was enough to inhibit the growth of all the different *E. faecalis* strains tested, *E. faecalis* V-583, *E. faecalis* JH2-2, *E. faecalis* Pan7, *E. faecalis* ComI, and *E. faecalis* CH116.

In a different set of experiments, *L. lactis* NZ9000 pBK2idtZ:Bac, *E. faecalis* JH2-2 and *E. faecalis* OG1RF pBK1 were grown in GM17 and BHI broth overnight at 32° C. and 37° C., respectively. The three cultures were inoculated (4%) in fresh media and grown 5 h, then 5 μl of the *L. lactis* NZ9000 pBK2idtZ:Bac culture and 10 μl of the *E. faecalis* JH2-2 culture were spotted onto GM17 plates supplemented with cCF10 (100 ng/ml) (GM17+cCF10) and onto GM17 plates. On the other hand, 10 μl of the *L. lactis* NZ9000 pBK2idtZ:Bac culture and 5 μl of the *E. faecalis* OG1RF pBK1 culture were spotted onto GM17 plates supplemented with X-gal. After incubation at 37° C. for 16 h, the plates were checked for inhibition zones. We observed that the presence of the cCF10-producing enterococal strains is enough to induce the expression of bacteriocins by recombinant *L. lactis* and inhibit the growth of both enterococci. In particular, we observe zones of inhibition inside *enterococcus* spots. We also observe the absence of blue colonies inside the *L. lactis* spot.

Discussion

From these results we can conclude that the construction of vectors using the prgX/prgQ system from plasmid pCF10 can be used for the expression and production of peptides of interest by *L. lactis*. Moreover, the cloning of the structural genes of the bacteriocins enterocin A (entA), enterocin P (entP) and hiracinJM79 (hirJM79), with their respective immunity genes into prgX/prgQ-based expression vectors permits the production of biologically active EntA, EntP and HirJM79 by *L. lactis*. The strain *L. lactis* NZ9000 pBK2idTZ:Bac is able to produce the bacteriocins EntA, EntP and HirJM79 with a synergistic activity against different *E. faecalis* strains. Finally, the presence of enterococcal strains in the close proximity is enough to trigger the expression and production of antimicrobial peptides by *L. lactis* using the prgX/prgQ-based vectors.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. Supplementary materials referenced in publications (such as supplementary tables, supplementary figures, supplementary materials and methods, and/or supplementary experimental data) are likewise incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

What is claimed is:

1. A system comprising: (a) a genetically modified microbe, wherein the genetically modified microbe is a lactic acid bacteria, a member of a family Clostridiaceae, member of a family Bifidobacteriaceae, or an Enterobacteria; (b) a first polynucleotide comprising a coding region operably linked to a first promoter, wherein expression of the coding region by the first promoter is inhibited by a modulator polypeptide bound to the first promoter and preventing expression of the operably linked coding region and activated by a modulating agent, and wherein the coding region encodes an antimicrobial peptide; and (c) a second polynucleotide comprising a second coding region operably linked to a second promoter, wherein the second coding region encodes the modulator polypeptide.

2. The system of claim 1 wherein the lactic acid bacterium is a *Lactococcus* spp.

3. The system of claim 2 wherein the *Lactococcus* spp. is *L. lactis*.

4. The system of claim 1 wherein the lactic acid bacterium is a *Lactobacillus* spp.

5. The system of claim 4 wherein the *Lactobacillus* spp. is *Lb. acidophilus, Lb. acidophilus, Lb. bulgaricus, Lb. reuteri*, or *Lb. plantarum*.

\* \* \* \* \*

UNITED STATES PATENT AND TRADEMARK OFFICE
CERTIFICATE OF CORRECTION

PATENT NO. : 11,533,915 B2
APPLICATION NO. : 17/067121
DATED : December 27, 2022
INVENTOR(S) : Yiannis J. Kaznessis et al.

It is certified that error appears in the above-identified patent and that said Letters Patent is hereby corrected as shown below:

On the Title Page

In item (62), In the Related U.S. Application Data section, should read --"Divisional application of application No. 15/894,408, filed Feb. 12, 2018, now Pat No. 10,813,956, which is a division of application No. 14/431,044, filed March 25, 2015, now Pat No. 9,925,223, which is a U.S. National Stage application of International Application No. PCT/US2013/061659, filed on September 25, 2013."--

In the Claims

In Claim 5 - delete the second, "Lb. acidophilus"

Signed and Sealed this
First Day of August, 2023

Katherine Kelly Vidal
*Director of the United States Patent and Trademark Office*